US008598120B2

(12) United States Patent
Soares et al.

(10) Patent No.: US 8,598,120 B2
(45) Date of Patent: *Dec. 3, 2013

(54) METHODS FOR TREATMENT USING AMYLIN FAMILY PEPTIDES

(75) Inventors: Christopher J. Soares, La Jolla, CA (US); Michael R. Hanley, Corte Madera, CA (US); Diana Y. Lewis, San Diego, CA (US); David G. Parkes, Del Mar, CA (US); Carolyn M. Jodka, Encinitas, CA (US); Kathryn S. Prickett, Foster City, CA (US); Soumitra S. Ghosh, San Diego, CA (US); Christine M. Mack, San Diego, CA (US); Qing Lin, Getzville, NY (US)

(73) Assignees: Amylin Pharmaceuticals, LLC, San Diego, CA (US); AstraZeneca Pharmaceuticals LP, Wilmington, DE (US)

(*) Notice: Subject to any disclaimer, the term of this patent is extended or adjusted under 35 U.S.C. 154(b) by 0 days.

This patent is subject to a terminal disclaimer.

(21) Appl. No.: 13/364,250

(22) Filed: Feb. 1, 2012

(65) Prior Publication Data

US 2012/0196796 A1 Aug. 2, 2012

Related U.S. Application Data

(62) Division of application No. 10/589,054, filed as application No. PCT/US2005/004631 on Feb. 11, 2005, now Pat. No. 8,114,958.

(60) Provisional application No. 60/543,275, filed on Feb. 11, 2004, provisional application No. 60/550,447, filed on Mar. 3, 2004.

(51) Int. Cl.
*A61K 38/16* (2006.01)
*A61P 3/04* (2006.01)
*A61P 5/22* (2006.01)
*C07K 14/435* (2006.01)
*C07K 19/00* (2006.01)

(52) U.S. Cl.
USPC .......... 514/11.9; 435/69.7; 514/4.9; 514/909; 530/307; 530/329; 536/23.4; 930/60

(58) Field of Classification Search
None
See application file for complete search history.

(56) References Cited

U.S. PATENT DOCUMENTS

| 5,124,314 | A | 6/1992 | Cooper |
| 5,264,372 | A | 11/1993 | Beaumont et al. |
| 5,578,708 | A | 11/1996 | Okazaki et al. |
| 5,580,953 | A | 12/1996 | Albrecht et al. |
| 5,677,279 | A | 10/1997 | Young |
| 5,686,411 | A | 11/1997 | Gaeta et al. |
| 5,739,106 | A | 4/1998 | Rink et al. |
| 5,766,627 | A | 6/1998 | Sankaram et al. |
| 5,998,367 | A | 12/1999 | Gaeta et al. |
| 6,087,334 | A | 7/2000 | Beeley et al. |
| 6,114,304 | A | 9/2000 | Kolterman et al. |
| 6,143,718 | A | 11/2000 | Kolterman et al. |
| 6,296,842 | B1 | 10/2001 | Jaworowicz et al. |
| 6,368,630 | B1 | 4/2002 | Bernstein et al. |
| 6,379,703 | B1 | 4/2002 | Lyons et al. |
| 6,379,704 | B2 | 4/2002 | Wright et al. |
| 6,410,511 | B2 | 6/2002 | L'Italien et al. |
| 6,458,387 | B1 | 10/2002 | Scott et al. |
| 6,610,824 | B2 | 8/2003 | Gaeta et al. |
| 6,936,584 | B1 | 8/2005 | Beeley et al. |
| 7,157,555 | B1 | 1/2007 | Beeley et al. |
| 7,220,721 | B1 | 5/2007 | Beeley et al. |
| 7,399,744 | B2 | 7/2008 | Mack et al. |
| 7,671,023 | B2 | 3/2010 | Laugero et al. |
| 7,741,269 | B2 | 6/2010 | Young et al. |
| 7,879,794 | B2 * | 2/2011 | Weyer et al. ............... 514/1.1 |
| 2003/0026182 | A1 | 2/2003 | Fischer et al. |
| 2003/0092606 | A1 | 5/2003 | L'Italien et al. |
| 2004/0022807 | A1 | 2/2004 | Duft et al. |
| 2006/0094652 | A1 | 5/2006 | Levy et al. |
| 2006/0094653 | A1 | 5/2006 | Levy et al. |
| 2006/0135747 | A1 | 6/2006 | Levy et al. |

FOREIGN PATENT DOCUMENTS

| EP | 289287 | 1/1998 |
| WO | WO 94/26292 | 11/1994 |
| WO | WO 98/50059 | 11/1998 |
| WO | WO 96/40196 | 2/1999 |
| WO | WO 99/07404 | 2/1999 |
| WO | WO 99/25727 | 5/1999 |
| WO | WO 99/25728 | 5/1999 |
| WO | WO 99/40928 | 8/1999 |
| WO | WO 2005/077072 | 8/2005 |
| WO | WO 2005/077094 | 8/2005 |

(Continued)

OTHER PUBLICATIONS

Bradley et al, 2010. Nutrition. 243-249.*
U.S. Appl. No. 60/543,275, filed Feb. 11, 2004.
Becker, *J. Clin Endocrinology & Metabolism* 89(4):1512-1525 (2004).
Beck-Sickinger et al., *Eur. J. Biochem.* 223:947-958 (1994).
Bray, *Am. J. Clin. Nutr.* 55:538S-544S (1992).
Campfield, *Science* 269:546-549 (1995).
Eiden et al., *J. Physiology* 541(3):1041-1048 (2002).
Fruin et al., *Digestion* 58(Suppl. 2):55 (1997).

(Continued)

*Primary Examiner* — Zachary Howard
(74) *Attorney, Agent, or Firm* — Womble Carlyle Sandridge & Rice, LLP; Mark Pino; Alireza Behrooz

(57) ABSTRACT

The present invention relates to novel compounds having a function of a peptide in the amylin family, related nucleic acids, expression constructs, host cells, and processes production of the compounds. The compounds of the invention include one or more amino acid sequence modifications. In addition, methods and compositions are disclosed to treat and prevent metabolic disorders such as obesity, diabetes, and increased cardiovascular risk.

8 Claims, 16 Drawing Sheets

(56) References Cited

FOREIGN PATENT DOCUMENTS

| WO | WO 2005/000222 | | 11/2005 |
|---|---|---|---|
| WO | WO 2006/066024 | | 6/2006 |
| WO | WO 2006/083254 | | 8/2006 |
| WO | WO 2006083254 A1 | * | 8/2006 |

OTHER PUBLICATIONS

Gibbs et al., *J. Biol. Chem.* 266:8923-8931 (1991).
Halaas, *Science* 269:543-546 (1995).
Hilton et al., *J. Endocrinology* 166(1):213-226 (Jul. 2000).
Jung, *Clin. Endocrinol. (Oxf.)* 35:11-20 (1991).
Kuczmarski, *Amer. J. Clin. Nutr.* 55:495S-502S (1992).
Kuestner, *Mol. Pharmacol.* 46:246-255 (1994).
Kurihara, *Hypertension Res.* 26 (Suppl):S105-S108 (Feb. 2003).
Lee et al., *Clin. Pediatr.* 31:234-236 (Apr. 1992).
Lutz el al., *Scientific World Journal* 1(12 Supp 1)25 (Dec. 18, 2001).
Lyznicki, *Am. Fam. Physician* 63:2185-2196 (2001).
Mack et al., *Diabetes* 52(Supp 1):A389 Abstract 1690-P (Jun. 2003).
Matsushita et al., *J. Biol. Chem*, 275:11044-11049 (2000).
Morley et al., Am. J. Physiol. 267:R178-R184 (1994).
Morrison et al., *Curr. Opin. Chem. Biol.* 5:302-307 (2001).
Muff et al., *Ann. NY Acad. Sci.* 657:106-116 (1992).
Pelleymounter et al., *Science* 269:540-543 (1995).
Poyner et al., *Br. J. Pharmacology* 124:(8):1659-1666 (Aug. 1998).
Reeder et al., *Can. Med. Assoc, J.* 146(11)2009-2019 (1992).
Rissanen etal., *Br. Med. J.* 301:835-837 (1990).
Rushing et al., *Endocrinology* 141(2):850-853 (2000).
Rushing et al., *Endocrinology* 142(11):5035-5038 (2001).
Rushing, Curr. Pharm Des. 9(10):819-925 (2003).
Sexton et al.,*Current Medicinal Chemistry* 6:1067-1093 (1999).
Surwit et al., *Metabolism* 44:645-651 (1995).
Thupari et al., Am. J. Physiol. Endocrinol. Metab. 287(1):E97-E104 (Jul. 2004).
Weintraub et al., *Medical Clinis of North America* 73(1):237 (1989).
Wimalawansa, *Crit. Rev. Neurobiol.* 11:167-239 (1997).
Zaidi et al., *Bone* 30(5):655-663 (2002).
Bork, Genome Research 10:398 (2000).
Brenner, Trends in Genetics 15(4):132 (1999).
Del Prete et al., Physiology & Behavior 75:593-599 (2002).
Doerks et al., Trends in Genetics 14(6):248 (1998).
Ngo et al., The Protein Folding Problem and Tertiary Structure Prediction, Chapter 14, pp. 433-440 and 492-495 (1994).
Reidelberger et al., Am. J. Physil. Reg. IntegratioN Comp. Physic!. 282(5):R1895-R1404 (2002).
Rossowski et al., Eur. J. Pharmacology 336:51-63 (1997).
Shigeaki et al., Biochem Mol Biol Intl 40(5):923-929 (1996).
Skolnick et al., Trends in Biotech 18(1)34 (2000).
Wells, *Biochemistry* 29(37):8509-8517 (1990).

* cited by examiner

Figure 2A
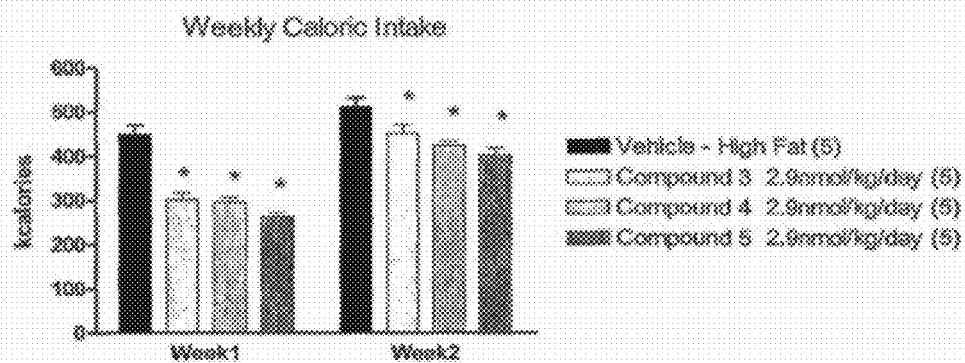
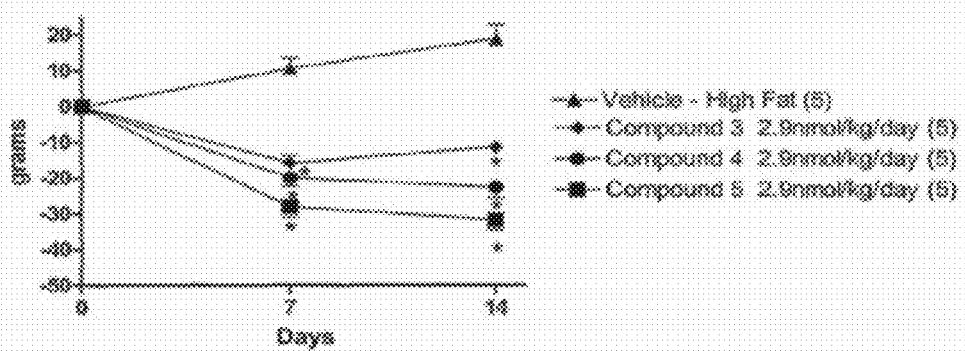
*P < 0.05 compared to respective vehicle-high fat group
Figure 2B

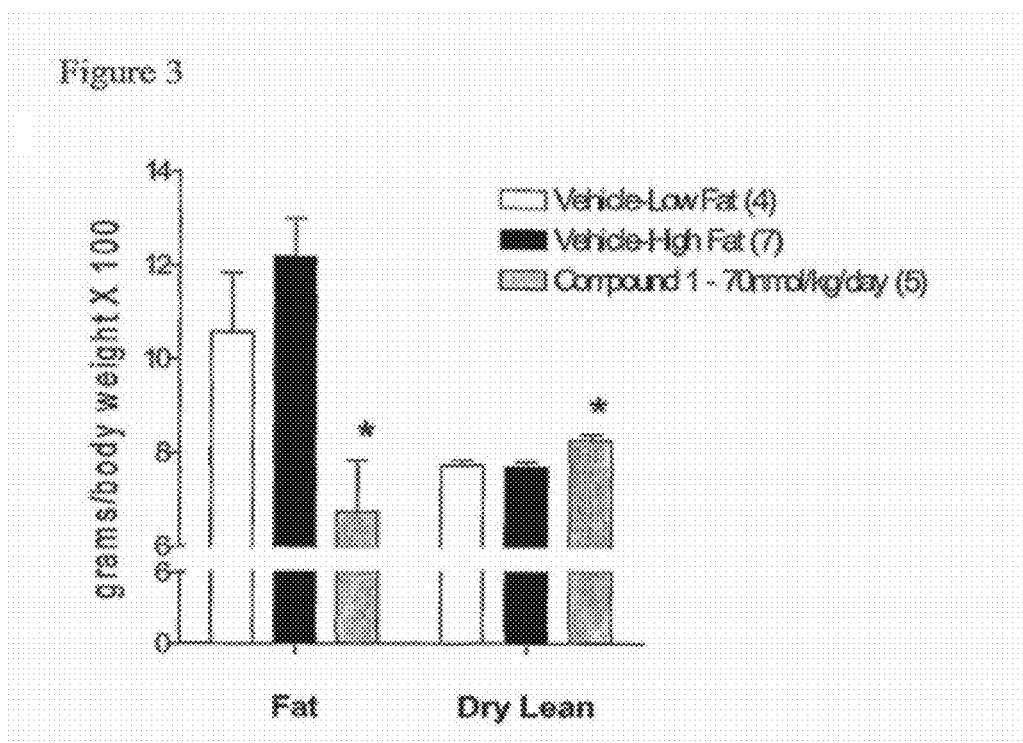

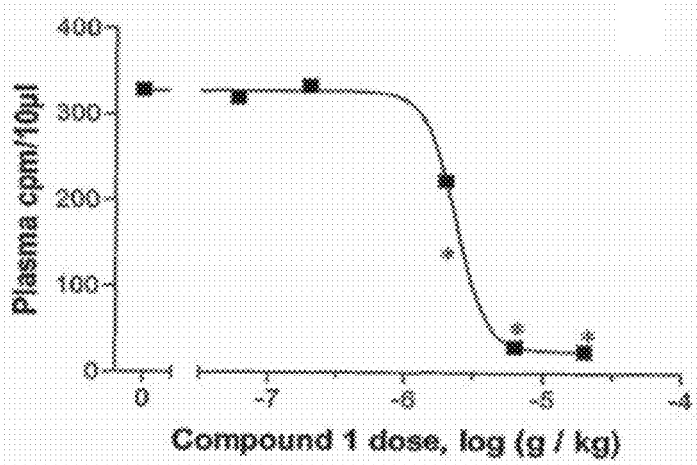

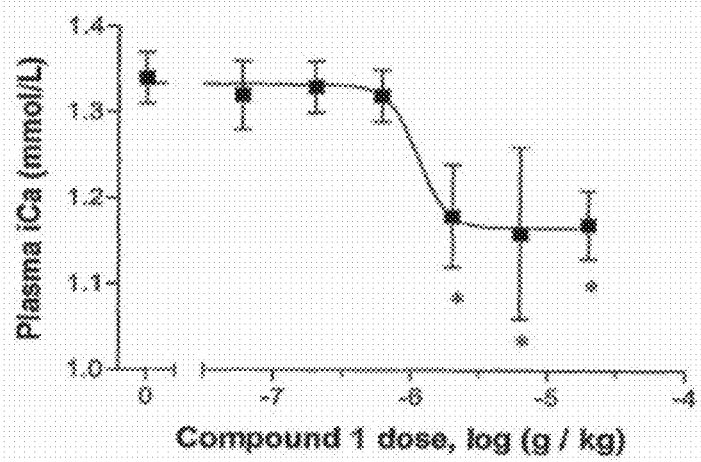

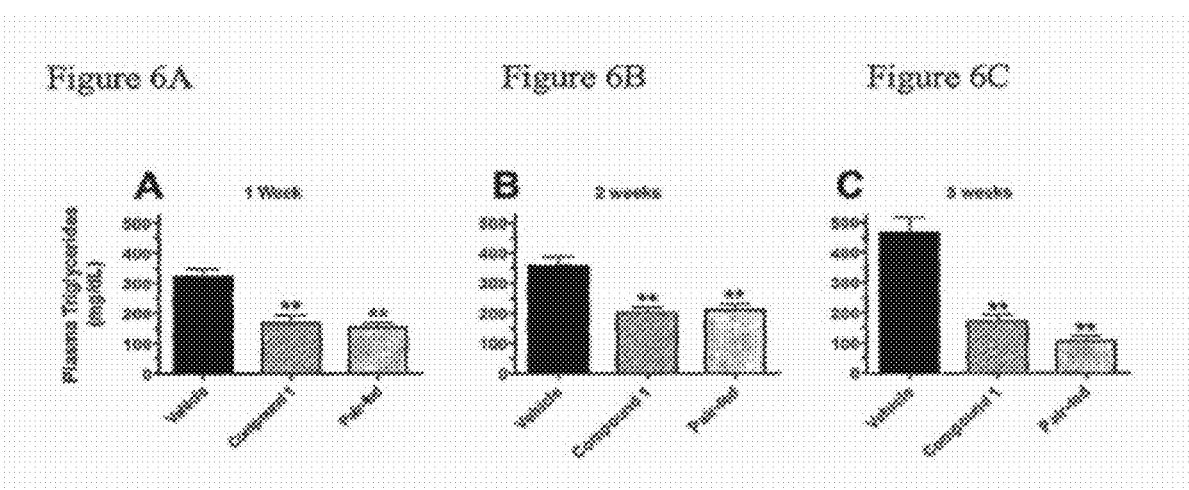

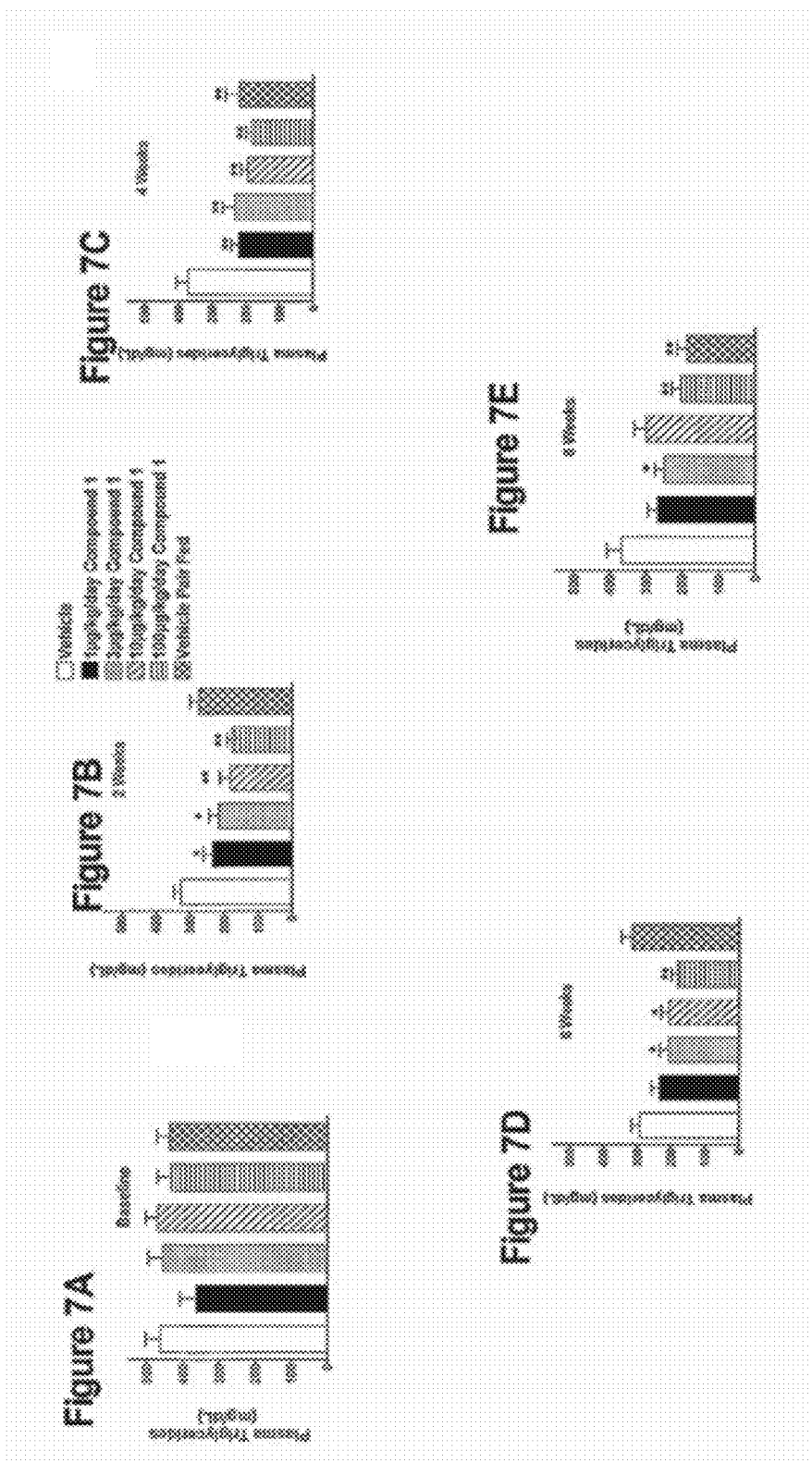

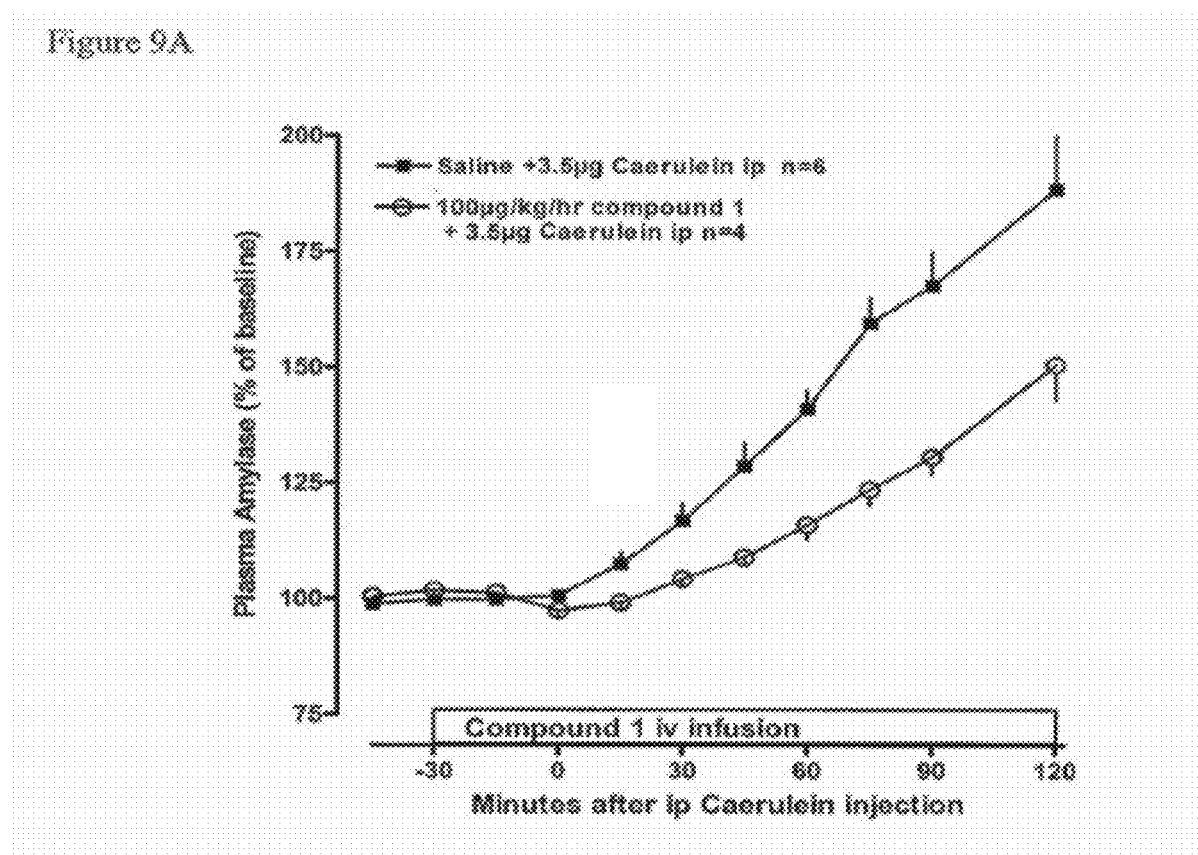

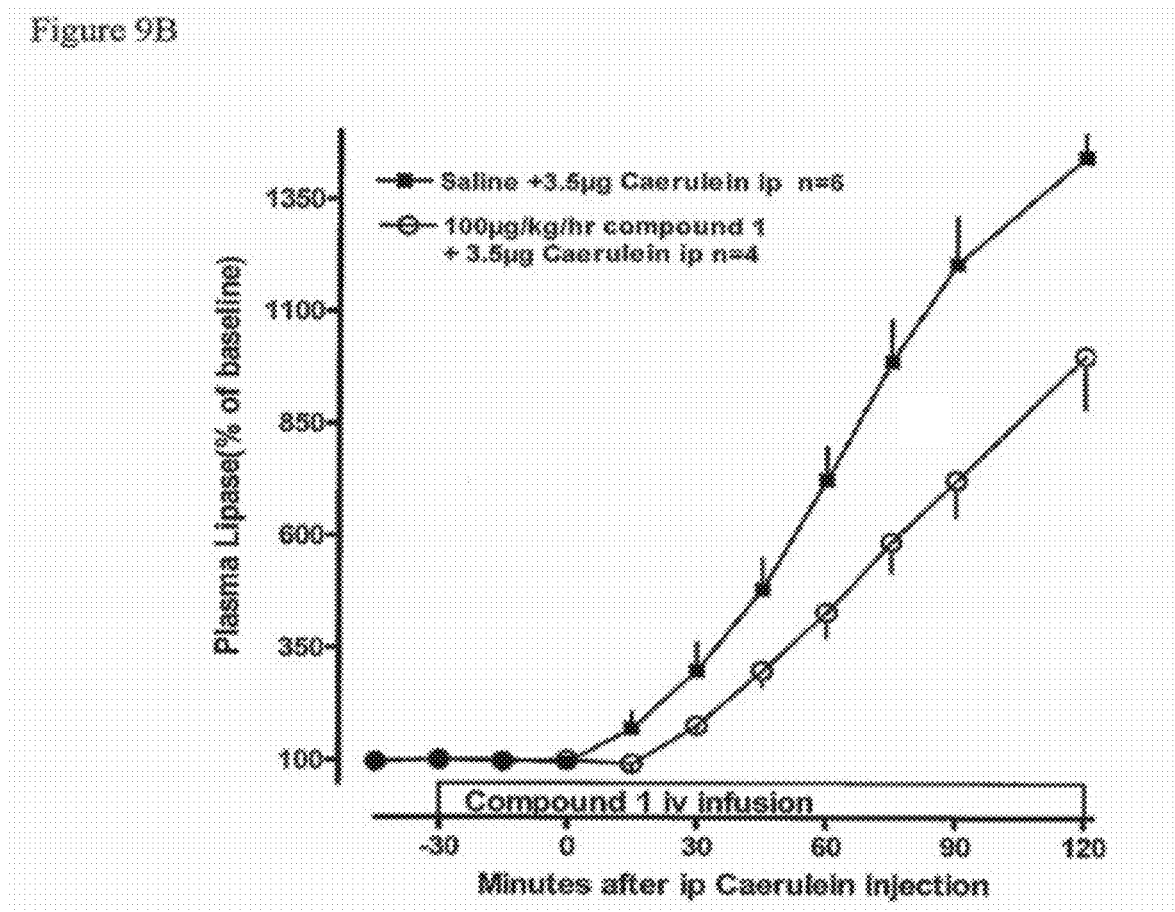

Figure 10A
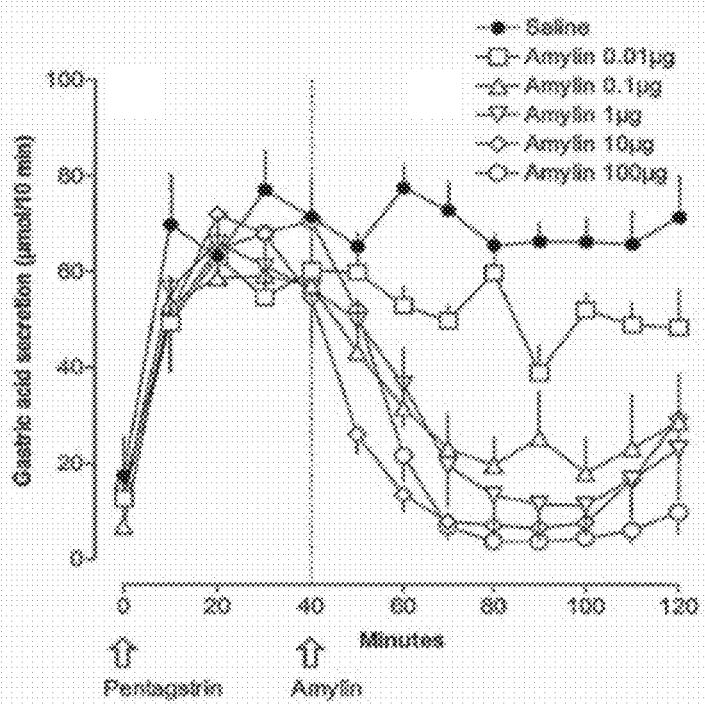
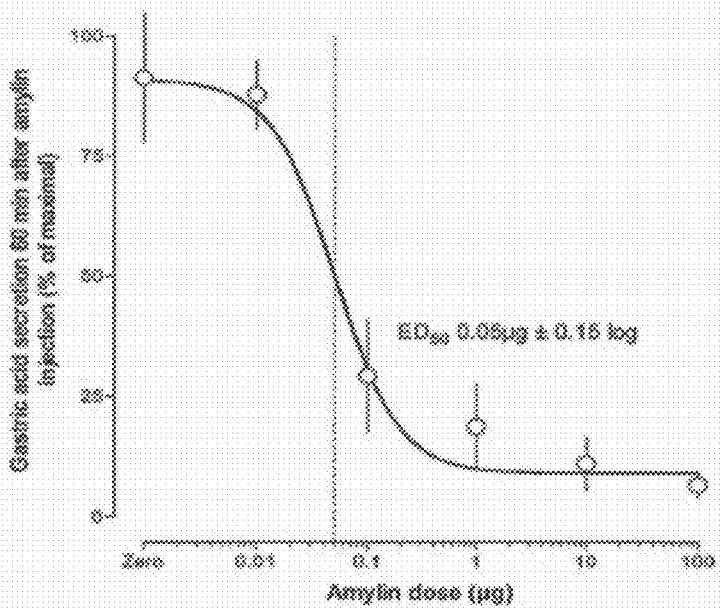
Figure 10B

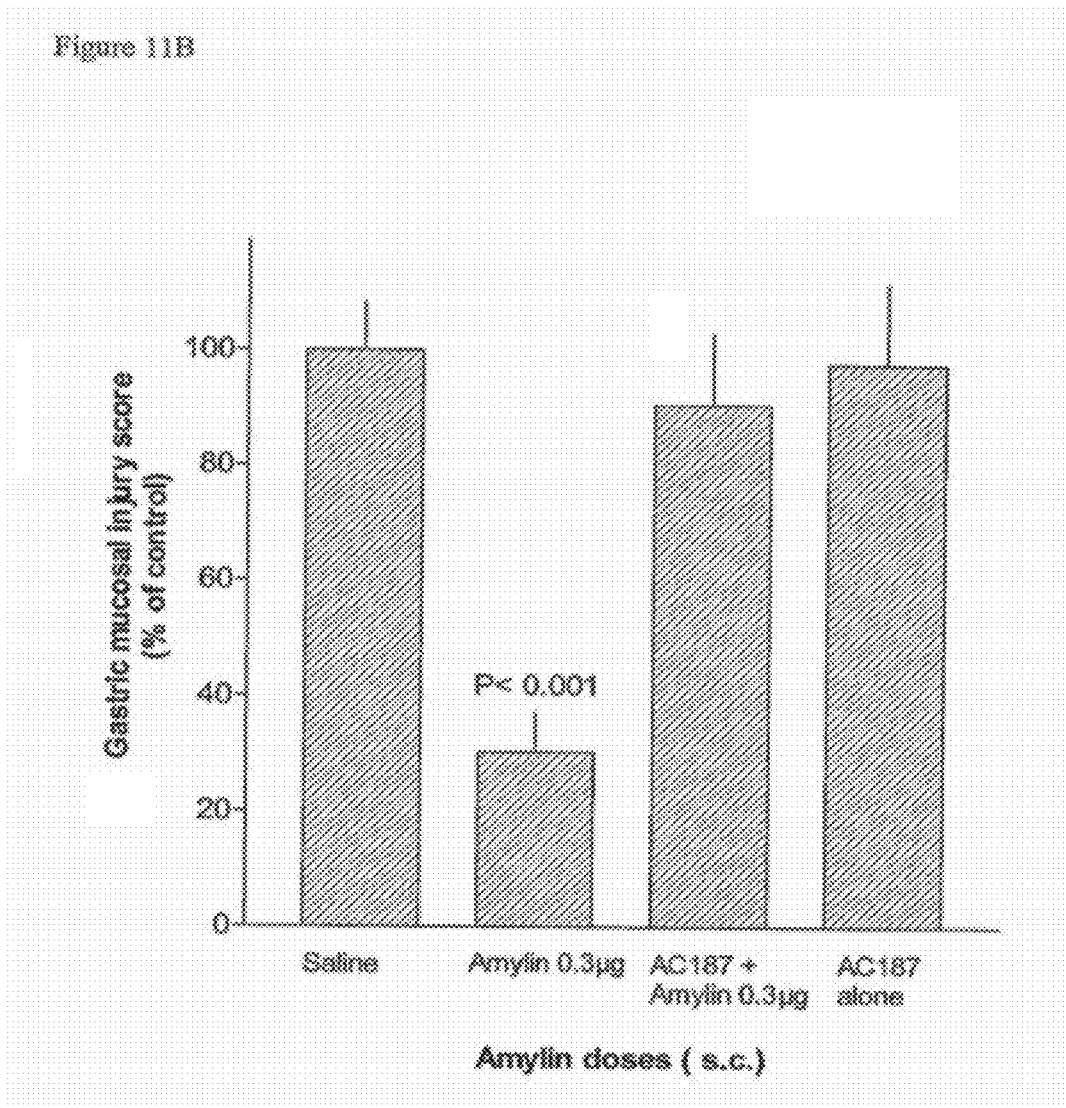

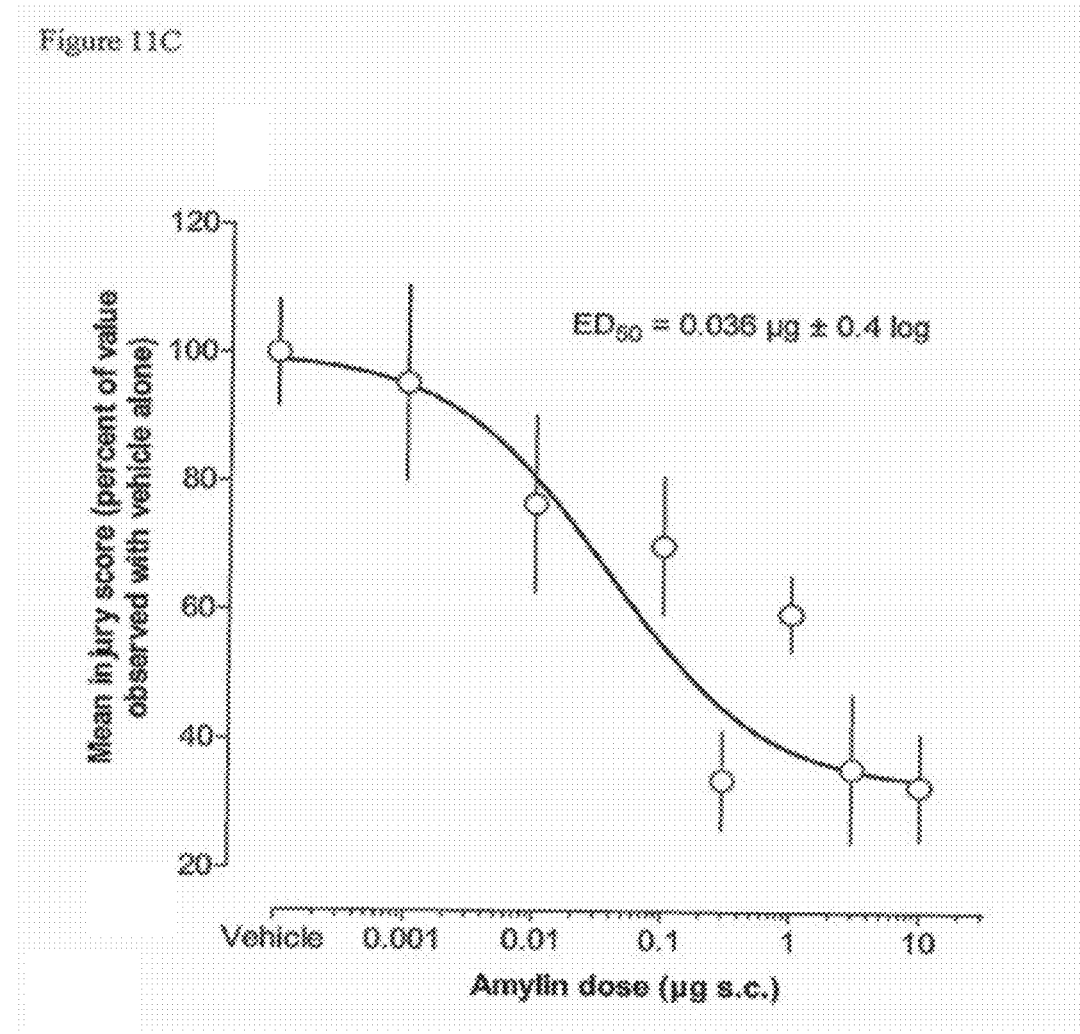

METHODS FOR TREATMENT USING AMYLIN FAMILY PEPTIDES

RELATED APPLICATIONS

The present application is a divisional of U.S. application Ser. No. 10/589,054, filed Aug. 10, 2006, now U.S. Pat. No. 8,114,958 issued Feb. 14, 2012, which is a national stage filing of International Application No. PCT/US2005/004631, filed Feb. 11, 2005, which claims the benefit of priority under 35 U.S.C. §119(e) of U.S. Provisional Application No. 60/543,275, filed Feb. 11, 2004, and of U.S. Provisional Application No. 60/550,447, filed Mar. 3, 2004, all of which are hereby incorporated by reference in their entirety.

SEQUENCE LISTING

The instant application contains a Sequence Listing which has been submitted in ASCII format via EFS-Web and is hereby incorporated by reference in its entirety. Said ASCII copy, created on Jan. 31, 2012, is named 0105US-DIV2-SEQ_ST25_2011-Mar.txt and is 70,209 bytes in size.

TECHNICAL FIELD

The present invention relates to novel compounds and methods for making and using them. These compounds may be useful for treating or preventing conditions such as metabolic disorders, vascular disorders, renal disorders, and/or gastrointestinal disorders. An exemplary condition might be one in which the reduction of food intake or caloric intake is of value, e.g., obesity, Type II diabetes, eating disorders, metabolic syndrome and insulin-resistance syndrome.

BACKGROUND

Much work had been done to date on amylin, calcitonin, and calcitonin gene related peptide (CGRP) to understand their structure and function. Table 1 provides a summary of some biological effects of CGRP, calcitonin and amylin as published in Wimalawansa, S. J. (1997) Critical Reviews in Neurobiology, 11; 167-239.

TABLE 1

| Biological effect | CGRP | Calcitonin | Amylin |
| --- | --- | --- | --- |
| Vasodilation | ++++ | +/− | ++ |
| Chronotropic | ++ | − | ++ |
| Inotropic | ++ | − | ++ |
| Inhibit bone resorption | + | ++++ | ++ |
| Stimulate bone formation | − | − | + |
| Calcium-lowering effect | − | +++ | ++ |
| Growth factor-like effect | + | − | + |
| Neural regeneration | ++ | +/− | − |
| Thermoregulation | + | − | + |
| Inflammation | ++ | +/− | − |
| Gastric mucosal protection | ++ | − | − |
| Effects on β cells | + | +/− | ++ |
| Skeletal muscle | + | − | + |
| Glucose metabolism | + | − | + |
| Anorectic effect | + | ++ | ++ |
| Analgesic effect | − | ++ | + |

Amylin has been reported to regulate gastric emptying and suppress glucagon secretion and food intake, thus regulating the rate of glucose appearance in the circulation. It appears to complement the actions of insulin, which regulates the rate of glucose disappearance from the circulation and its uptake by peripheral tissues. These actions are supported by experimental findings in rodents and humans, which indicate that amylin complements the effects of insulin in postprandial glucose control by at least three independent mechanisms, all of which affect the rate of glucose appearance. First, amylin suppresses postprandial glucagon secretion. Compared to healthy adults, patients with type 1 diabetes have no circulating amylin and patients with type 2 diabetes have diminished postprandial amylin concentrations. Furthermore, infusion of an amylin specific monoclonal antibody, which bound circulating amylin, again resulted in greatly elevated glucagon concentrations relative to controls. Both of these results point to a physiological role of endogenous amylin in the regulation of postprandial glucagon secretion. Second, amylin slows gastrointestinal motility and gastric emptying. Finally, intrahypothalamic injections of rat amylin were shown to reduce feeding in rats and alter neurotransmitter metabolism in the hypothalamus. In certain studies, food intake was significantly reduced for up to eight hours following the intrahypothalamic injection of rat amylin and rat CGRP. In human trials, an amylin analog, pramlintide, has been shown to reduce weight or weight gain. Amylin may be beneficial in treating metabolic conditions such as diabetes and obesity. Amylin may also be used to treat pain, bone disorders, gastritis, to modulate lipids, in particular triglycerides, or to affect body composition such as the preferential loss of fat and sparing of lean tissue.

The hormone calcitonin (CT) was named for its secretion in response to induced hypercalcemia and its rapid hypocalcemic effect. It is produced in and secreted from neuroendocrine cells in the thyroid that have since been termed C cells. The best-studied action of CT(1-32) is its effect on the osteoclast. In vitro effects of CT include the rapid loss of ruffled borders and decreased release of lysosomal enzymes. Ultimately, the inhibition of osteoclast functions by CT results in a decrease in bone resorption. However, neither a chronic reduction of serum CT in the case of thyroidectomy nor the increased serum CT found in medullary thyroid cancer appears to be associated with changes in serum calcium or bone mass. It is thus most likely that a major function of CT(1-32) is to combat acute hypercalcemia in emergency situations and/or protect the skeleton during periods of "calcium stress" such as growth, pregnancy, and lactation. (Reviewed in Becker, JCEM, 89(4): 1512-1525 (2004) and Sexton, Current Medicinal Chemistry 6: 1067-1093 (1999)). Consistent with this is recent data from the calcitonin gene knockout mouse, which removes both the calcitonin and the CGRP-I peptides, that revealed that the mouse had normal levels of basal calcium-related values, but an increased calcemic response (Kurihara H, et al, Hypertens Res. 2003 February; 26 Suppl:S 105-8).

CT has an effect on plasma calcium levels and inhibits osteoclast function and is widely used for the treatment of osteoporosis. Therapeutically, salmon CT appears to increase bone density and decrease fracture rates with minimal adverse effects. CT has also been successfully used over the past 25 years as a therapy for Paget's disease of bone, which is a chronic skeletal disorder that may result in enlarged or deformed bones in one or more regions of the skeleton. CT is also widely used for its analgesic effect on bone pain experienced during osteoporosis, although the mechanism for this effect is not clearly understood.

Calcitonin gene related peptide (CGRP) is a neuropeptide whose receptors are widely distributed in the body, including the nervous system and the cardiovascular system. This peptide seems to modulate sensory neurotransmission and is one of the most potent endogenous vasodilatory peptides discovered to date. Reported biological effects for CGRP include:

modulation of substance P in inflammation, nicotinic receptor activity at the neuromuscular junction, stimulation of pancreatic enzyme secretion, a reduction of gastric acid secretion, peripheral vasodilation, cardiac acceleration, neuromodulation, regulation of calcium metabolism, osteogenic stimulation, insulin secretion, an increase in body temperature and a decrease in food intake. (Wimalawansa, Amylin, calcitonin gene-related peptide, calcitonin and ADM: a peptide superfamily. Crit Rev Neurobiol. 1997; 11(2-3): 167-239). An important role of CGRP is to control blood flow to various organs by its potent vasodilatory actions, as evidenced by a decrease of mean arterial pressure following intravenous administration of CGRP. The vasodilatory actions are also supported by recent analysis of homozygous knockout CGRP mice, which demonstrated elevated peripheral vascular resistance and high blood pressure caused by increased peripheral sympathetic activity (Kurihara H, et al, Targeted disruption of ADM and alphaCGRP genes reveals their distinct biological roles. Hypertens Res. 2003 February; 26 SuppliS105-8). Thus, CGRP appears to elicit vasodilatory effects, hypotensive effects and an increase in heart rate among other actions.

Prolonged infusion of CGRP into patients with congestive cardiac failure has shown a sustained beneficial effect on hemodynamic functions without adverse effects, suggesting a use in heart failure. Other indications of CGRP use include renal failure, acute and chronic coronary artery ischemia, treatment of cardiac arrhythmia, other peripheral vascular disease such as Raynaud's phenomenon, subarachnoid hemorrhage, hypertension, and pulmonary hypertension. Preeclamptic toxemia of pregnancy and preterm labor is also potentially treatable. (Wimalawansa, 1997). Recent therapeutic uses include the use of CGRP antagonists for the treatment of migraine headaches.

There are many beneficial properties of each peptide that can be used alone or in combination to treat or prevent a variety of conditions. It would be useful to create new and useful peptides having multiple actions that impart improved characteristics not possessed by the existing peptides. For example, in food intake assays, amylin has been shown to have a quick onset, within 30 minutes, but its effect tapers off after 60 minutes. In contrast, salmon calcitonin has been shown to have a delayed effect, with peak levels still maintained at 240 minutes. Novel compounds that can mimic the effects of amylin and/or calcitonin and have quick onset of activity like amylin with the sustained activity of calcitonin may increase the potency and efficacy of either compound alone. Moreover, the combination of certain physicochemical characteristics of amylin, calcitonin, and/or CGRP into a single modality may facilitate intervention at different points in a dysfunctional metabolic circuit. These novel compounds combine desirable activities or properties for a superior therapeutic, which may result in compounds having at least one desirable characteristic such as higher efficacy, greater potency, greater bioavailability, fewer side effects, ease in manufacture, stability, and/or solubility.

All documents referred to herein are incorporated by reference into the present application as though fully set forth herein.

SUMMARY

The present invention relates, at least in part, to novel amylin family peptides or compound. In a general aspect, these novel compounds (also referred to as compounds of the invention) have at least a loop region of amylin or calcitonin and analogs thereof; an α helix region of at least a portion of an α helix region of calcitonin or analogs thereof or an α helix region having a portion of an amylin α helix region and a calcitonin α helix region, or their respective analogs; and a C-terminal tail of amylin or calcitonin or analogs thereof, with the proviso that the C-terminal tail of calcitonin or a calcitonin analog is not proline (Pro), hydroxyproline (Hyp), homoSerine (Hse) or derivatives of Hse.

As used herein, an "analog" refers to a peptide whose sequence was derived from that of a base reference peptide, e.g., amylin and calcitonin, and includes insertions, substitutions, extensions, and/or deletions of the reference amino acid sequence, preferably having at least 50 or 55% amino acid sequence identity with the base peptide, more preferably having at least 70%, 80%, 90%, or 95% amino acid sequence identity with the base peptide. In one embodiment, such analogs may comprise conservative or non-conservative amino acid substitutions (including non-natural amino acids and L and D forms). Analogs include compounds having agonist and compounds having antagonist activity. Analogs, as herein defined, also include derivatives.

A "derivative" is defined as a reference peptide or analogs, described above, having a chemical modification of one or more of its amino acid side groups, α-carbon atoms, terminal amino group, or terminal carboxylic acid group. A chemical modification includes, but is not limited to, adding chemical moieties, creating new bonds, and removing chemical moieties. Modifications at amino acid side groups include, without limitation, acylation of lysine ϵ-amino groups, N-alkylation of arginine, histidine, or lysine, alkylation of glutamic or aspartic carboxylic acid groups, and deamidation of glutamine or asparagine. Modifications of the terminal amino include, without limitation, the desamino, N-lower alkyl, N-di-lower alkyl, and N-acyl modifications. Modifications of the terminal amino include, without limitation, the desamino, N-lower alkyl, N-di-lower alkyl, and N-acyl modifications, such as alkyl acyls, branched alkylacyls, alkylaryl-acyls. Modifications of the terminal carboxy group include, without limitation, the amide, lower alkyl amide, dialkyl amide, arylamide, alkylarylamide and lower alkyl ester modifications. Lower alkyl is C1-C4 alkyl. Furthermore, one or more side groups, or terminal groups, may be protected by protective groups known to the ordinarily-skilled synthetic chemist. The α-carbon of an amino acid may be mono- or dimethylated.

In certain embodiments, the novel compounds have an amylin or amylin analog loop region, at least a portion of a calcitonin or calcitonin analog α helix region, and an amylin or amylin analog C-terminal tail. In other embodiments, the novel compounds have a calcitonin or calcitonin analog loop region, at least a portion of a calcitonin or calcitonin analog α helix region, and an amylin or amylin analog C-terminal tail. In still other embodiments, the novel compounds have an amylin or amylin analog loop region, at least a portion of an amylin or amylin analog α helix region and at least a portion of a calcitonin or calcitonin analog α helix region, and an amylin or amylin analog C-terminal tail. In yet other embodiments, the novel compounds have a calcitonin or calcitonin analog loop region, at least a portion of an amylin or amylin analog α helix region and at least a portion of a calcitonin or calcitonin analog α helix region, and an amylin or amylin analog C-terminal tail. In still yet other embodiments, the novel compounds have an amylin or amylin analog loop region, a portion or a calcitonin or calcitonin analog α helix region or at least a portion of an amylin or amylin analog α helix region and at least a portion of a calcitonin or calcitonin analog α helix region, and a calcitonin or calcitonin analog C-terminal tail.

In certain embodiments, the loop region of the novel compounds may further comprise no more than one, two, three, or four modifications including substitutions, insertions, or deletions from the amylin or calcitonin loop, and analogs thereof. It is further contemplated that the novel compounds may have additional modifications at the N-terminal portion of the loop comprising a N-cap region, that may have hydrophobic or hydrophilic characteristics such as acetyl, isocaproyl, 3,6-dioxyoctanoic acid, or 1-amino-4,7,10-trioxa-13-tridecanamine succinimic acid. Modifications may further include one, two, three or more additional amino acids. This is an area which allows for many modifications too numerous to mention, but would be understood by one of skill in the art based upon what is exemplified further in the present application.

In general, with respect to an amino acid sequence, the term "modification" includes substitutions, insertions, elongations deletions, and derivatizations alone or in combination. The novel compounds of the invention may include one or more modifications of a "non-essential" amino acid residue. In the context of the invention, a "non-essential" amino acid residue is a residue that can be altered, i.e., deleted or substituted, in the novel amino acid sequence without abolishing or substantially reducing the agonist activity of the analog polypeptide.

Substitutions include conservative amino acid substitutions. A "conservative amino acid substitution" is one in which the amino acid residue is replaced with an amino acid residue having a similar side chain, or physicochemical characteristics (e.g., electrostatic, hydrogen bonding, isosteric, hydrophobic features). The amino acids may be naturally occurring or nonnatural (unnatural). Families of amino acid residues having similar side chains are known in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, methionine, cysteine), nonpolar side chains (e.g., alanine, valine, leucine, isoleucine, proline, phenylalanine, tryptophan), β-branched side chains (e.g., threonine, valine, isoleucine) and aromatic side chains (e.g., tyrosine, phenylalanine, tryptophan, histidine). Substitutions may also include non-conservative changes.

The compounds of the invention may also be further derivatized by chemical alterations such as amidation, glycosylation, acylation, sulfation, phosphorylation, acetylation, and cyclization. Such chemical alterations may be obtained through chemical or biochemical methodologies, as well as through in-vivo processes, or any combination thereof. Derivatives of the compounds of the invention may also include conjugation to one or more polymers or small molecule substituents. One type of polymer conjugation is linkage or attachment of polyethylene glycol ("PEG") polymers, polyamino acids (e.g., poly-his, poly-arg, poly-lys, etc.) and/or fatty acid chains of various lengths to the N- or C-terminus or amino acid residue side chains of an AFP-6 analog. Small molecule substituents include short alkyls and constrained alkyls (e.g., branched, cyclic, fused, adamantyl), and aromatic groups. In addition, basic residues such as R and K may be replaced with homoR and homoK, citrulline, or ornithine to improve metabolic stability of the peptide. Compounds of the invention also include acid as well as amide forms of the peptides.

In certain embodiments, the α helix region of the novel compounds comprise at least four consecutive amino acids of a calcitonin or calcitonin analog α helix region. In other embodiment, the α helix region comprises at least 5, 6, 7, or 8 consecutive amino acids of a calcitonin or calcitonin analog α helix region. In other embodiments, the α helix region comprises at least 10, 11, 12, 13, 14, 15, 16, 17, 18, 19, 20, 21 or more consecutive amino acids of a calcitonin or calcitonin analog α helix region. In certain embodiments, when the number of consecutive amino acids are less than 8, it is contemplated that the α helix region further comprises at least 4, 5, 6, 7, 9, 10, 11, or more consecutive amino acid of an amylin or amylin analog α helix region. In certain embodiments, it is envisioned that the less amino acids of calcitonin or calcitonin analog, the more amino acids of an amylin or amylin analog may be found in the α helix region of the novel compounds. The number of amino acids comprising the α helix region may be from about 10 to 23 amino acids. Accordingly, the α helix region may be 10, 11, 12, 13, 14, 15, 16, 17, 18, 19, 20, 21, 22, or 23 amino acids long. Moreover, the amino acids should provide for about three to about six α helical turns. It is further contemplated that the α helix region of the novel compounds may further comprise no more than one, two, three, four, five, six, seven, eight or 10 modifications including substitutions, insertions, or deletions from that of the calcitonin and/or amylin α helix region, and analogs thereof.

In certain embodiments, the C-terminal tail of the novel compounds comprise at least the last six, five, or four amino acids of either amylin or calcitonin, and analogs thereof. In certain embodiments, the C-terminal tail of the novel compounds comprise at least a portion of the C-terminal end having a β turn. In certain embodiments, the β turn is introduced by the amino acid combination of Gly-Ser. Accordingly, the novel compounds may have a C-terminal end comprising a portion of an amylin or calcitonin C-terminal tail (and analogs thereof) having Gly-Ser or starting at Gly-Ser.

In certain embodiments, the C-terminal tail of the novel compounds may further comprise no more than one, two, or three, modifications including substitutions, insertions, or deletions from the amylin or calcitonin loop, and analogs thereof. It is further contemplated that the novel compounds may have additional modifications at the C-terminal portion of the C-terminal tail which may include L-octylglycine, 4ABU (4-aminobutyric acid), 9Anc (9 amiononanoic acid, 3,6-dioxyoctanoic acid or 1-amino-4,7,10-trioxa-13-tridecanamine succinimic acid. Modification may further include one, two, three or more additional amino acids. The types of modification contemplated in this area would be understood by one of skill in the art based upon what is exemplified further in the present application.

In one aspect, a loop region is defined as that region found at the N-terminal end comprising at least 5 to 8 amino acids, wherein the first and last amino acid are capable of creating a bond, for example, residues at positions 2-7 of amylin or residues at positions 1-7 of calcitonin and their corresponding regions in their respective analogs. In another aspect, a α helix region is defined as the internal portion of amylin or calcitonin flanked by the loop region and the C-terminal tail which structurally forms an α helix, for example, residues at positions 8-23 of amylin or residues at positions 8-27 of calcitonin and their corresponding regions in their respective analogs. In yet another aspect, a C-terminal tail is defined as that region after the α helix e.g., residues at positions 33-37 of amylin or longer such as residues at positions 27-37 or residues at positions 27 or 28 to 32 of calcitonin. Included in the compounds of the invention are both the amide and acid forms of the disclosed compounds.

Amylin and calcitonin, as herein defined, includes all native and species variations. Examples of amylin and calcitonin include, but are not limited to:

```
human amylin (hAmylin)
                                              (SEQ ID NO: 1)
KCNTATCATQRLANFLVHSSNNFGAILSSTNVGSNTY rat amylin (rAmylin)
                                              (SEQ ID NO: 2)
KCNTATCATQRLANFLVRSSNNLGPVLPPTNVGSNTY salmon calcitonin (sCT)
                                              (SEQ ID NO: 3)
CSNLSTCVLGKLSQELHKLQTYPRTNTGSGTP human calcitonin (hCT)
                                              (SEQ ID NO: 4)
CGNLSTCMLGTYTQDFNKFHTFPQTAIGVGAP.
```

By "amino acid" and "amino acid residue" is meant natural amino acids, unnatural amino acids, and modified amino acid. Unless stated to the contrary, any reference to an amino acid, generally or specifically by name, includes reference to both the D and the L stereoisomers if their structure allow such stereoisomeric forms. Natural amino acids include alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), Lysine (Lys), methionine (Met), phenylalanine (Phe), proline (Pro), serine (Ser), threonine (Thr), tryptophan (Trp), tyrosine (Tyr) and valine (Val). Unnatural amino acids include, but are not limited to homolysine, homoarginine, homoserine azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisbutyric acid, 2-aminopimelic acid, tertiary-butylglycine, 2,4-diaminoisobutyric acid, desmosine, 2,2'-diaminopimelic acid, 2,3-diaminopropionic acid, N-ethylglycine, N-ethylasparagine, homoproline, hydroxylysine, allo-hydroxylysine, 3-hydroxyproline, 4-hydroxyproline, isodesmosine, allo-isoleucine, N-methylalanine, N-methylglycine, N-methylisoleucine, N-methylpentylglycine, N-methylvaline, naphthalanine, norvaline, norleucine, ornithine, pentylglycine, pipecolic acid and thioproline. Additional unnatural amino acids include modified amino acid residues which are chemically blocked, reversibly or irreversibly, or chemically modified on their N-terminal amino group or their side chain groups, as for example, N-methylated D and L amino acids or residues wherein the side chain functional groups are chemically modified to another functional group. For example, modified amino acids include methionine sulfoxide; methionine sulfone; aspartic acid-(beta-methyl ester), a modified amino acid of aspartic acid; N-ethylglycine, a modified amino acid of glycine; or alanine carboxamide, a modified amino acid of alanine. Additional residues that can be incorporated are described in Sandberg et al., *J. Med. Chem.* 41: 2481-91, 1998.

In a general aspect, compounds of the invention comprise at least a loop region, an α helix region, and a C-terminal tail. The loop region comprises an amino sequence comprising the formula X-Xaa1 sequence-Y wherein X and Y are capable of creating a bond and are independently selected residues having side chains which are chemically bonded to each other to form an intramolecular linkage such as disulfide bonds; amide bond; alkyl acids and alkyl amines which may form cyclic lactams; alkyl aldehydes or alkyl halides and alkylamines which may condensed and be reduced to form an alkyl amine or imine bridge; or side chains which may be connected to form an alkyl, alkenyl, alkynyl, ether or thioether bond. Alkyl chains may include lower alkyl groups having from about 1 to about 6 carbon atoms. In certain embodiments, the intramolecular linkage may be a disulfide, amide, imine, amine, alkyl and alkene bond. In certain embodiments, X and Y are independently selected from Ser, Asp, Glu, Lys, Orn, or Cys. In certain embodiments, X and Y are Cys and Cys. In other embodiments, X and Y are Ser and Ser. In still other embodiments, X and Y are Asp and Lys or Lys and Asp.

The Xaa1 sequence comprises an amino acid sequence of 3, 4, 5, or 6 amino acids between X and Y. In certain embodiments, the Xaa1 sequence comprises an amino acid sequence having a region with one or more substituted or unsubstituted hydroxyl-containing residues next to Y. For example, the hydroxyl containing residue region may have at least 2 of the 3 amino acids adjacent Y that are either a Ser or Thr. The other amino acids in the Xaa1 sequence may be any amino acid. In certain embodiments, the Xaa1 sequence is 3 amino acids. In other embodiments, the Xaa1 sequence is 4 amino acids. In still other embodiments, the Xaa1 sequence is 5 amino acids. In yet other embodiments, the Xaa1 sequence is 6 amino acids. Accordingly, Xaa1 can be represented by Xaa2-Xaa3-Xaa4-Xaa5-Xaa6-Xaa7 (SEQ ID NO:5). In certain embodiments, Xaa2, Xaa3, and/or Xaa4 may absent. In certain embodiments, Xaa5, Xaa6, and Xaa7 comprise the hydroxy-containing residue region. As such, at least two of the three amino acids can be a Ser, hSer, Thr, alloThr, d-Thr, or other unnatural analog thereof. Xaa2 can be any amino acid or absent, Xaa3 can be any amino acid or absent, Xaa4 can be any amino acid or absent, Xaa5 can be any amino acid if Xaa6 is a Ser or Thr and Xaa7 is a Ser or Thr, Xaa6 can be any amino acid if Xaa5 is a Ser or Thr and Xaa7 is a Ser or Thr, Xaa7 can be any amino acid if Xaa5 is Ser or Thr and Xaa6 is Ser or Thr. Accordingly, in certain embodiment, Xaa1 can be represented as Xaa2 absent, Xaa3 is Ala, Gly, Ser, Asp or absent, Xaa4 is Asn, Ala, Asp, Gly or absent; Xaa5 is Ala, Leu, Thr, or Ser; Xaa6 is Ala, Ser, or Thr; and Xaa7 is Ala, Ser, Val, Hse, (S)-2-amio-3-hydroxy-methylbutanoic acid (Ahb), (2S,3R)-2-amino-3hydroxy-methylpentanoic acid (Ahp), D-Thr, Thr, or a derivative thereof. In other embodiments Xaa1 can be represented as Xaa2 is absent, Xaa3 is Ser, Gly, or absent, Xaa4 is Asn or Asp, Xaa5 is Ala, Ser, Thr or Leu, Xaa6 is Ala, Thr or Ser, and Xaa7 is Ser, D-Thr, alloThr or Thr. In certain embodiments, the loop region comprises the above-described representations of Xaa1 wherein Xaa3 is Ala, wherein Xaa3 is Ser or wherein Xaa3 is Gly. Alternatively or additionally, the loop region comprises the above described representations of Xaa1 wherein Xaa4 is Ala, wherein Xaa4 is Asn, wherein Xaa4 is Asp, or wherein Xaa4 is Gly. Alternatively or additionally, the loop region comprises the above-described representations of Xaa1 wherein Xaa5 is Ala, wherein Xaa5 is Thr, or wherein Xaa5 is Leu. Alternatively or additionally, the loop region comprises the above described representations of Xaa1 wherein Xaa6 is Ser or wherein Xaa6 is Ala. Alternatively or additionally, the loop region comprises the above-described representations of Xaa1 wherein Xaa7 is Thr or wherein Xaa7 is D-Thr. It is further contemplated that no more than one, two, or three modifications such as substitutions, insertions, deletions, and/or derivatizations may be made to the loop region.

It should be noted that throughout the application that alternatives are written in Markush groups, for example, each amino acid position that contains more than one possible amino acid. It is specifically contemplated that each member of the Markush group should be considered separately, thereby comprising another embodiment of the invention, and the Markush group is not to be read as a single unit.

Examples of the loop region of the invention include, but are not limited to, C-N-T-A-T-C (SEQ ID NO:6); C-A-T-A-T-C (SEQ ID NO:7); C-D-T-A-T-C (SEQ ID NO:8); C-G-T-

A-T-C (SEQ ID NO:9); C-N-A-A-T-C (SEQ ID NO:10); C-N-T-S-T-C (SEQ ID NO:11; C-N-T-A-dThr-C (SEQ ID NO:12); C-N-T-A-T (OPO3H2)-C (SEQ ID NO:13); C-N-T-A-S-C (SEQ ID NO:14); C-N-T-A-A-C (SEQ ID NO:15); C-N-T-A-V-C (SEQ ID NO:16); C-N-T-A-Hse-C (SEQ ID NO:17); C-N-T-A-Ahb-C (SEQ ID NO:18); C-N-T-A-Ahp-C (SEQ ID NO:19); C-S-N-L-S-T-C (SEQ ID NO:20); C-G-N-L-S-T-C (SEQ ID NO:21); C-A-N-L-S-T-C (SEQ ID NO:22); C-S-A-L-S-T-C (SEQ ID NO:23); C-S-N-A-S-T-C (SEQ ID NO:24); C-S-N-L-A-T-C (SEQ ID NO:25); and C-S-N-L-S-A-C (SEQ ID NO:26). As previously noted, it is further contemplated that no more than one, two, or three modifications such as substitutions, insertions, deletions, and/or derivatizations may be made to the loop region.

The loop region of the novel compounds may further comprise modifications or additional amino acids at the N-terminal end. Such modifications include the addition of compounds such as Lys, Ala, Phe, Ile, Ser, Octylglycine, Isocap, Fmoc-3,6-dioxyoctanoic acid, Fmoc-1-amino-4,7,10-trioxa-13-tridecanamine succinimic acid, acetyl, and/or groups for solubility, delivery, signaling. Exemplary modified loops include the addition of Lys the sequence of Xaa1 or the addition of Ile to the sequence of Xaa1. For example, the modified loop region may be K-C-N-T-A-T-C (SEQ ID NO:27). In certain embodiments, the additions and/or modifications at the N-terminal end of the loop region may change the loop region. For example, the loop region of the invention may be modified as follows: cyclo(2,7) 1-7 hAmylin, cyclo (2Asp 7Lys) 1-7 hAmylin, N-isocaproyl 1-7 hAmylin, N-3,6 dioxaoctanoyl 1-7 hAmylin, L-Octylglycine 1-7 hAmylin, Acetyl (2Agy, 7Agy) 1-7 hAmylin wherein Agy is Allylglycine, Acetyl (1Ala) 1-7 hAmylin, (1Thr 3Asp) 1-7 hAmylin, Isocap (7Ala) 5-7 sCT, Acetyl (2Agy, 7Agy) 1-7 sCT, and cyclo (1,7) (1Asp 7Lys) 1-7 sCT. Therefore, taking the example of Isocap(7Ala) 5-7 sCT, certain embodiments of the invention comprise a modification at the N-terminal region of the loop region of the invention such that amino acids Xaa2 to Xaa5 are absent.

Throughout the application, the amino acid sequences may be referred to as amino acids at position a to position b adjacent to a reference peptide. In the present application the reference peptide is amylin and calcitonin, which sequences are provided in SEQ ID NOS:1-4. For example in the previous paragraph, 1-7 hAmylin refers to the amino acid sequence from position 1 to position 7, inclusive, of human amylin (SEQ ID NO:1). Modification to the reference peptide may be shown as: position of modification adjacent to the modification. For example, (2Asp 7Lys) 1-7 hAmylin represents the amino acid sequence at positions 1 to 7 of human amylin with a modification of a Cys to Asp at position 2 and a modification of a Cys to Lys at position 7.

The α helix region of the novel compound may be about 8 to 23 amino acids in length. In certain embodiments, the α helix region is amphiphatic. In certain embodiments, the α helix region comprises about 3 to 6 helical turns. In certain embodiments, the α helix region comprises 3, 4, 5, or 6 helical turns. In other embodiments, the α helix region is a rigid structure equivalent to about 3, 4, 5, or 6 helical turns. An example of an idealized helix is LLQQLQKLLQKLKQY (SEQ ID NO:28). In certain embodiments, the α helix is an ampliphatic structure. Accordingly, characteristics of desirable amino acids that would provide this type of structure may be selected.

It has been found that the calcitonin α helix region, a combination of an amylin and a calcitonin α helix region, or parts thereof, and/or some CGRP elements are desirable in the α helix region of the novel compounds. It is contemplated that, as with the loop region, the α helix region can be from any amylin or calcitonin, and analogs thereof. Accordingly, in certain embodiments, the α helix region is at least a portion of an α helix region of calcitonin or calcitonin analog. In other embodiments, the α helix region is at least a portion of an α helix region of calcitonin or calcitonin analog and at least a portion of an α helix of an amylin or amylin analog. In still other embodiments, the α helix region of the novel compounds contain elements of CGRP. It is further contemplated that novel compounds may have no more than one, two, three, four, five, six, seven, eight, nine, or ten further modifications such as substitutions, insertions, deletions, and/or derivatizations.

In certain embodiments, the α helix region of the invention may comprise amino acids from position 8 of sCT to position 18, 19, 20, 21, 22, 23, 24, 25, 26, or 27 of sCT. Moreover, the α helix region may comprise more than one portion of a calcitonin or calcitonin analog α helix region of the same or different species, for example 8-21 sCT 19-27 sCT; 8-21 sCT 18-27 sCT; or 8-16 hCT 17-27 sCT; or (11Arg) 8-16 hCT (18Arg) 17-27 sCT. Alternatively or additionally, the above described α helix of 8-18 sCT to 8-27 sCT may further comprise the substitutions of one or more of (10Aib), (11Arg), (11Orn), (11hArg), (11Cit), (11hLys), (11Lys(for)), (17Aib), (18Arg), (18Orn), (18hArg), (18Cit), (18hLys), (18Lys(for)), (18Lys(PEG5000)), (22Leu), (24Pro) or any combination thereof.

In one embodiment, an α helix region of the invention can be represented by (α helix region type I) R1-VL Xaa10 Xaa11 LSQ Xaa15 L Xaa17 Xaa18 LQT Xaa22 P Xaa24 TNT-R1 (SEQ ID NO:29), wherein Xaa10 is Gly or Aib;

Xaa11 is Lys, Arg, Orn, hArg, Cit, hLys, or Lys(for);

Xaa15 is Glu or Phe;

Xaa17 is His or Aib;

Xaa18 is Lys, Arg, Orn, hArg, Cit, hLys, Lys(for), Lys (PEG 5000);

Xaa22 is Tyr or Leu;

Xaa24 is Arg or Pro; or

R1 is absent or comprises 1-4 additional amino acids.

Again, it should be remembered that each member of the Markush group, or a combination thereof, is another embodiment of the invention and is not to be read as a single unit. This is a shorthand method for stating, as an example, embodiments of the invention include an α helix region type I formula where, Xaa18 can be a Lys, Arg, Orn, hArg, Cit, hLys, or Lys(for), and each variation is a separate embodiment of the invention. Accordingly, the α helix region type I formula has one embodiment where Xaa18 is Lys. It has another embodiment where Xaa18 is Arg, and so on. It is further contemplated that the α helix region may contain no more than one, two, three, four, five, six, seven, eight, nine, or ten modifications such as substitutions, insertions, deletions, and/or derivatizations. Accordingly, the compounds of α helix region type I may have further deletions at the C-terminal end. In certain embodiments, the amino acids of R1 are capable of forming an α helix turn.

Examples of an α helix region type I of the invention include, but are not limited to 8-18 sCT, 8-21 sCT, 8-24 sCT, 8-27 sCT, (11Arg) 8-18 sCT, (18Arg) 8-18 sCT, (11Arg 18Arg) 8-18 sCT, (11Orn 18Orn) 8-18 sCT, (11Arg 18Cit) 8-18 sCT, (11hArg 18hArg) 8-18 sCT, (11Arg 18Orn) 8-18 sCT, (11Cit 18Arg) 8-18 sCT, (11Cit 18Cit) 8-18 sCT, (11hLys 18hLys) 8-18 sCT, (10Aib 11Arg 17Aib 18Arg) 8-18 sCT, (11Lys(for) 18Lys(for)) 8-18 sCT, (10Aib 11Lys (for) 17Aib 18Lys(for)) 8-18 sCT, (11Arg 18Lys(PEG 5000)) 8-18 sCT, (11Arg) 8-21 sCT, (18Arg) 8-21 sCT, (11Arg 18Arg) 8-21 sCT, (11Orn 18Orn) 8-21 sCT, (11Arg 18Cit) 8-21 sCT, (11hArg 18hArg) 8-21 sCT, (11Arg 18Orn) 8-21 sCT, (11Cit 18Arg) 8-21 sCT, (11Cit 18Cit) 8-21 sCT, (11hLys 18hLys) 8-21 sCT, (10Aib 11Arg 17Aib 18Arg) 8-21 sCT, (11Lys(for) 18Lys(for)) 8-21 sCT, (10Aib 11Lys (for) 17Aib 18Lys(for)) 8-21 sCT, (11Arg 18Lys(PEG 5000)) 8-21 sCT, (11Arg) 8-24 sCT, (18Arg) 8-24 sCT, (11Arg 18Arg) 8-24 sCT, (11Arg 18Arg 22Leu) 8-24 sCT, (11Arg 18Arg 24Pro) 8-24 sCT, (11Orn 18Orn) 8-24 sCT, (11Arg 18Cit) 8-24 sCT, (11hArg 18hArg) 8-24 sCT, (11Arg 18Orn) 8-24 sCT, (11Cit 18Arg) 8-24 sCT, (11Cit 18Cit) 8-24 sCT, (11hLys 18hLys) 8-24 sCT, (10Aib 11Arg 17Aib 18Arg) 8-24 sCT, (11Lys(for) 18Lys(for)) 8-24 sCT, (10Aib 11Lys (for) 17Aib 18Lys(for)) 8-24 sCT, (11Arg 18Lys(PEG 5000)) 8-24 sCT, (11Arg) 8-27 sCT, (18Arg) 8-27 sCT, (11Arg 18Arg) 8-27 sCT, (11Arg 18Arg 22Leu) 8-27 sCT, (11Arg 18Arg 24Pro) 8-27 sCT, (11Orn 18Orn) 8-27 sCT, (11Arg 18Cit) 8-27 sCT, (11hArg 18hArg) 8-27 sCT, (11Arg 18Orn) 8-27 sCT, (11Cit 18Arg) 8-27 sCT, (11Cit 18Cit) 8-27 sCT, (11hLys 18hLys) 8-27 sCT, (10Aib 11Arg 17Aib 18Arg) 8-27 sCT, (11Lys(for) 18Lys(for)) 8-27 sCT, (10Aib 11Lys (for) 17Aib 18Lys(for)) 8-27 sCT, (11Arg 18Lys(PEG 5000)) 8-27 sCT, (11Arg 18Arg) 8-21 sCT-19-27 sCT, and (11Arg 18Arg) 8-21 sCT-(18Leu) 18-27 sCT.

In certain embodiments, the α helix region of the invention may comprise a portion of an α helix region of amylin or amylin analog and a portion of an α helix region of calcitonin or calcitonin analog. The α helix region of the invention may comprise amino acids from position 8 of hAmylin to 11, 12, 13, 14, 15, 16, 17, 18 or 19 of hAmylin and amino acids from position 13, 14, 15, 16, 17, 18, and 19 of sCT to position 18, 19, 20, 21, 22, 23, 24, 25, 26, or 27 of sCT. Alternatively or additionally, the above described α helix region of amylin and calcitonin may further comprise the substitutions of one or more of (8Val), (9Leu), (9Met), (10Gly), (10His), (12Thr), (13Thr), (13Asn), (13Phe), (13Tyr), (14Arg), (14Ala), (14Asp), (14Glu), (14Gln), (14Thr), (14Gly), (15Leu), (15Ser), (15Glu), (15Ala), (15Tyr), (16Asp), (17Ser), (17Phe), (18Arg), (17Aib), (18Arg), (18Orn), (18hArg), (18Cit), (18hLys), (18Lys(for)), (18Lys(PEG5000)), (19Phe), (20His), (21Asn), (22Met), (22Val), (22Phe), (22Leu), (24Pro), or any combination thereof. In certain embodiments, the number of amino acids in the α helix region of the invention is at least 10 amino acids. In other embodiments, the number of amino acids in the α helix region of the invention is 11, 12, 13, 14, 15, 16, 17, 18, 19, 20, 21, 22, or 23. In other embodiments, the number of amino acids in the α helix region of the invention is 24 or more.

In one embodiment, an α helix region of the invention can be represented by (α helix region type II) R1-Xaa8 Xaa9 Xaa10 R Xaa12 Xaa13 Xaa14 Xaa15 Xaa16 Xaa17 Xaa18 Xaa19 Xaa20 Xaa21 Xaa22 P Xaa24 TNT-R1 (SEQ ID NO:30) wherein
  Xaa8 is Ala or Val;
  Xaa9 is Thr, Met or Leu;
  Xaa10 is Gln, Gly, His;
  Xaa12 is Leu, or Thr;
  Xaa13 is Ala, Thr, Asn, Phe, Tyr, Ser, or Thr;
  Xaa14 is Asn, Arg, Ala, Asp, Glu, Gln, Thr, or Gly;
  Xaa15 is Phe, Leu, Ser, Glu, Ala, Asp, or Tyr;
  Xaa16 is Leu or Asp;
  Xaa17 is Val, His, Ser, Phe, or Aib;
  Xaa18 is His, Arg, Lys, Orn, hArg, Cit, hLys, Lys(for), or Lys(PEG5000);
  Xaa19 is Leu, Ser or Phe;
  Xaa20 is Gln or His;
  Xaa21 is Thr or Asn;
  Xaa22 is Tyr, Val, Phe, Leu or Met;
  Xaa24 is Arg or Pro; and
  R1 is absent or comprises 1-4 additional amino acids.

Again, it should be remembered that each member in the Markush group, or a combination thereof, is another embodiment of the invention and is not to be read as a single unit. It is further contemplated that the α helix region may contain no more than one, two, three, four, five, six, seven, eight, nine, or ten modifications such as substitutions, insertions, deletions, and/or derivatizations of the compounds described herein. For example, in certain embodiments, the compounds of α helix region type II may have deletions at the C-terminal end resulting in the deletion of position 27, 26, 25, 24, or 22. In other embodiments, however, the deletions do not remove amino acids of positions 19, 20, 21, or 22.

Examples of an α helix region of type II include, but is not limited to (8Val 9Leu 10Gly) 11-15 hAmylin 16-27 sCT, (8Val 9Leu 10Gly) 11-15 hAmylin (18Arg) 16-27 sCT, 8-12 hAmylin (18Arg) 13-27 sCT, 8-18 hAmylin 19-23 sCT, 8-18 hAmylin 19-27 sCT, (15Glu 18Arg) 8-18 hAmylin 19-24 sCT, (14Arg 15Ser) 8-18 hAmylin 19-22 sCT, (13Ala 14Ala 15Ala) 8-18 hAmylin 19-27 sCT, (13Ala 14Asp 15Ala) 8-18 hAmylin 19-22 sCT, (13Ala 14Asp) 8-18 hAmylin 19-23 sCT, (13Ala 14Asp) 8-18 hAmylin 19-27 sCT, (13Ala 14Ala) 8-18 hAmylin 19-22 sCT, (13Ala 14Glu) 8-18 hAmylin 19-22 sCT, (13Thr 14Asp 15Tyr) 8-18 hAmylin 19-22 sCT, (13Ala 14Gln) 8-18 hAmylin 19-22 sCT, (13Asn 14Glu 15Tyr) 8-18 hAmylin 19-27 sCT, (13Phe 14Asp) 8-18 hAmylin 19-27 sCT, (13Ala 14Asp) 8-18 hAmylin (15Glu 18Arg) 8-18 hAmylin 19-24 sCT, (19Phe 22Phe) 19-27 sCT, (13Ala 14Asp) 8-18 hAmylin (19Phe 20His 22Phe) 19-27 sCT, (13Ala 14Asp) 8-18 hAmylin (19Phe 22Phe) 19-27 sCT, (9Thr 10His) 8-18 hAmylin 19-22 sCT, (9Thr 10His 14Gly 15Leu 17Ser 18Arg) 8-19 hAmylin 20-23 sCT, 8-18 hAmylin (21Asn 22Phe 23Val) 19-23 sCT, 8-18 hAmylin (22Met) 19-27 sCT, 8-18 hAmylin (22Val) 19-27 sCT, (9Met 12Thr 13Tyr 14Thr 15Glu 16Asp 17Phe) 8-17 hAmylin (18Arg) 18-20 sCT). In other embodiments, novel compounds include variations of the above exemplary compounds with the α helix terminating at corresponding to 22, 23, 24, 25, 26 or 27 of sCT. In other words, compound 8-18 hAmylin 19-24 sCT is also specifically described as this compound is merely 8-18 hAmylin 19-27 sCT described above truncated to position 24. As another example, compound (13Ala 14Asp 15Ala) 8-18 hAmylin 19-23 is specifically described because of the above language applied to (13Ala 14Asp 15Ala) 8-18 hAmylin 19-22.

In certain embodiments, the C-terminal tail of the invention comprises amino acids from position 27, 28, 29, 30, 31, 32, or 33 to position 36 or 37 of hAmylin. In other embodiments, the C-terminal tail comprises amino acids from position 27 or 28 to position 32 of sCT; however, when the loop region is from a calcitonin or calcitonin analog and the α helix region is from a calcitonin or calcitonin analog, the last position of the C-terminal tail is not Pro, Hyp, homoSerine (Hse) or derivatives of Hse. Alternatively or additionally, the above described α helix of amylin and calcitonin may further comprise the substitutions of one or more of (27Tyr) hAmylin, (29Arg) hAmylin, (32Val) hAmylin, (32Thr) hAmylin, (34Glu) hAmylin, (35Lys) hAmylin, (36Phe) hAmylin, (36Ala) hAmylin, (37Phe) hAmylin, (30Asn)sCT, (32Tyr) sCT, or any combination thereof.

In one embodiment, a C-terminal tail of the invention can be represented by Xaa28 Xaa29 Xaa30 Xaa31 Xaa32 Xaa33 G Xaa35 Xaa36 Xaa37 Xaa38 (SEQ ID NO:31), wherein
  Xaa28 is Lys, Tyr, or absent;
  Xaa29 is Ser, Pro, or absent;

Xaa30 is Ser, Pro, Arg, or absent;
Xaa31 is Thr, or absent;
Xaa32 is Asn or absent;
Xaa33 is Val, Thr, or absent;
Xaa35 is Ser, Glu
Xaa36 is Asn, Lys, or Gly;
Xaa37 is Thr, Phe, or Ala;
Xaa38 is Tyr, Phe, Pro, or absent;
with the proviso that when the loop region is from a calcitonin or calcitonin analog and the α helix region is from a calcitonin or calcitonin analog, the last position of the C-terminal tail is not Pro, Hyp, homoSerine (Hse) or derivatives of Hse.

Again, it should be remembered that each member of the Markush group, or a combination thereof, is another embodiment of the invention and is not to be read as a single unit. It is further contemplated that the C-terminal tail may contain no more than one, two, or three modifications such as substitutions, insertions, deletions, and/or derivatizations of the compounds described in the previous paragraphs.

Examples of the C-terminal tail of the invention include, but is not limited to, 27-37 rAmylin, (27Tyr 29Arg 32Thr) 27-37 rAmylin, (29Arg 32Thr) 28-37 rAmylin, 30-37 hAmylin, (32Thr) 30-37 hAmylin, (35Lys 36Ala 37Phe) 30-37 hAmylin, 30-36 hAmylin, (32Val) 30-36 hAmylin, (34Glu 36Phe) 30-36 hAmylin, 31-37 hAmylin, 31-36 hAmylin, 33-36 hAmylin, 33-7 hAmylin, 28-32 sCT, (30Asn 32Tyr) 28-32 sCT, and 27-32 sCT. In other embodiments, the C-terminal tail comprises the amino acid sequence KSNFVPTN (SEQ ID NO:32) or SNFVPTNV (SEQ ID NO:33).

It is further contemplated that no more than one, two, or three modifications such as substitutions, insertions, deletions, and/or derivatizations may be made to the C-terminal tail of the invention as described in the preceding paragraphs. The C-terminal tail of the novel compounds may further comprise modifications or additional amino acids at the C-terminal end. Such modifications include the addition of compounds such as Lys, up to 4 Lys, L-Octylglycine, 4ABU (4-Aminobutyric acid), 9Anc (9-Amiononanoic acid), and/or groups for solubility, stability, or delivery. Examples include 33-37 hAmylin L-octylglycine, 33-37 hAmylin 4ABU, and 33-37 hAmylin 9Anc.

In a general aspect, compounds of the invention comprise
(a) any of the loop region of the invention;
(b) any α helix region of the invention; and
(c) any C-terminal tail of the invention, with the proviso that when the loop region is from a calcitonin or calcitonin analog and the α helix region is from a calcitonin or calcitonin analog, the last position of the C-terminal tail is not Pro, Hyp, homoSerine (Hse) or derivatives of Hse.

In another general aspect, compounds of the invention comprise
(a) a loop region comprising Xaa1 or Xaa1 with modifications at the N-terminal end;
(b) an α helix region comprising the α helix region type I or type II;
(c) a C-terminal tail represented by SEQ ID NO:31, with the proviso that when the loop region is from a calcitonin or calcitonin analog and the α helix region is from a calcitonin or calcitonin analog, the last position of the C-terminal tail is not Pro, Hyp, homoSerine (Hse) or derivatives of Hse. The C-terminal end may comprise further modifications.

In yet another aspect, compounds of the invention comprise an amino acid sequence of formula I Xaa1 X Xaa3 Xaa4 Xaa5 Xaa6 Y Xaa8 Xaa9 Xaa10 Xaa11 Xaa12 Xaa13 Xaa14 Xaa15 Xaa16 Xaa17 Xaa18 Xaa19 Xaa20 Xaa21 Xaa22 Xaa23 Xaa24 Xaa25 Xaa26 Xaa27 Xaa28 Xaa29 Xaa30 Xaa31 Xaa32 (SEQ ID NO:34) wherein Xaa1 is A, C, hC, D, E, F, I, L, K, hK, R, hR, S, Hse(homoSER), T, G, Q, N, M, Y, W, P,
Hyp (hydroxyProline), H, V or absent;
Xaa3 is A, D, E, N, Q, G, V, R, K, hK, hR, H, I, L, M, or absent;
Xaa4 is A, I, L, S, Hse, T, V, M, or absent;
Xaa5 is A, S, T, Hse, Y, V, I, L, or M;
Xaa6 is T, A, S, Hse, Y, V, I, L, or M;
Xaa8 is A, V, I, L, F, or M;
Xaa9 is L, T, S, Hse, V, I, or M;
Xaa10 is G, H, Q, K, R, N, hK, or hR;
Xaa11 is K, R, Q, N, hK, hR, or H;
Xaa12 is L, I, V, F, M, W, or Y;
Xaa13 is A, F, Y, N, Q, S, Hse, or T;
Xaa14 is A, D, E, G, N, K, Q, R, H, hR, or hK;
Xaa15 is A, D, E, F, L, S, Y, I, V, or M;
Xaa16 is L, F, M, V, Y, or I;
Xaa17 is H, Q, N, S, Hse, T, or V;
Xaa18 is K, hK, R, hR, H, u (Cit), or n (Orn);
Xaa19 is F, L, S, Hse, V, I, T, or absent;
Xaa20 is H, R, K, hR, hK, N, Q, or absent;
Xaa21 is T, S, Hse, V, I, L, Q, N, or absent;
Xaa22 is F, L, M, V, Y, or I;
Xaa23 is P or Hyp;
Xaa24 is P, Hyp, R, K, hR, hK, or H;
Xaa25 is T, S, Hse, V, I, L, F, or Y;
Xaa26 is N, Q, D, or E;
Xaa27 is T, V, S, F, I, or L;
Xaa28 is G or A;
Xaa29 is S, Hse, T, V, I, L, or Y;
Xaa30 is E, G, K, N, D, R, hR, hK, H, or Q;
Xaa31 is A, T, S, Hse, V, I, L, F, or Y; and
Xaa32 is F, P, Y, Hse, S, T, or Hyp;
wherein X and Y are capable of creating a bond and are independently selected residues having side chains which are chemically bonded to each other to form an intramolecular linkage such as disulfide bonds; amide bond; alkyl acids and alkyl amines which may form cyclic lactams; alkyl aldehydes or alkyl halides and alkylamines which may condensed and be reduced to form an alkyl amine or imine bridge; or side chains which may be connected to form an alkyl, alkenyl, alkynyl, ether or thioether bond. Alkyl chains may include lower alkyl groups having from about 1 to about 6 carbon atoms. In certain embodiments, the intramolecular linkage may be a disulfide, amide, imine, amine, alkyl and alkene bond. In certain embodiments, X and Y are independently selected from Ser, Asp, Glu, Lys, Orn, or Cys. In certain embodiments, X and Y are Cys and Cys. In other embodiments, X and Y are Ser and Ser. In still other embodiments, X and Y are Asp and Lys or Lys and Asp.

In yet another aspect, compounds of the invention comprise an amino acid sequence of formula II: Xaa1 Xaa2 Xaa3 Xaa4 Xaa5 Xaa6 Xaa7 Xaa8 Xaa9 Xaa10 Xaa11 Xaa12 Xaa13 Xaa14 Xaa15 Xaa16 Xaa17 Xaa18 Xaa19 Xaa20 Xaa21 Xaa22 Xaa23 Xaa24 Xaa25 Xaa26 Xaa27 Xaa28 Xaa29 Xaa30 Xaa31 Xaa32 (SEQ ID NO:35) wherein
Xaa1 is A, C, D, F, I, K, S, T, or absent;
Xaa2 is C, D, S, or absent;
Xaa3 is A, D, N, or absent;
Xaa4 is A, L, T, or absent;
Xaa5 is A or S;
Xaa6 is T, A, S, or V;
Xaa7 is C, K, or A;
Xaa8 is A, V, L, or M;
Xaa9 is L or T;
Xaa10 is G, H, or Q;
Xaa11 is K, R, Q, or hArg;
Xaa12 is L, W, or Y;

Xaa13 is A, F, N, Q, S, or T;
Xaa14 is A, D, E, G, N, K, Q, or R;
Xaa15 is A, D, E, F, L, S, or Y;
Xaa16 is L, or F;
Xaa17 is H, Q, S, or V;
Xaa18 is K, R, hArg, u (Cit), or n (Orn);
Xaa19 is F, L, S, or absent;
Xaa20 is H, Q, or absent;
Xaa21 is T, N, or absent;
Xaa22 is F, L, M, V, or Y;
Xaa23 is P;
Xaa24 is P or R;
Xaa25 is T;
Xaa26 is N;
Xaa27 is T or V;
Xaa28 is G;
Xaa29 is S;
Xaa30 is E, G, K, or N;
Xaa31 is A or T; and
Xaa32 is F, P, or Y.

In yet another aspect, compounds of the invention comprise an amino acid sequence of formula III: Xaa1 Xaa2 Xaa3 Xaa4 Xaa5 Xaa6 Xaa7 Xaa8 Xaa9 Xaa10 Xaa11 Xaa12 Xaa13 Xaa14 Xaa15 Xaa16 Xaa17 Xaa18 Xaa19 Xaa20 Xaa21 Xaa22 Xaa23 Xaa24 Xaa25 Xaa26 Xaa27 Xaa28 Xaa29 Xaa30 Xaa31 Xaa32, (SEQ ID NO:36) wherein
Xaa1 is A, C, F, I, K, S, or absent;
Xaa2 is C, D, or S;
Xaa3 is A, D or N;
Xaa4 is A, L or T;
Xaa5 is A or S;
Xaa6 is T;
Xaa7 is C or K;
Xaa8 is A or V;
Xaa9 is L or T;
Xaa10 is G, H, or Q;
Xaa11 is K, R, or hArg;
Xaa12 is L;
Xaa13 is A, F, N, S, or T;
Xaa14 is A, D, E, G, N, Q, or R;
Xaa15 is A, E, F, L, S, or Y;
Xaa16 is L;
Xaa17 is H, S, or V;
Xaa18 is K, R, hArg, u (Cit), or n (Orn);
Xaa19 is F, L, or S;
Xaa20 is H or Q;
Xaa21 is T or N;
Xaa22 is F, L, M, V, or Y;
Xaa23 is P;
Xaa24 is P or R;
Xaa25 is T;
Xaa26 is N;
Xaa27 is T, or V;
Xaa28 is G;
Xaa29 is S;
Xaa30 is E, G, K, or N;
Xaa31 is A, or T; and
Xaa32 is F, P, or Y.

In a general aspect, the sequence of formula I, II, or III further comprises 1, 2, 3, 4, 5, 6, 7, 8, 9, 10, 11, 12, or more modifications of substitutions, insertions, deletions, elongations and/or derivatizations. In certain embodiments, the sequence of formula I, II, or III comprises a Val is inserted between amino acids at positions 22 and 23. In other embodiments, the sequence of formula I, II, or II comprises a Gln is inserted between positions 22 and 23. In still other embodiments, the sequence of formula I, II, or III comprises a sequence of Gln-Thr-Tyr (SEQ ID NO:37) between positions 22 and 23. In yet other embodiments, the sequence of formula I, II, or III comprises a sequence of Leu-Gln-Thr-Tyr (SEQ ID NO:38) between positions 22 and 23. In another general aspect, the modifications of formula I, II, or III may be at the N-terminal end. In certain embodiments, the N-terminal portion of formula I, II, or III has an added octylglycine. In other embodiments, the N-terminal portion of formula I, II or III has an added isocap.

In yet another aspect, compounds of the invention comprise an amino acid sequence of formula IV: Xaa1 Xaa2 Xaa3 Xaa4 Xaa5 Xaa6 Xaa7 Xaa8 Xaa9 Xaa10 Xaa11 Xaa12 Xaa13 Xaa14 Xaa15 Xaa16 Xaa17 Xaa18 Xaa19 Xaa20 Xaa21 Xaa22 Xaa23 Xaa24 Xaa25 Xaa26 Xaa27 Xaa28 Xaa29 Xaa30 Xaa31 Xaa32 (SEQ ID NO:39) wherein
Xaa1 is A, C, D, F, K, T, or absent;
Xaa2 is A, C, D, S, or absent;
Xaa3 is A, D, N, or absent;
Xaa4 is A, L, T, or absent;
Xaa5 is A or S;
Xaa6 is A, S, T, or V;
Xaa7 is A, C, or K;
Xaa8 is A, L, M, or V;
Xaa9 is L or T;
Xaa10 is G, H, or Q;
Xaa11 is K, Q, or R;
Xaa12 is L, W, or Y;
Xaa13 is A, N, Q, S, or T;
Xaa14 is A, D, E, G, K, N, Q, or R;
Xaa15 is A, D, E, F, L, S, or Y;
Xaa16 is F or L;
Xaa17 is H, Q, S or V;
Xaa18 is K, or R;
Xaa19 is F, L, S, or absent;
Xaa20 is H, K, Q, or absent;
Xaa21 is Q, T, or absent;
Xaa22 is F, L, or Y;
Xaa23 is P;
Xaa24 is P or R;
Xaa25 is T;
Xaa26 is N;
Xaa27 is T or V;
Xaa28 is G;
Xaa29 is S;
Xaa30 is E, K or N;
Xaa31 is A or T;
Xaa32 is F, Y, or absent;

In a general aspect, the sequence of formula IV further comprises 1, 2, 3, 4, 5, 6, 7, 8, 9, 10, 11, 12, or more modifications of substitutions, insertions, deletions, elongations and/or derivatizations. In certain embodiments, the sequence of formula I, II, III, or IV comprises a deletion at position 24.

In yet another aspect, compounds of the invention comprise an amino acid sequence comprising
a) a loop region comprising Xaa1;
b) an α helix loop type I; and
c) a C-terminal tail;
wherein X1 comprises an amino sequence of X Xaa2 Xaa3 Xaa4 Xaa5 Xaa6 Xaa7 Y (SEQ ID NO:138) wherein,
Xaa2 is any amino acid or absent;
Xaa3 is Ala, Gly, Ser, Asp or absent;
Xaa4 is Asn, Ala, Asp, Gly or absent;
Xaa5 is Ala, Leu, Thr, or Ser;
Xaa6 is Ala, Ser, or Thr; and
Xaa7 is Ala, Ser, Val, Hse, (S)-2-amio-3-hydroxy-methylbutanoic acid (Ahb), (2S,3R)-2-amino-3hydroxy-methylpentanoic acid (Ahp), D-Thr, Thr, or a derivative thereof;

X and Y are amino acids capable of creating a bond and are independently selected residues having side chains which are chemically bonded to each other to form an intramolecular linkage such as disulfide bonds; amide bond; alkyl acids and alkyl amines which may form cyclic lactams; alkyl aldehydes or alkyl halides and alkylamines which may condensed and be reduced to form an alkyl amine or imine bridge; or side chains which may be connected to form an alkyl, alkenyl, alkynyl, ether or thioether bond;

the α helical region type I comprises the sequence R1-V L Xaa10 Xaa11 L S Q Xaa15 L Xaa17 Xaa18 L Q T Xaa22 P Xaa24 T N T-R1 (SEQ ID NO:29), wherein
Xaa10 is Gly or Aib;
Xaa11 is Lys, Arg, Orn, hArg, Cit, hLys, or Lys(for);
Xaa15 is Glu or Phe;
Xaa17 is His or Aib;
Xaa18 is Lys, Arg, Orn, hArg, Cit, hLys, Lys(for), Lys (PEG 5000);
Xaa22 is Tyr or Leu;
Xaa24 is Arg or Pro; or
R1 is absent or comprises 1-4 additional amino acids; and
the C-terminal tail comprises the sequence Xaa28 Xaa29 Xaa30 Xaa31 Xaa32 Xaa33 G Xaa35 Xaa36 Xaa37 Xaa38 (SEQ ID NO:31), wherein
Xaa28 is Lys, Tyr, or absent;
Xaa29 is Ser, Pro, or absent;
Xaa30 is Ser, Pro, Arg, or absent;
Xaa31 is Thr, or absent;
Xaa32 is Asn or absent;
Xaa33 is Val, Thr, or absent;
Xaa35 is Ser, Glu
Xaa36 is Asn, Lys, or Gly;
Xaa37 is Thr, Phe, or Ala;
Xaa38 is Tyr, Phe, Pro, or absent;
with the proviso that when the loop region is from a calcitonin or calcitonin analog and the α helix region is from a calcitonin or calcitonin analog, the last position of the C-terminal tail is not Pro, Hyp, homoSerine (Hse) or derivatives of Hse.

In yet another aspect, compounds of the invention comprise an amino acid sequence comprising
a) a loop region comprising Xaa1;
b) an α helix loop type II; and
c) a C-terminal tail;
wherein loop region Xaa1 comprises an amino sequence of X Xaa2 Xaa3 Xaa4 Xaa5 Xaa6 Xaa7 Y wherein,
Xaa2 is any amino acid or absent;
Xaa3 is Ala, Gly, Ser, Asp or absent;
Xaa4 is Asn, Ala, Asp, Gly or absent;
Xaa5 is Ala, Leu, Thr, or Ser;
Xaa6 is Ala, Ser, or Thr; and
Xaa7 is Ala, Ser, Val, Hse, (S)-2-amio-3-hydroxy-methylbutanoic acid (Ahb), (2S,3R)-2-amino-3hydroxy-methylpentanoic acid (Ahp), D-Thr, Thr, or a derivative thereof;
X and Y are amino acids capable of creating a bond and are independently selected residues having side chains which are chemically bonded to each other to form an intramolecular linkage such as disulfide bonds; amide bond; alkyl acids and alkyl amines which may form cyclic lactams; alkyl aldehydes or alkyl halides and alkylamines which may condensed and be reduced to form an alkyl amine or imine bridge; or side chains which may be connected to form an alkyl, alkenyl, alkynyl, ether or thioether bond;

the α helical region type II comprises the sequence R1-Xaa8 Xaa9 Xaa10 R Xaa12 Xaa13 Xaa14 Xaa15 Xaa16 Xaa17 Xaa18 Xaa19 Xaa20 Xaa21 Xaa22 P Xaa24 TNT-R1 (SEQ ID NO:30) wherein
Xaa8 is Ala or Val;
Xaa9 is Thr, Met or Leu;
Xaa10 is Gln, Gly, His;
Xaa12 is Leu, or Thr;
Xaa13 is Ala, Thr, Asn, Phe, Tyr, Ser, or Thr;
Xaa14 is Asn, Arg, Ala, Asp, Glu, Gln, Thr, or Gly;
Xaa15 is Phe, Leu, Ser, Glu, Ala, Asp, or Tyr;
Xaa16 is Leu or Asp;
Xaa17 is Val, His, Ser, Phe, or Aib;
Xaa18 is His, Arg, Lys, Orn, hArg, Cit, hLys, Lys(for), or Lys(PEG5000);
Xaa19 is Leu, Ser or Phe;
Xaa20 is Gln or His;
Xaa21 is Thr or Asn;
Xaa22 is Tyr, Val, Phe, Leu or Met;
Xaa24 is Arg or Pro; and
R1 is absent or comprises 1-4 additional amino acids; and
the C-terminal tail comprises the sequence Xaa28 Xaa29 Xaa30 Xaa31 Xaa32 Xaa33 G Xaa35 Xaa36 Xaa37 Xaa38 (SEQ ID NO:31), wherein
Xaa28 is Lys, Tyr, or absent;
Xaa29 is Ser, Pro, or absent;
Xaa30 is Ser, Pro, Arg, or absent;
Xaa31 is Thr, or absent;
Xaa32 is Asn or absent;
Xaa33 is Val, Thr, or absent;
Xaa35 is Ser, Glu
Xaa36 is Asn, Lys, or Gly;
Xaa37 is Thr, Phe, or Ala;
Xaa38 is Tyr, Phe, Pro, or absent.

In still another aspect, compounds of the invention include:

```
KCNTATCVLGKLSQELHRLQTYPRTNTGSNTY            SEQ ID NO: 40

KCNTATCVLGRLSQELHRLQTLPRTNTGSNTY            SEQ ID NO: 41

KCNTATCVLGRLSQELHRLQTYPPTNTGSNTY            SEQ ID NO: 42

KCNTATCVLGRLSQELHRLQTYPRTNVGSNTY            SEQ ID NO: 43

KCNTATCVLGRLSQELHRLQTLPPTNVGSNTY            SEQ ID NO: 44

KCNTATCVLGRLANFLHRLQTYPRTNTGSNTY            SEQ ID NO: 45
```

-continued

SEQ ID NO: 46
ACNTATCVLGRLSQELHRLQTYPRTNTGSNTY

SEQ ID NO: 47
KCNAATCVLGRLSQELHRLQTYPRTNTGSNTY

SEQ ID NO: 48
KCNTAACVLGRLSQELHRLQTYPRTNTGSNTY

SEQ ID NO: 49
CANLSTCVLGRLSQELHRLQTYPRTNTGSNTY

SEQ ID NO: 50
isocaproyl-STAVLGRLSQELHRLQTYPRTNTGSNTY

SEQ ID NO: 51
CSNASTCVLGRLSQELHRLQTYPRTNTGSNTY

SEQ ID NO: 52
CSNLATCVLGRLSQELHRLQTYPRTNTGSNTY

SEQ ID NO: 53
CSNLSACVLGRLSQELHRLQTYPRTNTGSNTY

SEQ ID NO: 54
KCNTATCVLGRLSQELHKLQTYPRTNTGSNTY

SEQ ID NO: 55
KCNTATCVLGRLSQELHRLQTYPRTNTGSGTP

SEQ ID NO: 56
CSALSTCVLGRLSQELHRLQTYPRTNTGSNTY

SEQ ID NO: 57
Ac-(Agy)SNLST(Agy)VLGRLSQELHRLQTYPRTNTGSNTY

SEQ ID NO: 58
Ac-K(Agy)NTAT(Agy)VLGRLSQELHRLQTYPRTNTGSNTY

SEQ ID NO: 59
Isocaproyl-STAVL(Aib)RLSQELRLQTYPRTNTGSGTP

SEQ ID NO: 60
Isocaproyl-STAVLG[K(For)]LSQELH[K(For)]LQTYPRTNTGSGTP

SEQ ID NO: 61
Isocaproyl-STAVL(Aib)[K(For)]LSQEL(Aib)[K(For)]LQTYPRTNTGSNTY

SEQ ID NO: 62
Isocaproyl-STAVL(Aib)[K(For)]LSQEL(Aib)[K(For)]LQTYPRTNVGSNTY

SEQ ID NO: 63
KCNTATCLLQQLQKLLQKLKQYPRTNTGSNTY

SEQ ID NO: 64
KCNTASCVLGRLSQELHRLQTYPRTNTGSNTY

SEQ ID NO: 65
KCNTAVCVLGRLSQELHRLQTYPRTNTGSNTY

SEQ ID NO: 66
KCNTATCVLGRLSQELHRYPRTNTGSNTY

SEQ ID NO: 67
KCNTATCVLGK(For)LSQELHK(For)LQTYPRTNTGSNTY

SEQ ID NO: 68
KCNTA(d-Thr)CVLGRLSQELHRLQTYPRTNTGSNTY

SEQ ID NO: 69
KCNTA(dAh)CVLGRLSQELHRLQTYPRTNTGSNTY

SEQ ID NO: 70
Ac-ACNTATCVLGRLSQELHK(PEG5000)LQTYPRTNTGSNTY

SEQ ID NO: 71
KCNTATCVLGRLSQELHRLQTLQTYPRTNTGSNTY

SEQ ID NO: 72
KCNTATCVLGRLSQELHRLQTLLQTYPRTNTGSNTY

| | |
|---|---|
| KCNTATCVLGKLSQELHKLQTYPRTNTGSNTY | SEQ ID NO: 73 |
| KCNTSTCVLGRLSQELHRLQTYPRTNTGSNTY | SEQ ID NO: 74 |
| KCNTATCATQRLSQELHRLQTYPRTNTGSNTY | SEQ ID NO: 75 |
| KCNTATCATQRLSQELHRLQTYPRTNVGSNTY | SEQ ID NO: 76 |
| KCNTSTCATQRLANELVRLQTYPRTNVGSNTY | SEQ ID NO: 77 |
| KCNTA(Hse)CVLGRLSQELHRLQTYPRTNTGSNTY | SEQ ID NO: 78 |
| KCNTA(Ahb)CVLGRLSQELHRLQTYPRTNTGSNTY | SEQ ID NO: 79 |
| KCNTA(Ahp)CVLGRLSQELHRLQTYPRTNTGSNTY | SEQ ID NO: 80 |
| KCNTAT(OPO3H2)CVLGRLSQELHRLQTYPRTNTGSNTY | SEQ ID NO: 81 |
| KCNTATCVLG(Orn)LSQELH(Orn)LQTYPRTNTGSNTY | SEQ ID NO: 82 |
| KCNTATCVLG(Cit)LSQELH(Cit)LQTYPRTNTGSNTY | SEQ ID NO: 83 |
| KCNTATCVLG(homoK)LSQELH(homoK)LQTYPRTNTGSNTY | SEQ ID NO: 84 |
| L-OctylglycineKCNTATCVLGRLSQELHRLQTYPRTNTGSNTY | SEQ ID NO: 85 |
| N-3,6-dioxaoctanoyl-CNTATCVLGRLSQELHRLQTVPRTNTGSNTY | SEQ ID NO: 86 |
| KCNTATCMLGRYTQDFHRLQTYPRTNTGSNTY | SEQ ID NO: 87 |
| DSNLSTKVLGRLSQELHRLQTYPRTNTGSNTY | SEQ ID NO: 88 |
| KDNTATKVLGRLSQELHRLQTYPRTNTGSNTY | SEQ ID NO: 89 |
| CNTATCVLGRLSQELHRLQTYPRTNTGSNTY | SEQ ID NO: 90 |
| KCNTATCVLGRLSQELHRLQTYPRTNTGSNTY(9Anc) | SEQ ID NO: 91 |
| KCNTATCVLGRLSQELHRLQTYPRTNTGSNTY(L-octylglycine) | SEQ ID NO: 92 |
| N-isocaproyl-KCNTATCVLGRLSQELHRLQTYPRTNTGSNTY | SEQ ID NO: 93 |
| KCNTATCVLG(homoR)LSQELH(homoR)LQTYPRTNTGSNTY | SEQ ID NO: 94 |
| FCNTATCVLGRLSQELHRLQTYPRTNTGSNTY | SEQ ID NO: 95 |
| KCNTATCVLGRLSQELH(Cit)LQTYPRTNTGSNTY | SEQ ID NO: 96 |
| KCNTATCVLGRLSQELH(Orn)LQTYPRTNTGSNTY | SEQ ID NO: 97 |
| ICNTATCVLGRLSQELHRLQTYPRTNTGSNTY | SEQ ID NO: 98 |
| l-Octylglycine-CNTATCVLGRLSQELHRLQTYPRTNTGSNTY | SEQ ID NO: 99 |

-continued

| Sequence | SEQ ID NO |
|---|---|
| Isocaproyl-CNTATCVLGRLSQELHRLQTYPRTNTGSNTY | SEQ ID NO: 100 |
| KCNTATCVLG(Cit)LSQELHRLQTYPRTNTGSNTY | SEQ ID NO: 101 |
| KCNTATCVLGRLSQELHRLQTYPRTNTGSNTY(4ABU) | SEQ ID NO: 102 |
| Isocaproyl-KCNTATCVLGRLSQELHRLQTYPRTNTGSNTY(4ABU) | SEQ ID NO: 103 |
| KCNTSTCATQRLANELVRLQTYPRTNVGSEAF | SEQ ID NO: 104 |
| KCNTATCVLGRLSQELHRLQTYPTNVGSEAF | SEQ ID NO: 105 |
| KCNTATCVLGRLSRSLHRLQTYPRTNTGSNTY | SEQ ID NO: 106 |
| KCNTATCVTHRLSQELHRLQTYPRTNTGSNTY | SEQ ID NO: 107 |
| KCNTATCVLGRLADFLHRLQTYPRTNTGSNTY | SEQ ID NO: 108 |
| CNTATCVLGRLSQELHRLQTYPRTNTGSNT | SEQ ID NO: 109 |
| KCNTATCVLGRLSQELHRLQNFVPRTNTGSNTY | SEQ ID NO: 110 |
| KCNTATCVLGRLSQELHRLQTYPRTNTGSETF | SEQ ID NO: 111 |
| ACDTATCVLGRLSQELHRLQTYPRTNTGSNTY | SEQ ID NO: 112 |
| KCNTATCVLGRLSQELHRLQTYPRTNTGSKAF | SEQ ID NO: 113 |
| KCDTATCVTHRLAGLLSRSQTYPRTNTGSNTY | SEQ ID NO: 114 |
| KCNTATCVLGRLADALHRLQTYPRTNTGSNTY | SEQ ID NO: 115 |
| KCNTATCVLGRLAAFLHRLQTYPRTNTGSNTY | SEQ ID NO: 116 |
| SCNTATCVLGRLADFLHRLQTYPRTNTGSNTY | SEQ ID NO: 117 |
| KCNTATCVLGRLSQELHRLQTMPRTNTGSNTY | SEQ ID NO: 118 |
| KCNTATCVLGRLSQELHRLQTVPRTNTGSNTY | SEQ ID NO: 119 |
| KCNTATCVLGRLNEYLHRLQTYPRTNTGSNTY | SEQ ID NO: 120 |
| SCNTATCVLGRLSQELHRLQTYPRTNTGSNTY | SEQ ID NO: 121 |
| KCNTATCVLGRLTEFLHRLQTYPRTNTGSNTY | SEQ ID NO: 122 |
| KCNTATCVLGRLAEFLHRLQTYPRTNTGSNTY | SEQ ID NO: 123 |
| KCNTATCVLGRLTDYLHRLQTYPRTNTGSNTY | SEQ ID NO: 124 |
| KCNTATCVLGRLAQFLHRLQTYPRTNTGSNTY | SEQ ID NO: 125 |
| KCNTATCVLGRLADFLHRFQTFPRTNTGSNTY | SEQ ID NO: 126 |

KCNTATCVLGRLADFLHRFHTFPRTNTGSNTY                     SEQ ID NO: 127

KCNTATCVLGRLADFLHRFQTFPRTNTGSGTP                     SEQ ID NO: 128

CNTATCVLGRLADFLHRLQTYPRTNTGSNTY                      SEQ ID NO: 129

KCDTATCVLGRLSQELHRLQTYPRTNTGSNTY                     SEQ ID NO: 130

KCNTATCVLGRLFDFLHRLQTYPRTNTGSNTY                     SEQ ID NO: 131

KCNTATCVLGRLAAALHRLQTYPRTNTGSNTY                     SEQ ID NO: 132

TCDTATCVLGRLSQELHRLQTYPRTNTGSNTY                     SEQ ID NO: 133

CSNLSTCATQRLANELVRLQTYPRTNVGSNTY                     SEQ ID NO: 134

KCNTATCATQRLANELVRLQTYPRTNVGSNTY                     SEQ ID NO: 135

CSNLSTCVLGRLSQELHRLQTYPRTNTGSNTY                     SEQ ID NO: 136

KCNTATCVLGRLSQELHRLQTYPRTNTGSNTY                     SEQ ID NO: 137

In still another aspect, compounds of the invention include biologically active fragments of SEQ ID NOS:40 to 137. Biologically active fragments may comprise deletions of 1, 2, 3, 4, 5, 6, 7, 8, 9, 10, 11, 12, 13, 14, 15 or more amino acids. In certain embodiments, the amino acid sequences of SEQ ID NOs:40 to 137 comprise at least 1, 2, 3, 4, 5, 6, 7, 8, 9, 10 or more modifications such as substitutions, insertions, deletions, and/or derivatizations. In other embodiments, the amino acid sequences of SEQ ID NOs:40 to 137 has no more than 1, 2, 3, 4, 5, 6, 7, 8, 9, or 10 modifications such as substitutions, insertions, deletions, and/or derivatizations. In still another aspect of the invention, compounds of the invention include those having at least 75, 80, 85, 90, 95, or 97% amino acid sequence identity to any of SEQ ID NOS: 40 to 137. Percent identity is determined by analysis with the AlignX module in Vector NTI (Invitrogen; Carlsbad Calif.). It is intended that each percent identity described, or reference to biologically active fragments or modifications be applied to each SEQ ID NO: individually. For example, each embodiment described, fragments, modification, or % identity is applicable to SEQ ID NO:40, 41, 42, 43, 44, etc., or to any group of SEQ ID NOs:. Moreover, the compounds of the invention include the compounds 1-127 described in Example 3.

In another general aspect, compounds of the invention may act as an agonist for at least one biological effect of calcitonin, amylin, and/or CGRP herein disclosed or bind to at least one of the receptors of amylin, calcitonin, or CGRP.

In still another general aspect, the compounds of the invention may be useful for reducing food intake, reducing appetite, inducing satiety, reducing nutrient availability, causing weight loss, affecting body composition, altering body energy content or energy expenditure, improving lipid profile (including reducing LDL cholesterol and triglyceride levels and/or changing HDL cholesterol levels), slowing gastrointestinal motility, delay gastric emptying, moderating the postprandial blood glucose excursions, preventing or inhibiting glucagon secretion, and decreasing blood pressure.

Thus, in certain embodiments, the methods of the invention are useful for treating or preventing conditions or disorders which can be alleviated by reducing nutrient availability comprising administering to said subject a therapeutically or prophylactically effective amount of a compound of the invention. Such conditions and disorders include, but are not limited to, eating disorders, insulin-resistance, obesity, abnormal postprandial hyperglycemia, diabetes of any kind, including Type I, Type II, and gestational diabetes, Metabolic Syndrome, Dumping Syndrome, hypertension, dyslipidemia, cardiovascular disease, hyperlipidemia, sleep apnea, cancer, pulmonary hypertension, cholecystitis, and osteoarthritis.

Non-limiting examples of a cardiovascular condition or disease are hypertension, myocardial ischemia, and myocardial reperfusion. Compounds of the invention may also be useful in treating or preventing other conditions associated with obesity including stroke, cancer (e.g., endometrial, breast, prostate, and colon cancer), gallbladder disease, sleep apnea, reduced fertility, and osteoarthritis, (see Lyznicki et al, Am. Fam. Phys. 63:2185, 2001). In other embodiments, compounds of the invention may be used to alter body composition for aesthetic reasons, to enhance one's physical capabilities, or to produce a leaner meat source.

In another general aspect, compounds of the invention may be used to inhibit the secretion of ghrelin. Accordingly, compounds of the invention may be utilize this mechanism to treat or prevent ghrelin related disorders such as Prader-Willi syndrome, diabetes of all types and its complications, obesity, hyperphagia, hyperlipidemia, or other disorders associated with hypernutrition.

In another general aspect, it is now recognized that amylin and amylin agonists, including compounds of the invention, may be useful for treating or preventing Barrett's esophagus, Gastroesophageal Reflux Disease (GERD) and conditions associated therewith. Such conditions can include, but are not limited to, heartburn, heartburn accompanied by regurgitation of gastric/intestinal contents into the mouth or the lungs, difficulty in swallowing, coughing, intermittent wheezing and vocal cord inflammation (conditions associated with GERD), esophageal erosion, esophageal ulcer, esophageal stricture, Barrett's metaplasia (replacement of normal esophageal epithelium with abnormal epithelium), Barrett's adenocarcinoma, and pulmonary aspiration. Amylin and amylin agonists, including compounds of the invention, have antisecretory properties, such as inhibition of gastric acids, inhibition of bile acids, and inhibition of pancreatic enzymes. Moreover, amylin has been found to have a gastroprotective effect. Accordingly, these properties of amylin, amylin agonists and compounds of the invention may render them particularly useful in the treatment or prevention of Barrett's esophagus, and/or GERD and related or associated conditions as described herein.

In another general aspect, compounds of the invention may further be useful for treating or preventing pancreatitis, pancreatic carcinoma, and gastritis. Moreover, compounds of the invention may be useful in the treatment and prevention of pancreatitis in patients who have undergone endoscopic retrograde cholangiopancreatography (ERCP). It has further been discovered that amylin and amylin agonists, including compounds of the invention, may have a surprisingly superior therapeutic effect when combined with somatostatin. Accordingly, in certain embodiments, methods for treating or preventing pancreatitis comprise administering amylin, and amylin agonists, including compounds of the invention, and administering somatostatin and somatostatin agonists to a subject. In other embodiments, methods for treating or preventing pancreatitis comprise administering compounds of the invention and administering somatostatin and somatostatin agonists.

In another general aspect, compounds of the invention may also be useful for decreasing bone resorption, decreasing plasma calcium, and inducing an analgesic effect. Accordingly, compounds of the invention may be useful to treat bone disorder such as osteopenia and osteoporosis. In yet other embodiments, compounds of the invention may be useful to treat pain and painful neuropathy.

In still another general aspect, the compounds of the invention may be used as part of a combination therapy. In certain embodiments, compounds of the invention may be used with other commercially available diet aids or other anti-obesity agents, such as, by way of example, PYY and PYY agonists, GLP-1 and GLP-1 agonists, a DPPIV inhibitor, CCK and CCK agonists, exendin and exendin agonists, and leptin and leptin agonists. In other embodiments, compounds of the invention may be used with other analgesics, immune suppressors, or other anti-inflammatory agents.

In still another general aspect, novel pharmaceutical compositions comprising the compounds of the invention are described as well as methods for using them. In certain embodiments, pharmaceutical compositions may comprise at least 0.01% to 5% w/v. In certain embodiments, the pH of the composition can be from about 3.0 to about 6.0. In certain embodiments, the buffer may be acetate, phosphate, citrate, or glutamate. In certain embodiments, composition further comprises a carbohydrate or polyhydric alcohol tonicifier. In certain embodiments, the composition further comprises a preservative selected from the group consisting of m-cresol, benzyl alcohol, parabens and phenol. In still other embodiments, administration of the compounds in a dose in the range of about 0.05 mg/kg to about 2 mg/kg. For example, a daily dose may be 1 µg to about 5 mg per day. In certain embodiments, exemplary modes of delivery can be injection, infusion, absorption (mucosal), and inhalation. Routes of administration can be intramuscular, intravenous, subcutaneous, transdermal, transmucosal, oral, nasal, or by pulmonary inhalation.

Also contemplated as part of the invention are nucleotides that encode the amino acid sequence herein described, vectors containing the nucleotides, host cells for propagating nucleotides and/or expressing the polypeptides encoded by the nucleotides, antibodies directed to the novel compounds, and their uses in screening or detection/diagnosis of a condition such as those described herein in a subject.

These and other aspects of the invention will be more clearly understood with reference to the following preferred embodiments and detailed description.

BRIEF DESCRIPTION OF THE DRAWINGS

FIG. 2A illustrates a decreased caloric intake in fattened (diet-induced obese, or DIO) rats with continuous peripheral infusion of either a vehicle of exemplary compounds of the invention over a period of two weeks.

FIG. 2B illustrates a reduction in body weight over the corresponding time period.

FIG. 3 depicts effects on body composition by an exemplary compound of the invention.

FIG. 4A depicts effects on gastric emptying by an exemplary compound of the invention.

FIG. 4B depicts effect of hypocalcemia by an exemplary compound of the invention.

FIGS. 6A-6C depict the effect on triglycerides after 1 week (FIG. 6A), 2 weeks (FIG. 6B), and 3 weeks (FIG. 6C) by an exemplary compound (SEQ ID NO:137) of the invention.

FIGS. 7A-7E depict the dose effect on triglycerides at baseline (FIG. 7A) and after 2 weeks (FIG. 7B), 4 weeks (FIG. 7C), 6 weeks (FIG. 7D), and 8 weeks (FIG. 7E) by an exemplary compound (SEQ ID NO:137) of the invention.

FIG. 9A depicts the effect of plasma amylase, a marker on pancreatic function, by an exemplary compound (SEQ ID NO:137) of the invention.

FIG. 9B depicts the effect of plasma lipase, a marker on pancreatic function, by an exemplary compound (SEQ ID NO:137) of the invention.

FIG. 10A depicts the effect on gastric acid secretion by amylin.

FIG. 10B depicts the dose response effect on gastric acid secretion by amylin.

FIG. 11B depicts the gastric mucosal injury score of amylin.

FIG. 11C depicts the dose response curve of amylin.

DETAILED DESCRIPTION

Figure 1:
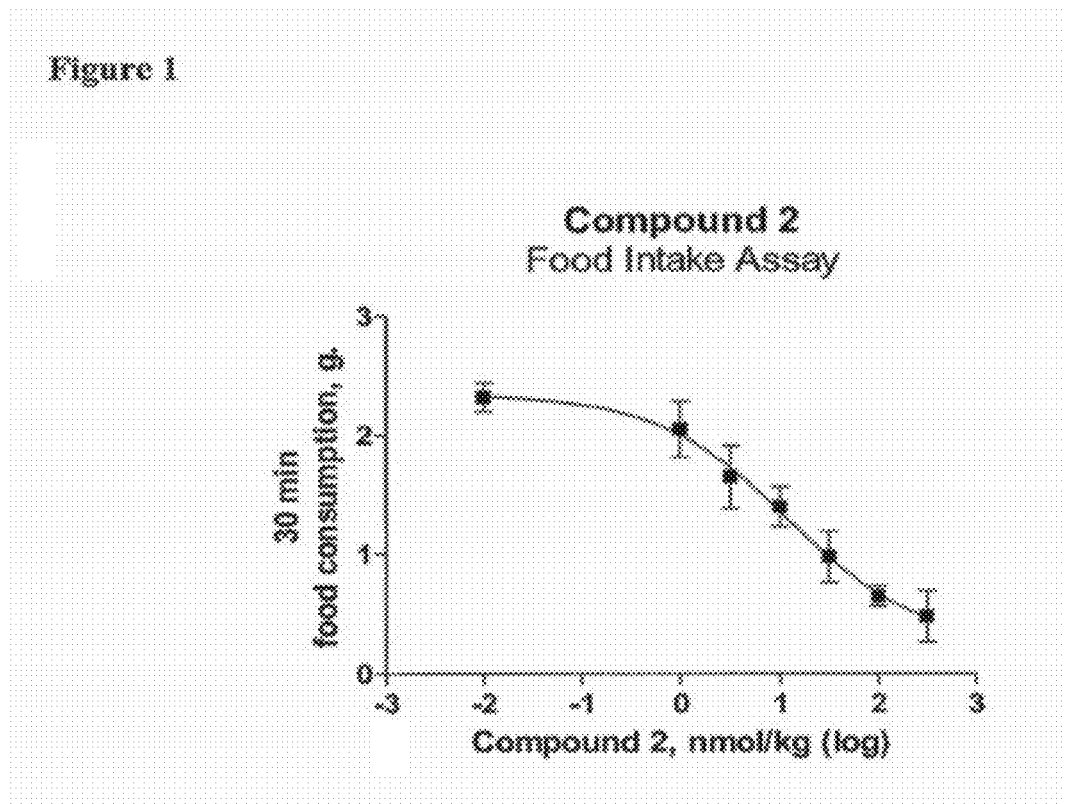
FIG. 1 demonstrates a dose-dependent reduction in food consumption in over night fasted mice to doses of an exemplary compound of the invention (Food Intake Assay).

The present invention relates to novel amylin family compounds or agonists (also referred to as novel compounds and compounds of the invention). These novel compounds may be useful in treating or preventing conditions such as metabolic disorders, vascular disorders, renal disorders, and/or gastrointestinal disorders. The previous section provides the structure of the compounds. The novel compounds may further be described as having desirable characteristic such as comparable or higher activity in the treatment and/or prevention of metabolic conditions and disorders and those referenced above, as compared to amylin, calcitonin, and/or CGRP. In other embodiments, the compounds of the invention may not have comparable or higher activity but may have increased stability or solubility, fewer side effects, combination of biological activities, quicker onset of activity, longer duration of activity, and/or ease in manufacturing, formulating, or use than amylin, calcitonin or CGRP.

By an amylin activity is meant that a compound demonstrates similar physiological characteristics as amylin, such as those described in the instant specification, for example, reducing food intake. The compounds of the present invention may be capable of binding to or otherwise directly or indirectly interacting with an amylin receptor, or other receptor or receptors with which amylin itself may interact to elicit a biological response, e.g., reducing food intake.

By a calcitonin activity is meant that a compound demonstrates similar physiological characteristics as calcitonin, such as those described in the instant specification, for example, inhibiting osteoclast function. The compounds of the present invention may be capable of binding to or otherwise directly or indirectly interacting with a CT receptor, or other receptor or receptors with which calcitonin itself may interact to elicit a biological response, e.g., inhibiting osteoclast function.

By a CGRP activity is meant that a compound demonstrates similar physiological characteristics as CGRP, such as those described in the instant specification, for example, eliciting a vasodilatory effect. The compounds of the present invention may be capable of binding to or otherwise directly or indirectly interacting with a CGRP receptor, or other receptor or receptors with which CGRP itself may interact to elicit a biological response, e.g., eliciting a vasodilatory effect.

The compounds of the invention may also include biologically active fragments of the larger peptides described herein that retain activity. Therefore, examples of desirable activities possessed by the compounds of the invention include (1) having activity in a food intake, gastric emptying, pancreatic secretion, blood pressure, heart rate or weight loss assay similar to amylin, calcitonin, or CGRP, and/or (2) binding in a receptor binding assay for amylin, calcitonin, or CGRP. Some exemplary assays are provided in Example 1.

Compounds of the invention may further have a particular binding profile. For example, it has been reported that the biological actions of amylin, calcitonin, and CGRP are mediated via binding to two closely related type II G protein-coupled receptors (GPCRs), the calcitonin receptor (CTR) and the calcitonin receptor like receptor (CRLR). Cloning and functional studies have shown that CGRP and amylin interact with different combinations of CTR or the CRLR and the receptor activity modifying protein (RAMP). Many cells express multiple RAMPs. It is believed that co-expression of RAMPs and either the CTR or CRLR is required to generate functional receptors for calcitonin, CGRP, and amylin. The RAMP family comprises three members (RAMP1, -2, and -3), which share less then 30% sequence identity, but have a common topological organization. Co-expression of CRLR and RAMP1 leads to the formation of a receptor for CGRP as does co-expression of CRLR and RAMP3. Co-expression of hCTR2 and RAMP1 leads to the formation of a receptor for amylin and CGRP. Co-expression of hCTR2 and RAMP3 leads to the formation of a receptor for amylin.

Accordingly, the compounds of the invention for use in the methods of the present invention may demonstrate affinity to receptors of amylin, CGRP, and calcitonin in the amylin family. Compounds of the invention may show a significant affinity for binding to the amylin receptor, as well as the ability to bind to other receptors such as calcitonin and CGRP receptors. Compounds of the invention may bind an amylin receptor with an affinity of greater than 20 nM, 10 nM, 5 nM, 1 nM, and more preferably with an affinity of greater than 0.10 nM. In addition, compounds of the present invention may also bind with similar affinities to the calcitonin and CGRP receptors, but with a lower affinity at the CGRP receptor. In other embodiments, compounds of the invention may bind to a calcitonin receptor with an affinity of greater than 20 nM, 10 nM, or 1 nM. In still other embodiments, compounds of the invention may bind to a CGRP receptor with an affinity of greater than about 1 µM, 700 nM, or 500 nM. Compounds of the invention may also bind to all three receptors to varying degrees. Accordingly, it is contemplated that compounds of the invention may have a binding profile with a particular binding affinity for each receptor from the ones described herein.

Compounds of the invention, including those of formula I, II, III, IV, biologically active fragments of SEQ ID NOS: 40 to 137, those having at least 75, 80, 82 85, 87, 90, 92, 95, or 97% amino acid sequence identity to any of SEQ ID NOS: 40 to 237, and biologically active fragments thereof may retain at least about 25%, preferably about 30%, 40%, 50%, 60%, 70%, 80%, 90%, 95%, 98%, or 99% percent of the biological activity of amylin, calcitonin, CGRP or compounds having the sequence of SEQ ID NOS:40 to 137, or Compounds 1-137 in Example 3, with respect to the reduction of food intake or one of the other activities described herein, e.g., Table 1. In another embodiment, compounds of the invention exhibit improved biological activity. Preferably, the novel compounds exhibit at least about 110%, 125%, 130%, 140%, 150%, 200%, or more of the biological activity of amylin, calcitonin, CGRP or the compounds having the sequence of SEQ ID NOS:40 to 137, or Compounds 1-137 in Example 3, with respect to the reduction of food intake or one of the other activities described herein, e.g, Table 1. For example, a desirable compound of the invention is one having an activity in one of the assays described herein (food intake, weight reduction assay, gastric emptying, triglycerides, pancreatitis, ghrelin, or calcium) which is greater than the activity of amylin, calcitonin, or CGRP in that same assay.

As illustration only, desirable compounds of the invention may demonstrate an ability to reduce cumulative food intake more than 5% over administration of the vehicle, preferably more than 15%, more preferably more than 25%, even more preferably more than 35% or 40% most preferably more than 50% over the vehicle.

In still another general aspect, the compounds of the invention may be useful for reducing food intake, reducing appetite, inducing satiety, reducing nutrient availability, causing weight loss, affecting body composition, altering body energy content or energy expenditure, improving lipid profile (including reducing LDL cholesterol and triglyceride levels and/or changing HDL cholesterol levels), slowing gastrointestinal motility, delay gastric emptying, moderating the postprandial blood glucose excursions, preventing or inhibiting glucagon secretion, and decreasing blood pressure. Exemplary assays for effects on food intake, weight reduction, gastric emptying, triglycerides, and body composition are described in at least Examples 3, 4, 5, 6, and 7.

Thus, in certain embodiments, the methods of the invention are useful for treating or preventing conditions or disorders which can be alleviated by reducing nutrient availability comprising administering to said subject a therapeutically or prophylactically effective amount of a compound of the invention. Such conditions and disorders include, but are not limited to, eating disorders, insulin-resistance, obesity, abnormal postprandial hyperglycemia, diabetes of any kind, including Type I, Type II, and gestational diabetes, Metabolic Syndrome, Dumping Syndrome, hypertension, dyslipidemia, cardiovascular disease, hyperlipidemia, sleep apnea, cancer, pulmonary hypertension, cholecystitis, and osteoarthritis.

Non-limiting examples of a cardiovascular condition or disease are hypertension, myocardial ischemia, and myocardial reperfusion. Compounds of the invention may also be useful in treating or preventing other conditions associated with obesity including stroke, cancer (e.g., endometrial, breast, prostate, and colon cancer), gallbladder disease, sleep apnea, reduced fertility, and osteoarthritis, (see Lyznicki et al, Am. Fam. Phys. 63:2185, 2001). In other embodiments, compounds of the invention may be used to alter body composition for aesthetic reasons, to enhance one's physical capabilities, or to produce a leaner meat source.

In another general aspect, compounds of the invention may be used to inhibit the secretion of ghrelin. Accordingly, compounds of the invention may be utilize this mechanism to treat or prevent ghrelin related disorders such as Prader-Willi syndrome, diabetes of all types and its complications, obesity, hyperphagia, hyperlipidemia, or other disorders associated with hypernutrition. An exemplary assay for effects on ghrelin is described in Example 8.

In another general aspect, it is now recognized that amylin and amylin agonists, including compounds of the invention, may be useful for treating or preventing Barrett's esophagus, Gastroesophageal Reflux Disease (GERD) and conditions associated therewith. Such conditions can include, but are not limited to, heartburn, heartburn accompanied by regurgitation of gastric/intestinal contents into the mouth or the lungs, difficulty in swallowing, coughing, intermittent wheezing and vocal cord inflammation (conditions associated with GERD), esophageal erosion, esophageal ulcer, esophageal stricture, Barrett's metaplasia (replacement of normal esophageal epithelium with abnormal epithelium), Barrett's adenocarcinoma, and pulmonary aspiration. Amylin and amylin agonists, including compounds of the invention, have antisecretory properties, such as inhibition of gastric acids, inhibition of bile acids, and inhibition of pancreatic enzymes. Accordingly, these properties of amylin, amylin agonists and compounds of the invention may render them particularly useful in the treatment or prevention of Barrett's esophagus, and/or GERD and related or associated conditions as described herein. Exemplary assays showing effects on gastric acid secretion and gastroprotective effect are described in Examples 10 and 11.

In another general aspect, compounds of the invention may further be useful for treating or preventing pancreatitis, pancreatic carcinoma, and gastritis. Moreover, compounds of the invention may be useful in the treatment and prevention of pancreatitis in patients who have undergone endoscopic retrograde cholangiopancreatography (ERCP). It has further been discovered that amylin and amylin agonists, including compounds of the invention, may have a surprisingly superior therapeutic effect when combined with somatostatin. Accordingly, in certain embodiments, methods for treating or preventing pancreatitis comprise administering amylin, and amylin agonists, including compounds of the invention, and administering somatostatin and somatostatin agonists to a subject. In other embodiments, methods for treating or preventing pancreatitis comprise administering compounds of the invention and administering somatostatin and somatostatin agonists. An exemplary assay showing effects on pancreatic function is described in Example 9.

In another general aspect, compounds of the invention may also be useful for decreasing bone resorption, decreasing plasma calcium, and inducing an analgesic effect. Accordingly, compounds of the invention may be useful to treat bone disorder such as osteopenia and osteoporosis. In yet other embodiments, compounds of the invention may be useful to treat pain and painful neuropathy. Exemplary assay showing effects on calcium levels are provided in Example 6.

In the methods of the present invention, the polypeptides may be administered separately or together with one or more other compounds and compositions that exhibit a long term or short-term action to reduce nutrient availability, including, but not limited to other compounds and compositions that comprise an amylin or amylin analog agonist, salmon calcitonin, a cholecystokinin (CCK) or CCK agonist, a leptin (OB protein) or leptin agonist, an exendin or exendin analog agonist, a GLP-1 or GLP-1 analog agonist, a DPPIV inhibitor, a PYY or PYY analog, AFP-6 (intermedin) or AFP-6 agonist, Urocortin or Urocortin agonist, or Adrenomedullin or Adrenomeullin agonist. Suitable amylin agonists include, for example, [25,28,29 Pro-]-human amylin (also known as "pramlintide," and described in U.S. Pat. Nos. 5,686,511 and 5,998,367). The CCK used is preferably CCK octopeptide (CCK-8). Leptin is discussed in, for example, (Pelleymounter, Cullen et al., Science 269: 540-543 (1995); Halaas, Gajiwala et al., Science 269: 543-6 (1995); Campfield, Smith et al., Science 269: 546-549 (1995)). Suitable exendins include exendin-3 and exendin-4, and exendin agonist compounds include, for example, those described in PCT Publications WO 99/07404, WO 99/25727, and WO 99/25728. Suitable PYY polypeptides and analogs include those described in U.S. Application Nos. 60/543,406 and 60/543,407.

While "obesity" is generally defined as a body mass index over 30, for purposes of this disclosure, any subject, including those with a body mass index of less than 30, who needs or wishes to reduce body weight is included in the scope of "obese."

Preparation of Compounds of the Invention

The compounds of the invention described herein may be prepared using standard recombinant techniques or chemical peptide synthesis techniques known in the art, e.g., using an automated or semi-automated peptide synthesizer, or both. Likewise, the derivatives of the polypeptides of the invention may be produced using standard chemical, biochemical, or in vivo methodologies.

The compounds of the invention can be synthesized in solution or on a solid support in accordance with conventional techniques. Various automatic synthesizers are commercially available and can be used in accordance with known protocols. See, e.g., Stewart and Young, Solid Phase Peptide Synthesis, 2d. ed., Pierce Chemical Co. (1984); Tam et al., J. Am. Chem. Soc. 105: 6442 (1983); Merrifield, Science 232: 341-7 (1986); and Barany and Merrifield, The Peptides, Gross and Meienhofer, eds., Academic Press, New York, 1-284 (1979). Solid phase peptide synthesis may be carried out with an automatic peptide synthesizer (e.g., Model 430A, Applied Biosystems Inc., Foster City, Calif.) using the NMP/HOBt (Option 1) system and tBoc or Fmoc chemistry (see, Applied Biosystems User's Manual for the ABI 430A Peptide Synthesizer, Version 1.3B Jul. 1, 1988, section 6, pp. 49-70, Applied Biosystems, Inc., Foster City, Calif.) with capping.

Peptides may also be assembled using an Advanced ChemTech Synthesizer (Model MPS 350, Louisville, Ky.). Peptides may be purified by RP-HPLC (preparative and analytical) using, e.g., a Waters Delta Prep 3000 system and a C4, C8, or C18 preparative column (10μ, 2.2×25 cm; Vydac, Hesperia, Calif.). The active protein can be readily synthesized and then screened in screening assays designed to identify reactive peptides.

Besides the classical step-by-step synthesis, convergent solid phase peptide synthesis (also known as hybrid approach or as fragment condensation method) has been developed for the preparation of complex and difficult peptides and small proteins. According to this method, suitably protected peptide fragments spanning the entire peptide sequence and prepared on the solid phase are condensed, either on solid support or in solution, to the target peptide. The availability of new resins and resin handles has opened up the possibility of synthesizing fully protected peptide segments rapidly by the solid-phase technique. The approach is particularly attractive for the manufacture of large molecules, since it combines the advantages of both the solid-phase and the solution-phase methods. Production cycle times are short, compared with solution-phase methodologies, and yields and purities are often higher. Additionally, the scale-up is a lot easier, and avoids many of the aggregation problems often encountered in solid-phase synthesis of long peptides.

In another embodiment, the synthetic strategy uses convergent fragment condensation. Convergent fragment condensation is a superior method of producing large, high quality peptides over standard solid or standard liquid phase synthesis. With such methods fragment can be synthesized in parallel cutting down on the time to synthesize as well as ensuring quality. As peptides grow longer, there is more risk of side reactions and incomplete synthesis. It has been recognized that peptide sequences of the invention can have ideally located Glycine and Proline which promote a fragment approach because those two amino acids are not able to racemize during fragment coupling and show very efficient condensation rates. Besides the fact that a straight forward solid phase synthesis presents major scale-up problems and is therefore probably not suitable for large scale synthesis, a fragment approach is much more controllable and provides the opportunity to purify intermediates. The disulfide bridge is located in the first fragment only and can therefore be formed at the fragment stage with the totally protected precursor. Since this approach presents a lot of advantages in terms of strategy and scale, it will shorten the synthesis time because all the fragments can be synthesized simultaneously. This is a great tool to minimize risk and to reduce costs. The following fragments are depicted to show a skeletal structure of desirable fragments where the would allow for implementation of this strategy:

Fragment 1: Boc-X (Boc)-X-X (Trt)-X (tBu)-X-X(tBu)-X-X-X-Gly-OH Cyclic (cyclization would take place prior to fragment coupling)

Fragment 2: Fmoc-K(Pbf)-X-X(tBu)-X(Trt)-X(OtBu)-X-X (Trt)-X(Pbf)-X-X(Trt)-X(tBu)-X(tBu)-Pro-OH Fragment 3: Fmoc-X(Pbf)-X(tBu)-X(Trt)-X(tBu)-X-X (tBu)-X(Trt)-Thr(tBu)-OH Fragment 4: H-Tyr(tBu)-$NH_2$ Based on these teaching it would understandable to one of skill in the art which compounds of the invention would be ideal for such synthesis. Evolving technology may make it possible to only have three fragments, i.e., the $4^{th}$ fragment need not be created separately from the $3^{rd}$.

The compounds of the present invention may alternatively be produced by recombinant techniques well known in the art. See, e.g., Sambrook et al., Molecular Cloning: A Laboratory Manual, 2d ed., Cold Spring Harbor (1989). These polypeptides produced by recombinant technologies may be expressed from a polynucleotide. These polynucleotide sequences may incorporate codons facilitating transcription and translation of mRNA in microbial hosts. Such manufacturing sequences may readily be constructed according to the methods well known in the art. See, e.g., WO 83/04053. The polynucleotides above may also optionally encode an N-terminal methionyl residue. Non-peptide compounds useful in the present invention may be prepared by art-known methods. For example, phosphate-containing amino acids and peptides containing such amino acids may be prepared using methods known in the art. See, e.g., Bartlett and Landen, Bioorg. Chem. 14: 356-77 (1986).

A variety of expression vector/host systems may be utilized to contain and express the coding sequence of the novel compounds. These include but are not limited to microorganisms such as bacteria transformed with recombinant bacteriophage, plasmid or cosmid DNA expression vectors; yeast transformed with yeast expression vectors; insect cell systems infected with virus expression vectors (e.g., baculovirus); plant cell systems transfected with virus expression vectors (e.g., cauliflower mosaic virus, CaMV; tobacco mosaic virus, TMV) or transformed with bacterial expression vectors (e.g., Ti or pBR322 plasmid); or animal cell systems. Mammalian cells that are useful in recombinant protein productions include but are not limited to VERO cells, HeLa cells, Chinese hamster ovary (CHO) cell lines, COS cells (such as COS-7), WI 38, BHK, HepG2, 3T3, RIN, MDCK, A549, PC12, K562 and 293 cells. Exemplary protocols for the recombinant expression of the protein are described herein below.

As such, polynucleotide sequences provided by the invention are useful in generating new and useful viral and plasmid DNA vectors, new and useful transformed and transfected procaryotic and eucaryotic host cells (including bacterial, yeast, and mammalian cells grown in culture), and new and useful methods for cultured growth of such host cells capable of expression of the present polypeptides. The polynucleotide sequences encoding the novel compounds herein may also be useful for gene therapy.

The present invention also provides for processes for recombinant DNA production of the novel compounds. Provided is a process for producing the polypeptides from a host cell containing nucleic acids encoding the novel compounds comprising: (a) culturing said host cell containing polynucleotides encoding such polypeptides under conditions facilitating the expression of such DNA molecule; and (b) obtaining the novel compounds.

Host cells may be prokaryotic or eukaryotic and include bacteria, mammalian cells (such as Chinese Hamster Ovary (CHO) cells, monkey cells, baby hamster kidney cells, cancer cells or other cells), yeast cells, and insect cells.

Mammalian host systems for the expression of the recombinant protein also are well known to those of skill in the art. Host cell strains may be chosen for a particular ability to process the expressed protein or produce certain post-translation modifications that will be useful in providing protein activity. Such modifications of the polypeptide include, but are not limited to, acetylation, carboxylation, glycosylation, phosphorylation, lipidation and acylation. Post-translational processing, which cleaves a “prepro” form of the protein, may also be important for correct insertion, folding and/or function. Different host cells, such as CHO, HeLa, MDCK, 293, WI38, and the like, have specific cellular machinery and characteristic mechanisms for such post-translational activities, and may be chosen to ensure the correct modification and processing of the introduced foreign protein.

Alternatively, a yeast system may be employed to generate the novel compounds of the invention. The coding region of the DNA encoding the novel compound is amplified by PCR. A DNA encoding the yeast pre-pro-alpha leader sequence is amplified from yeast genomic DNA in a PCR reaction using one primer containing nucleotides 1-20 of the alpha mating factor gene and another primer complementary to nucleotides 255-235 of this gene (Kurjan and Herskowitz, Cell, 30: 933-43 (1982)). The pre-pro-alpha leader coding sequence and the novel compound's coding sequence fragments are ligated into a plasmid containing the yeast alcohol dehydrogenase (ADH2) promoter, such that the promoter directs expression of a fusion protein consisting of the pre-pro-alpha factor fused to the mature novel compound. As taught by Rose and Broach, Meth. Enz. 185: 234-79, Goeddel ed., Academic Press, Inc., San Diego, Calif. (1990), the vector further includes an ADH2 transcription terminator downstream of the cloning site, the yeast "2-micron" replication origin, the yeast leu-2d gene, the yeast REP1 and REP2 genes, the *E. coli* β-lactamase gene, and an *E. coli* origin of replication. The β-lactamase and leu-2d genes provide for selection in bacteria and yeast, respectively. The leu-2d gene also facilitates increased copy number of the plasmid in yeast to induce higher levels of expression. The REP1 and REP2 genes encode proteins involved in regulation of the plasmid copy number.

The DNA construct described in the preceding paragraph is transformed into yeast cells using a known method, e.g., lithium acetate treatment (Steams et al., Meth. Enz. 185: 280-97 (1990)). The ADH2 promoter is induced upon exhaustion of glucose in the growth media (Price et al., Gene 55: 287 (1987)). The pre-pro-alpha sequence effects secretion of the fusion protein from the cells. Concomitantly, the yeast KEX2 protein cleaves the pre-pro sequence from the mature compounds of the invention (Bitter et al., Proc. Natl. Acad. Sci. USA 81: 5330-4 (1984)).

Compounds of the invention may also be recombinantly expressed in yeast using a commercially available expression system, e.g., the *Pichia* Expression System (Invitrogen, San Diego, Calif.), following the manufacturer's instructions. This system also relies on the pre-pro-alpha sequence to direct secretion, but transcription of the insert is driven by the alcohol oxidase (AOX1) promoter upon induction by methanol. The secreted novel compound is purified from the yeast growth medium by, e.g., the methods used to purify the novel compound from bacterial and mammalian cell supernatants.

Alternatively, the DNA encoding the novel compounds may be cloned into the baculovirus expression vector pVL1393 (PharMingen, San Diego, Calif.). This novel compound-containing vector is then used according to the manufacturer's directions (PharMingen) to infect *Spodoptera frugiperda* cells in sF9 protein-free media and to produce recombinant protein. The protein is purified and concentrated from the media using a heparin-Sepharose column (Pharmacia, Piscataway, N.J.) and sequential molecular sizing columns (Amicon, Beverly, Mass.), and resuspended in PBS. SDS-PAGE analysis shows a single band and confirms the size of the protein, and Edman sequencing on a Proton 2090 Peptide Sequencer confirms its N-terminal sequence.

For example, the DNA sequence encoding the desired novel compound may be cloned into a plasmid containing a desired promoter and, optionally, a leader sequence (see, e.g., Better et al., Science 240: 1041-3 (1988)). The sequence of this construct may be confirmed by automated sequencing. The plasmid is then transformed into *E. coli*, strain MC1061, using standard procedures employing $CaCl_2$ incubation and heat shock treatment of the bacteria (Sambrook et al., supra). The transformed bacteria are grown in LB medium supplemented with carbenicillin, and production of the expressed protein is induced by growth in a suitable medium. If present, the leader sequence will affect secretion of the mature novel compound and be cleaved during secretion. The secreted recombinant protein is purified from the bacterial culture media by the method described herein below.

Alternatively, the polypeptides of the present invention may be expressed in an insect system. Insect systems for protein expression are well known to those of skill in the art. In one such system, *Autographa californica* nuclear polyhedrosis virus (AcNPV) is used as a vector to express foreign genes in *Spodoptera frugiperda* cells or in *Trichoplusia larvae*. The novel compound's coding sequence is cloned into a nonessential region of the virus, such as the polyhedrin gene, and placed under control of the polyhedrin promoter. Successful insertion of the novel compound will render the polyhedrin gene inactive and produce recombinant virus lacking coat protein coat. The recombinant viruses are then used to infect *S. frugiperda* cells or *Trichoplusia larvae* in which the polypeptide is expressed (Smith et al., J. Virol. 46: 584 (1983); Engelhard et al., Proc. Natl. Acad. Sci. USA 91: 3224-7 (1994)).

In another example, the DNA sequence encoding the novel compound may be amplified by PCR and cloned into an appropriate vector, for example, pGEX-3X (Pharmacia, Piscataway, N.J.). The pGEX vector is designed to produce a fusion protein comprising glutathione-S-transferase (GST), encoded by the vector, and a protein encoded by a DNA fragment inserted into the vector's cloning site. The primers for the PCR may be generated to include, for example, an appropriate cleavage site. The recombinant fusion protein may then be cleaved from the GST portion of the fusion protein. The pGEX-3X/PYY analog polypeptide construct is transformed into *E. coli* XL-1 Blue cells (Stratagene, La Jolla, Calif.), and individual transformants are isolated and grown at 37° C. in LB medium (supplemented with carbenicillin) to an optical density at wavelength 600 nm of 0.4, followed by further incubation for 4 hours in the presence of 0.5 mM Isopropyl β-D-Thiogalactopyranoside (Sigma Chemical Co., St. Louis, Mo.). Plasmid DNA from individual transformants is purified and partially sequenced using an automated sequencer to confirm the presence of the desired gene insert in the proper orientation.

The fusion protein, expected to be produced as an insoluble inclusion body in the bacteria, may be purified as follows. Cells are harvested by centrifugation; washed in 0.15 M NaCl, 10 mM Tris, pH 8, 1 mM EDTA; and treated with 0.1 mg/mL lysozyme (Sigma Chemical Co.) for 15 min. at room temperature. The lysate is cleared by sonication, and cell debris is pelleted by centrifugation for 10 min. at 12,000×g. The fusion protein-containing pellet is resuspended in 50 mM Tris, pH 8, and 10 mM EDTA, layered over 50% glycerol, and centrifuged for 30 min. at 6000×g. The pellet is resuspended in standard phosphate buffered saline solution (PBS) free of $Mg^{++}$ and $Ca^{++}$. The fusion protein is further purified by fractionating the resuspended pellet in a denaturing SDS polyacrylamide gel (Sambrook et al., supra). The gel is soaked in 0.4 M KCl to visualize the protein, which is excised and electroeluted in gel-running buffer lacking SDS. If the GST/novel compound fusion protein is produced in bacteria as a soluble protein, it may be purified using the GST Purification Module (Pharmacia Biotech).

The fusion protein may be subjected to digestion to cleave the GST from the mature novel protein. The digestion reaction (20-40 μg fusion protein, 20-30 units human thrombin (4000 U/mg (Sigma) in 0.5 mL PBS) is incubated 16-48 hrs. at room temperature and loaded on a denaturing SDS-PAGE gel to fractionate the reaction products. The gel is soaked in 0.4 M KCl to visualize the protein bands. The identity of the protein band corresponding to the expected molecular weight of the novel compound may be confirmed by partial amino acid sequence analysis using an automated sequencer (Applied Biosystems Model 473A, Foster City, Calif.).

In a particularly preferred method of recombinant expression of the novel compounds, 293 cells may be co-transfected with plasmids containing the DNA of the novel compound in the pCMV vector (5' CMV promoter, 3' HGH poly A sequence) and pSV2neo (containing the neo resistance gene) by the calcium phosphate method. Preferably, the vectors should be linearized with ScaI prior to transfection. Similarly, an alternative construct using a similar pCMV vector with the neo gene incorporated can be used. Stable cell lines are selected from single cell clones by limiting dilution in growth media containing 0.5 mg/mL G418 (neomycin-like antibiotic) for 10-14 days. Cell lines are screened for expression of the novel compound by ELISA or Western blot, and high-expressing cell lines are expanded for large scale growth.

It is preferable that the transformed cells are used for long-term, high-yield protein production and as such stable expression is desirable. Once such cells are transformed with vectors that contain selectable markers along with the desired expression cassette, the cells may be allowed to grow for 1-2 days in an enriched media before they are switched to selective media. The selectable marker is designed to confer resistance to selection, and its presence allows growth and recovery of cells that successfully express the introduced sequences. Resistant clumps of stably transformed cells can be proliferated using tissue culture techniques appropriate to the cell.

A number of selection systems may be used to recover the cells that have been transformed for recombinant protein production. Such selection systems include, but are not limited to, HSV thymidine kinase, hypoxanthine-guanine phosphoribosyltransferase and adenine phosphoribosyltransferase genes, in tk-, hgprt- or aprt-cells, respectively. Also, anti-metabolite resistance can be used as the basis of selection for dhfr, that confers resistance to methotrexate; gpt, that confers resistance to mycophenolic acid; neo, that confers resistance to the aminoglycoside, G418; also, that confers resistance to chlorsulfuron; and hygro, that confers resistance to hygromycin. Additional selectable genes that may be useful include trpB, which allows cells to utilize indole in place of tryptophan, or hisD, which allows cells to utilize histinol in place of histidine. Markers that give a visual indication for identification of transformants include anthocyanins, β-glucuronidase and its substrate, GUS, and luciferase and its substrate, luciferin.

Many of the novel compounds of the present invention may be produced using a combination of both automated peptide synthesis and recombinant techniques. For example, a compound of the invention may contain a combination of modifications including deletion, substitution, and insertion by PEGylation. Such compound may be produced in stages. In the first stage, an intermediate form of the novel compound containing the modifications of deletion, substitution, insertion, and any combination thereof, may be produced by recombinant techniques as described. Then after an optional purification step as described below, the intermediate polypeptide is PEGylated through chemical modification with an appropriate PEGylating reagent (e.g., from Nectar Transforming Therapeutics, San Carlos, Calif.) to yield the desired compound. One skilled in the art will appreciate that the above-described procedure may be generalized to apply to the novel compound containing a combination of modifications selected from deletion, substitution, insertion, derivation, and other means of modification well known in the art and contemplated by the present invention.

It may be desirable to purify the novel compounds generated by the present invention. Peptide purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography, polyacrylamide gel electrophoresis, and isoelectric focusing. A particularly efficient method of purifying peptides is reverse phase HPLC, followed by characterization of purified product by liquid chromatography/mass spectrometry (LC/MS) and Matrix-Assisted Laser Desorption Ionization (MALDI) mass spectrometry. Additional confirmation of purity is obtained by determining amino acid analysis.

Certain aspects of the present invention concern the purification, and in particular embodiments, the substantial purification, of an encoded protein or peptide. Various techniques suitable for use in peptide purification will be well known to those of skill in the art. These include, for example, precipitation with ammonium sulphate, PEG, antibodies, and the like; heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide. Methods for purifying a polypeptide can be found in U.S. Pat. No. 5,849,883. These documents describe specific exemplary methods for the isolation and purification of G-CSF compositions that may be useful in isolating and purifying the novel compounds of the invention. Given the disclosure of these patents, it is evident that one of skill in the art would be well aware of numerous purification techniques that may be used to purify polypeptides from a given source. Also it is contemplated that a combination of anion exchange and immunoaffinity chromatography may be employed to produce purified compounds of the invention.

Accordingly, the phrase "isolated polypeptide or peptide" refers to a polypeptide or peptide that is substantially free of cellular material or other contaminating proteins from the cell or tissue source from which the protein is derived, or substantially free of chemical precursors or other chemicals when chemically synthesized. The language "substantially free of cellular material" includes preparations of protein in which the protein is separated from cellular components of the cells from which it is isolated or recombinantly produced. Thus, protein that is substantially free of cellular material includes preparations of protein having less than about 30%, 20%, 10%, or 5% (by dry weight) of heterologous protein (also referred to herein as a "contaminating protein"). When the protein, peptide, or fragment thereof is recombinantly produced, it is also preferably substantially free of culture medium, i.e., culture medium represents less than about 20%, 10%, or 5% of the volume of the protein preparation. When the protein is produced by chemical synthesis, it is preferably substantially free of chemical precursors or other chemicals, i.e., it is separated from chemical precursors or other chemicals which are involved in the synthesis of the protein. Accordingly such preparations of the protein have less than about 30%, 20%, 10%, 5% (by dry weight) of chemical precursors or compounds other than the polypeptide of interest. In preferred embodiments, purified or isolated preparations will lack any contaminating proteins from the same animal from which the protein is normally produced, as can be accomplished by recombinant expression of, for example, a human protein in a non-human cell.

Certain preferred methods for synthesis are described in the commonly-assigned U.S. Pat. No. 454,533 (file Dec. 6, 1999) the entirety of which is incorporated herein by reference.

For all indications, the novel compounds may be administered peripherally at a dose of about 1 µg to about 5 mg per day in single or divided doses or controlled continual release, or at about 0.01 µg/kg to about 500 µg/kg per dose, more preferably about 0.05 µg/kg to about 250 µg/kg, most preferably below about 50 µg/kg. Doses may be administered one, two, three or four times a day. Dosages in these ranges will vary with the potency of each analog or derivative, of course, and may be determined by one of skill in the art.

In the methods of the present invention, the polypeptides may be administered separately or together with one or more other compounds and compositions that exhibit a long term or short-term action to reduce nutrient availability, including, but not limited to other compounds and compositions that comprise an amylin or amylin analog agonist, salmon calcitonin or salmone calcitonin agonist, a cholecystokinin (CCK) or CCK agonist, a leptin (OB protein) or leptin agonist, an exendin or exendin analog agonist, or a GLP-1 or GLP-1 analog agonist or a PYY or PYY analog, or a PYY related polypeptide. Suitable amylin agonists include, for example, [25,28,29 Pro-]-human amylin (also known as "pramlintide," and described in U.S. Pat. Nos. 5,686,511 and 5,998,367). The CCK used is preferably CCK octopeptide (CCK-8). Leptin is discussed in, for example, (Pelleymounter, Cullen et al., Science 269: 540-543 (1995); Halaas, Gajiwala et al., Science 269: 543-6 (1995); Campfield, Smith et al., Science 269: 546-549 (1995)). Suitable exendins include exendin-3 and exendin-4, and exendin agonist compounds include, for example, those described in PCT Publications WO 99/07404, WO 99/25727, and WO 99/25728. Suitable PYY polypeptides and analogs include those described in U.S. application Ser. Nos. 11/055,093 and 11/055,098.

Pharmaceutical Compositions

The present invention also relates to pharmaceutical compositions comprising a therapeutically or prophylactically effective amount of at least one compound of the invention, or a pharmaceutically acceptable salt thereof, together with pharmaceutically acceptable diluents, preservatives, solubilizers, emulsifiers, adjuvants and/or carriers useful in the delivery of the novel compounds. Such compositions may include diluents of various buffer content (e.g., acetate, citrate, tartrate, phosphate, TRIS), pH and ionic strength; additives such as surfactants and solubilizing agents (e.g., sorbitan monooleate, lecithin, Pluronics, Tween 20 & 80, Polysorbate 20 & 80, propylene glycol, ethanol, PEG-40, sodium dodecyl sulfate), anti-oxidants (e.g., monothioglyercol, ascorbic acid, acetylcysteine, sulfurous acid salts (bisulfise and metabisulfite), preservatives (e.g., phenol, meta-cresol, benzyl alcohol, parabens (methyl, propyl, butyl), benzalkonium chloride, chlorobutanol, thimersol, phenylmercuric salts, (acetate, borate, nitrate), and tonicity/ bulking agents (glycerine, sodium chloride, mannitol, sucrose, trehalose, dextrose) incorporation of the material into particulate preparations of polymeric compounds, such as polylactic acid, polyglycolic acid, etc., or in association with liposomes. Such compositions will influence the physical state, stability, rate of in vivo release, and rate of in vivo clearance of the present compounds. See, e.g., Remington's Pharmaceutical Sciences 1435-712, 18th ed., Mack Publishing Co., Easton, Pa. (1990).

In general, the present compounds will be useful in the same way that amylin is useful in view of their pharmacological properties. One preferred use is to peripherally administer such novel compounds for the treatment or prevention of metabolic conditions and disorders. In particular, the compounds of the invention possess activity as agents to reduce nutrient availability, reduce food intake, and effect weight loss.

The novel compounds may be formulated for peripheral administration, including formulation for injection, oral administration, nasal administration, pulmonary administration, topical administration, or other types of administration as one skilled in the art will recognize. Examples of formulations can be found in U.S. Pat. No. 6,410,511 and patent application Ser. No. 10/159,779, incorporated herein by reference in their entirety. More particularly, administration of the pharmaceutical compositions according to the present invention may be via any common route so long as the target tissue is available via that route. In a preferred embodiment, the pharmaceutical compositions may be introduced into the subject by any conventional peripheral method, e.g., by intravenous, intradermal, intramusclar, intramammary, intraperitoneal, intrathecal, retrobulbar, intrapulmonary (e.g., term release); by oral, sublingual, nasal, anal, vaginal, or transdermal delivery, or by surgical implantation at a particular site. The treatment may consist of a single dose or a plurality of doses over a period of time. Controlled continual release of the compositions of the present invention is also contemplated. Examples of microsphere technology can be found in U.S. Pat. No. 6,458,387 and U.S. Pat. No. 5,578,708, incorporated herein by reference in their entirety.

The formulation may be liquid or may be solid, such as lyophilized, for reconstitution. Aqueous compositions of the present invention comprise an effective amount of the novel compounds, dissolved or dispersed in a pharmaceutically acceptable carrier or aqueous medium. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in therapeutic compositions is contemplated. Supplementary active ingredients also can be incorporated into the compositions. In some cases, it will be convenient to provide a compound of the invention and another food-intake-reducing, plasma glucose-lowering or plasma lipid-altering agent, such as an amylin, an amylin agonist analog, a CCK or CCK agonist, or a leptin or leptin agonist, or an exendin or exendin agonist analog, or a PYY or a PYY analog, in a single composition or solution for administration together. In other cases, it may be more advantageous to administer the additional agent separately from the novel compound.

The compounds of the invention may be prepared for administration as solutions of free base, or pharmacologically acceptable salts in water suitably mixed with a surfactant, such as hydroxypropylcellulose. As used herein, the phrase "pharmaceutically acceptable salts" refers to salts prepared from pharmaceutically acceptable, preferably nontoxic, acids and bases, including inorganic and organic acids and bases, including but not limited to, sulfuric, citric, maleic, acetic, oxalic, hydrochloride, hydro bromide, hydro iodide, nitrate, sulfate, bisulfite, phosphate, acid phosphate, isonicotinate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Pharmaceutically acceptable salts include those formed with free amino groups such as, but not limited to, those derived from hydrochloric, phosphoric, acetic, oxalic, and tartaric acids. Pharmaceutically acceptable salts also include those formed with free carboxyl groups such as, but not limited to, those derived from sodium, potassium, ammonium, sodium lithium, calcium, ferric hydroxides, isopropylamine, triethylamine, 2-ethylamino ethanol, histidine, and procaine. Under ordinary conditions of storage and use, these preparations contain a preservative to prevent the growth of microorganisms.

In one embodiment, the pharmaceutical compositions of the present invention are formulated so as to be suitable for parenteral administration, e.g., via injection or infusion. Preferably, the novel compound is suspended in an aqueous carrier, for example, in an isotonic buffer solution at a pH of about 3.0 to about 8.0, preferably at a pH of about 3.0 to about 7.4, 3.5 to 6.0, or 3.5 to about 5.0. Useful buffers include sodium acetate/acetic acid, sodium lactate/lactic acid, ascorbic acid, sodium citrate-citric acid, sodium bicarbonate/carbonic acid, sodium succinate/succinic acid, histidine, Sodium benzoate/benzoic acid, and sodium phosphates, and Tris(hydroxymethyl)aminomehane. A form of repository or "depot" slow release preparation may be used so that therapeutically effective amounts of the preparation are delivered into the bloodstream over many hours or days following transdermal injection or delivery.

The pharmaceutical compositions suitable for injectable use include sterile aqueous solutions or dispersions and sterile powders for the extemporaneous preparation of sterile injectable solutions or dispersions. In all cases, the form should be sterile and should be fluid that is easily syringable. It is also desirable for the PPF polypeptide of the invention to be stable under the conditions of manufacture and storage and must be preserved against the contaminating action of microorganisms, such as bacteria and fungi. The carrier can be a solvent or dispersion medium containing, for example, water, ethanol, polyol (e.g., sorbitol, glycerol, propylene glycol, and liquid polyethylene glycol, and the like), dimethylacetamide, cremorphor EL, suitable mixtures thereof, and oils (e.g., soybean, sesame, castor, cottonseed, ethyl oleate, isopropyl myristate, glycofurol, corn). The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, meta-cresol, benzyl alcohol, parabens (methyl, propyl, butyl), chlorobutanol, phenol, phenylmercuric salts (acetate, borate, nitrate), sorbic acid, thimerosal, and the like. In many cases, it will be preferable to include tonicity agents (for example, sugars, sodium chloride). Prolonged absorption of the injectable compositions can be brought about by the use in the compositions of agents delaying absorption (for example, aluminum monostearate and gelatin). An exemplary pharmaceutical composition may be 0.1 to 5% compound of the invention in an aqueous system along with approximately 0.02 to about 0.5% (w/v) of an acetate, phosphate, citrate, or glutamate buffer to a pH of the final composition of approximately 3.0 to about 6.0 as well as approximately 1.0 to 10% (w/v) of a carbohydrate or polyhydric alcohol tonicifier; and, optionally, approximately 0.005 to 1.0% (w/v) of a preservative selected from the group consisting of m-cresol, benzyl alcohol, parabens and phenol.

Sterile injectable solutions may be prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle that contains the basic dispersion medium and the required other ingredients from those enumerated above. In the case of sterile powders for the preparation of sterile injectable solutions, the preferred methods of preparation are vacuum-drying and freeze-drying techniques that yield a powder of the active ingredient plus any additional desired ingredient from a previously sterile-filtered solution thereof.

Generally, a therapeutically or prophylactically effective amount of the present novel compounds will be determined by the age, weight, and condition or severity of the diseases or metabolic conditions or disorders of the recipient. See, e.g., Remington's Pharmaceutical Sciences 697-773. See also Wang and Hanson, Parenteral Formulations of Proteins and Peptides: Stability and Stabilizers, Journal of Parenteral Science and Technology, Technical Report No. 10, Supp. 42:2 S (1988). Typically, a dosage of between about 0.001 µg/kg body weight/day to about 1000 µg/kg body weight/day, may be used, but more or less, as a skilled practitioner will recognize, may be used. Dosing may be one or more times daily, or less frequently, and may be in conjunction with other compositions as described herein. It should be noted that the present invention is not limited to the dosages recited herein.

Appropriate dosages may be ascertained through the use of established assays for determining level of metabolic conditions or disorders in conjunction with relevant dose-response data. The final dosage regimen will be determined by the attending physician, considering factors that modify the action of drugs, e.g., the drug's specific activity, severity of the damage and the responsiveness of the patient, the age, condition, body weight, sex and diet of the patient, the severity of any infection, time of administration and other clinical factors. As studies are conducted, further information will emerge regarding appropriate dosage levels and duration of treatment for specific diseases and conditions.

An effective dose will typically be in the range of about 1 to 30 µg to about 5 mg/day, preferably about 10 to 30 µg to about 2 mg/day and more preferably about 5 to 100 µg to about 1 mg/day, most preferably about 5 µg to about 500 µg/day, administered in a single or divided doses. The dosages may be between about 0.01 to about 500 µg/dose. It is contemplated that compounds of the invention can be administered 1, 2, 3, 4 or more times a day. Accordingly, exemplary doses can be derived from the total amount of drug to be given a day and the number doses administered a day. For example, exemplary doses can range from about 0.125 µg/dose (0.5 µg given four times a day) to about 5 mg/dose (5 mg given once a day). Other dosages may be between about 0.01 to about 100 µg/kg/dose. Still other exemplary doses may be 20, 30, 40, 50, 60, 70, 80, 90, 100, 110, 120, 130, 140, 150, 160, 170, 180, 190, or 200 µg/dose. The exact dose to be administered may be determined by one of skill in the art and is dependent upon the potency of the particular compound, as well as upon the age, weight and condition of the individual. Administration should begin whenever the suppression of nutrient availability, food intake, weight, blood glucose or plasma lipid lowering is desired, for example, at the first sign of symptoms or shortly after diagnosis of obesity, diabetes mellitus, or insulin-resistance syndrome. Administration may be by any route, e.g., injection, preferably subcutaneous or intramuscular, oral, nasal, transdermal, etc. Dosages for certain routes, for example oral administration, may be increased to account for decreased bioavailablity, for example, by about 5-100 fold.

In one embodiment, where the pharmaceutical formulation is to be administered parenterally, the composition is formulation so as to deliver a dose of the novel compounds ranging from 0.1 µg/kg to 100 mg/kg body weight/day, preferably at doses ranging from 10 µg/kg to about 50 mg/kg body weight/day. Parenteral administration may be carried out with an initial bolus followed by continuous infusion to maintain therapeutic circulating levels of drug product. Those of ordinary skill in the art will readily optimize effective dosages and administration regimens as determined by good medical practice and the clinical condition of the individual patient.

The frequency of dosing will depend on the pharmacokinetic parameters of the agents and the routes of administration. The optimal pharmaceutical formulation will be determined by one of skill in the art depending on the route of administration and the desired dosage. See, e.g., Remington's Pharmaceutical Sciences, supra, pages 1435-1712. Such formulations may influence the physical state, stability, rate of in vivo release and rate of in vivo clearance of the administered agents. Depending on the route of administration, a suitable dose may be calculated according to body weight, body surface areas or organ size. Further refinement of the calculations necessary to determine the appropriate treatment dose is routinely made by those of ordinary skill in the art without undue experimentation, especially in light of the dosage information and assays disclosed herein, as well as the pharmacokinetic data observed in animals or human clinical trials.

It will be appreciated that the pharmaceutical compositions and treatment methods of the invention may be useful in fields of human medicine and veterinary medicine. Thus the subject to be treated may be a mammal, preferably human or other animal. For veterinary purposes, subjects include for example, farm animals including cows, sheep, pigs, horses and goats, companion animals such as dogs and cats, exotic and/or zoo animals, laboratory animals including mice, rats, rabbits, guinea pigs and hamsters; and poultry such as chickens, turkeys, ducks and geese.

To assist in understanding the present invention, the following Examples are included. The experiments relating to this invention should not, of course, be construed as specifically limiting the invention and such variations of the invention, now known or later developed, which would be within the purview of one skilled in the art are considered to fall within the scope of the invention as described herein and hereinafter claimed.

EXAMPLES

Example 1

Synthesis of the Caloric Intake Lowering Polypeptides

The following polypeptides can be synthesized using standard polypeptide synthesis methods. Such methods are described below and in U.S. Pat. No. 6,610,824 and U.S. Pat. No. 5,686,411 and in U.S. Pat. No. 454,533 (filed Dec. 6, 1999), the entireties of which are incorporated herein by reference.

The polypeptides are assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.). In general, single-coupling cycles are used throughout the synthesis and Fast Moc (HBTU activation) chemistry is employed. However, at some positions coupling may be less efficient than expected and double couplings required. Deprotection (Fmoc group removal) of the growing peptide chain using piperidine likewise may not always be efficient and require double deprotection. Final deprotection of the completed peptide resin is achieved using a mixture of triethylsilane (0.2 mL), ethanedithiol (0.2 mL), anisole (0.2 mL), water (0.2 mL) and trifluoroacetic acid (15 mL) according to standard methods (Introduction to Cleavage Techniques, Applied Biosystems, Inc.) The peptides are precipitated in ether/water (50 mL) and centrifuged. The precipitate is reconstituted in glacial acetic acid and lyophilized. The lyophilized peptides are dissolved in water). Crude purity is then determined.

Solvent A (0.1% TFA in water) and Solvent B (0.1% TFA in ACN) are used in purification and analysis steps.

Solutions containing the various polypeptides are applied to a preparative C-18 column and purified (10% to 40% Solvent B in Solvent A over 40 minutes). Purity of fractions are determined isocratically using a C-18 analytical column. Pure fractions are pooled furnishing the above-identified peptide. Analytical RP-HPLC (gradient 30% to 60% Solvent B in Solvent A over 30 minutes) of the lyophilized peptide to determine retention time.

Example 2

Receptor Binding Assays

Initially, polypeptides can be used in assays to determine binding ability to amylin, calictonin and CGRP receptors. Binding assays for determining interactions with the amylin-receptor, the calcitonin-receptor, and the CGRP receptor are described for example in U.S. Pat. No. 5,264,372, the entirety of which is incorporated herein by reference.

In more detail, evaluation of the binding of compounds of the invention to amylin receptors can be carried out as follows. $^{125}$I-rat amylin (Bolton-Hunter labeled at the N-terminal lysine) is purchased from Amersham Corporation (Arlington Heights, Ill.). Unlabeled peptides are obtained from BACHEM Inc. (Torrance, Calif.) and Peninsula Laboratories (Belmont, Calif.).

Male Sprague-Dawley® rats (200-250) grams are sacrificed by decapitation. Brains are removed to cold phosphate-buffered saline (PBS). From the ventral surface, cuts are made rostral to the hypothalamus, bounded laterally by the olfactory tracts and extending at a 45 angle medially from these tracts. This basal forebrain tissue, containing the nucleus accumbens and surrounding regions, is weighed and homogenized in ice-cold 20 mM HEPES buffer (20 mM HEPES acid, pH adjusted to 7.4 with NaOH at 23 C). Membranes are washed three times in fresh buffer by centrifugation for 15 minutes at 48,000.times.g. The final membrane pellet is resuspended in 20 mM HEPES buffer containing 0.2 mM phenylmethylsulfonyl fluoride (PMSF).

To measure $^{125}$I-amylin binding, membranes from 4 mg original wet weight of tissue are incubated with $^{125}$I-amylin at 12-16 pM in 20 mM HEPES buffer containing 0.5 mg/ml bacitracin, 0.5 mg/ml bovine serum albumin, and 0.2 mM PMSF. Solutions are incubated for 60 minutes at 2 C. Incubations are terminated by filtration through GF/B glass fiber filters (Whatman Inc., Clifton, N.J.) which has been pre-soaked for 4 hours in 0.3% poylethyleneimine in order to reduce nonspecific binding of radiolabeled peptides. Filters are washed immediately before filtration with 5 ml cold PBS, and immediately after filtration with 15 ml cold PBS. Filters are removed and radioactivity assessed in a gamma-counter at a counting efficiency of 77%. Competition curves are generated by measuring binding in the presence of $10^{-12}$ to $10^{-6}$ M unlabeled test compound and are analyzed by nonlinear regression using a 4-parameter logistic equation (Inplot program; GraphPAD Software, San Diego).

In this assay, purified human amylin binds to its receptor at a measured $IC_{50}$ of about 50 pM. Results for test compounds of the invention are set forth in the table below, showing that each of the compounds has significant receptor binding activity.

Evaluation of the binding of compounds of the invention to CGRP receptors was essentially as described for amylin except using 125I hCGRP and membranes prepared from SK-N-MC cells, known to express CGRP receptors (Muff, R. et. al. Ann NY Acad. Sci. 1992: 657, 106-16). Binding assays were performed as described for amylin except using 13,500 cpm 125I-hCGRP/well or 21.7 pM/well (Amersham).

Binding to the calcitonin receptor may be investigated using CHO cells or T47D cells, which also express the calcitonin receptor (Muff R. et. al, *Ann NY Acad Sci.* 1992, 657: 106-16 and Kuestner R. E. et. al. *Mol Pharmacol.* 1994, 46:246-55), as known in the art

TABLE 2

| | $EC_{50}$ values (nM) for polypeptides | | |
|---|---|---|---|
| Compound | Amylin | Calcitonin | CGRP |
| 1 | 0.028 | 0.029 | 2.342 |
| 2 | 0.047 | 0.052 | 33.988 |
| 3 | 0.023 | 0.020 | 0.490 |
| 4 | 0.035 | 0.019 | 8.500 |
| 5 | 0.022 | 0.018 | 2.600 |
| 6 | 0.030 | nt | nt |
| 7 | 0.057 | nt | 7.540 |
| 8 | 8.070 | 0.478 | 175.665 |
| 9 | 0.043 | 0.014 | 1.600 | nt denotes not tested

Example 3

Activity of Polypeptides on Food Intake

Female NIH/Swiss mice (8-14 weeks old) were group housed with a 12:12 hour light:dark cycle. Water and a standard pelleted mouse chow diet are available ad libitum, except as noted. Animals are fasted starting at approximately 1500 hrs, 1 day prior to experiment.

At time=0 min, all animals are given an intraperitoneal injection of vehicle or polypeptide in a volume of 200 uL/mouse and immediately given a pre-weighed amount (10-15 g) of the standard chow. Food is removed and weighed at 30, 60, 120 and 180 minutes to determine the amount of food consumed. The effects of treatment on food intake are expressed as % change relative to control.

As can be seen in FIG. 1, Compound 2, at doses from 25-300 nmol/kg, dose-dependently reduced food intake at 30 minutes post injection. The table below depicts reduced food intake with polypeptides administered peripherally (intraperitoneal injection) at doses 25 nmol/kg. The data at time points 30, 60, 120, and 180 minutes represents the percent decrease in cumulative food intake compared to the vehicle.

TABLE 3

| Compound (SEQ ID NO:) | 30 min | 60 min | 120 min | 180 min |
|---|---|---|---|---|
| 1 (137) | −58 | −46 | −33 | −22 |
| 2 (136) | −58 | −54 | −52 | nt |
| 3 (135) | −58 | −52 | −37 | −33 |
| 4 (40) | −42 | −31 | −35 | −30 |
| 5 (43) | −66 | −53 | −29 | −27 |
| 6 | −48 | −45 | −23 | nt |
| 7 (134) | −60 | −52 | −23 | nt |
| 8 | −6 | −15 | −25 | −28 |
| 9 (71) | −80 | −64 | −43 | nt |
| 10 | −19 | −20 | −35 | nt |
| 11 (41) | −52 | −47 | −38 | −35 |
| 12 (42) | −43 | −39 | −37 | −32 |
| 13 (44) | −40 | −33 | −25 | −24 |
| 14 (45) | −52 | −36 | −28 | −33 |
| 15 (46) | −67 | −59 | −37 | −30 |
| 16 | −26 | −29 | −30 | −27 |
| 17 (47) | −42 | −30 | −30 | −25 |
| 18 (48) | −2 | −7 | −16 | −21 |
| 19 (49) | −25 | −25 | −35 | −31 |
| 20 (50) | −9 | −21 | −30 | −31 |
| 21 (51) | 9 | −5 | −18 | −18 |
| 22 (52) | −11 | −20 | −31 | −30 |
| 23 (53) | 8 | 0 | −19 | −12 |
| 24 (54) | −40 | −34 | −35 | −35 |
| 25 (55) | −29 | −34 | −45 | nt |
| 26 (56) | −29 | −36 | −47 | nt |
| 27 (57) | −12 | −11 | −32 | nt |
| 28 (58) | −8 | −16 | −28 | nt |
| 29 (59) | 4 | −1 | −25 | nt |
| 30 (60) | −1 | −2 | −19 | nt |
| 31 (61) | −11 | −18 | −23 | nt |
| 32 (62) | −15 | −21 | −31 | nt |
| 33 | −7 | −10 | −15 | nt |
| 34 | −11 | −6 | −16 | nt |
| 35 (63) | −20 | −16 | −18 | nt |
| 36 (64) | −34 | −22 | −24 | −25 |
| 37 (65) | −3 | −2 | −16 | nt |
| 38 | −24 | −13 | −8 | nt |
| 39 (66) | 7 | −14 | −23 | nt |
| 40 | −11 | −5 | −2 | nt |
| 41 | −4 | −9 | −12 | nt |
| 42 | −11 | −18 | −32 | nt |
| 43 | −4 | −7 | −18 | nt |
| 44 (69) | −6 | −13 | −25 | nt |
| 45 | −13 | −7 | −3 | nt |
| 46 | −6 | −11 | −16 | nt |
| 47 (70) | −5 | −13 | −27 | nt |
| 48 (72) | −54 | −51 | −36 | nt |
| 49 (73) | −33 | −26 | −25 | nt |
| 50 (74) | −70 | −62 | −48 | nt |
| 51 (75) | −44 | −39 | −35 | nt |
| 52 (76) | −29 | −24 | −23 | nt |
| 53 (77) | −92 | −89 | −36 | nt |
| 54 | 1 | −4 | −10 | nt |
| 55 | 9 | −5 | −12 | nt |
| 56 | 4 | −13 | −16 | nt |
| 57 (78) | −18 | −24 | −23 | nt |
| 58 (79) | −62 | −51 | −29 | nt |
| 59 (80) | −81 | −77 | −50 | nt |
| 60 (81) | −43 | −40 | −26 | nt |
| 61 (82) | −23 | −27 | −32 | nt |
| 62 (83) | −14 | −22 | −38 | nt |
| 63 (84) | −19 | −22 | −28 | nt |
| 64 (85) | −65 | −58 | −44 | nt |
| 65 (86) | −33 | −29 | −32 | nt |
| 66 (87) | −13 | −15 | −28 | nt |
| 67 | −10 | −11 | −12 | nt |
| 68 (88) | −10 | −13 | −21 | nt |
| 69 (89) | −29 | −31 | −45 | nt |
| 70 (90) | −76 | −64 | −47 | nt |

TABLE 3-continued

| Compound (SEQ ID NO:) | 30 min | 60 min | 120 min | 180 min |
|---|---|---|---|---|
| 71 (91) | −7 | −13 | −22 | −18 |
| 72 (92) | 0 | −8 | −13 | −19 |
| 73 (93) | −51 | −31 | −23 | −28 |
| 74 (94) | −42 | −32 | −31 | nt |
| 75 (95) | −60 | −52 | −38 | nt |
| 76 (96) | −25 | −29 | −40 | nt |
| 77 (97) | −46 | −43 | −44 | nt |
| 78 (98) | −57 | −44 | −44 | nt |
| 79 (99) | −49 | −40 | −33 | nt |
| 80 (100) | −32 | −28 | −22 | nt |
| 81 (101) | −28 | −24 | −33 | nt |
| 82 (102) | −7 | −13 | −16 | −19 |
| 83 (103) | −7 | −13 | −22 | −12 |
| 84 (104) | −53 | −40 | −20 | nt |
| 85 (105) | 3 | −16 | −16 | nt |
| 86 (106) | −44 | −26 | −16 | nt |
| 87 (107) | −43 | −32 | −21 | nt |
| 88 (108) | −64 | −61 | −39 | −22 |
| 89 (109) | −6 | −13 | −22 | −20 |
| 90 (110) | −55 | −41 | −24 | −15 |
| 91 (111) | −59 | −47 | −26 | −24 |
| 92 (112) | −31 | −29 | −30 | −27 |
| 93 (113) | −43 | −30 | −27 | −29 |
| 94 (114) | −62 | −42 | −36 | −31 |
| 95 (115) | −81 | −69 | −34 | −31 |
| 96 (116) | −49 | −38 | −19 | −23 |
| 97 (117) | −78 | −76 | −60 | −40 |
| 98 | −18 | −13 | −5 | −1 |
| 99 (118) | −57 | −55 | −50 | nt |
| 100 (119) | −60 | −52 | −41 | nt |
| 101 (120) | −52 | −48 | −35 | nt |
| 102 (121) | −58 | −53 | −45 | nt |
| 103 (122) | −50 | −44 | −30 | nt |
| 104 (123) | −69 | −67 | −54 | nt |
| 105 (124) | −83 | −82 | −52 | nt |
| 106 (125) | −58 | −54 | −39 | nt |
| 107 (126) | −84 | −78 | −47 | nt |
| 108 (127) | −70 | −66 | −38 | nt |
| 109 (128) | −61 | −54 | −43 | nt |
| 110 (129) | −80 | −72 | −59 | nt |
| 111 (130) | −39 | −37 | −32 | nt |
| 112 (131) | −62 | −65 | −50 | nt |
| 113 (132) | −79 | −86 | −55 | nt |
| 114 (133) | −17 | −20 | −25 | nt |
| 115 | 6 | −3 | −25 | −25 |
| 116 | 5 | 5 | 3 | nt |
| 117 | −13 | −11 | −3 | nt |
| 118 | −4 | 0 | 13 | nt |
| 119 | 6 | −8 | −11 | nt |
| 120 | −3 | 1 | −6 | −7 |
| 121 | 5 | 2 | −1 | 3 |
| 122 | −6 | −12 | −23 | −21 |
| 123 | 1 | −13 | −17 | −13 |
| 124 | 4 | −4 | −15 | −16 |
| 125 | 10 | −1 | −6 | nt |
| 126 | 5 | −10 | −20 | nt |
| 127 | −5 | −14 | −12 | −12 | nd = not done

Example 4

Activity of Compounds of the Invention on Weight Reduction and Caloric Intake

Individually housed male Sprague-Dawley® rats (350 g; 12-h light/dark cycle) were maintained on a high fat diet (58% kcal from fat) for 4 weeks. At the end of fattening period, 14-day osmotic pumps (Durect Corp.) were implanted interscapularly under anesthesia. Rats received pumps continuously delivering vehicle (50% DMSO) or polypeptide at a dose of 2.9 nmol/kg/day. Food intake and body weight measurements were obtained weekly. FIGS. 2A and 2B show that the polypeptides Compound 3, Compound 4, or Compound 5 produced a decrease in caloric intake and body weight gain throughout the 14-day test period.

The table below presents the percent body weight loss at week 1 and 2 for several compounds.

TABLE 4

Body weight loss after administration of exemplary compounds of the invention

| Compound | Week 1 | Week 2 |
|---|---|---|
| Compound 1 | 8.3* | 10.5* |
| Compound 2 | 9.8* | 9.4* |
| Compound 3 | 5.9* | 6.7* |
| Compound 4 | 6.8* | 9.2* |
| Compound 5 | 8.6* | 11.3* |
| Compound 6 | 2.9* | 3.8* |
| Compound 7 | 10.0* | 11.4* |
| Compound 8 | 2.3 | 2.5 |
| Compound 9 | 4.9* | 4.9* |

*$P < 0.05$ compared to controls

Example 5

Body Composition

Individually housed male Sprague-Dawley® rats (420 g; 12-h light/dark cycle) were maintained on a high fat diet (58% kcal from fat) for 4 weeks. At the end of fattening period, 14-day osmotic pumps (Durect Corp.) were implanted interscapularly under anesthesia. Rats received pumps that continuously delivered vehicle (50% DMSO) or Compound 1 at a dose of 70 nmol/kg/day. Animals were sacrificed on Day 12. Carcasses were immediately frozen and body composition (fat and protein) measured by chemical analysis (Covance Laboratories, Madison, Wis.). FIG. 3 shows that, as a percent of total body mass, fat content was reduced in rats treated with Compound 1 compared to controls. In addition, Compound 1 increased the percent of lean mass content.

Example 6

Gastric Emptying and Ion Calcium

Gastric emptying was monitored by measuring the appearance in plasma of gavaged tritiated glucose. Subjects were conscious, male Sprague Dawley® rats (7-9 weeks of age, 12:12 h light:dark cycle) with ad libitum access to food and water until the start of the experiment. Prior to dosing, food and water were removed. At t=−5 min, peptide or vehicle (200 µl saline) was administered subcutaneously. At t=0 min, a solution of 1 ml sterile water containing 5 µCi D-[3-3H] glucose (Dupont, Wilmington, Del., USA) was given by oropharyngeal tube. At t=20 min, topical anesthetic (Hurricaine®, 20% benzocaine liquid) was applied to the tip of the tail. At t=40 min, the tip of the tail was ligated with a scalpel and ~250 µl blood was collected into heparinized tubes. Plasma was then immediately assayed for ionized calcium using a Ciba/Corning 634 Ca/pH analyzer (Ciba/Corning, Inc., Medfield, Mass.). A 10 µl plasma sample was pipetted into prepared scintillation vials (0.5 ml water+2 ml scintillation cocktail (Ecolite scintillation cocktail ICN, Costa Mesa, Calif.)), vortexed and counted in a β-counter (1209 Rackbeta; LKB-Wallac, Gaithersburg, Md.) for 1 minute/vial.

In FIG. 4A, points represent mean±sd of 6 SD rats (fed, conscious). The indicated dose of peptide was injected subcutaneously at t=0. Blood was collected 35 minutes later for cpm analysis. *All points p<0.001 vs. saline control; ANOVA, Dunnett's test. From non-linear regression: ED50=2.3 µg/kg. Bottom=25 cpm/10 µl; Top=328 cpm/10 µl. Maximum decrease in plasma cpm: −92%. Goodness of fit: $r^2=0.9992$.

In FIG. 4B, points represent mean±sd of 6 SD rats (fed, conscious). The indicated dose of peptide was injected subcutaneously at t=0. Blood was collected 35 minutes later for cpm analysis. *P<0.001 vs. saline control; ANOVA, Dunnett's test. From non-linear regression: ED50=1.1 µg/kg. Bottom=1.2 mmol/L; Top=1.3 mmol/L. Maximum decrease in plasma iCa: −14% Goodness of fit: $r^2=0.9936$.

Example 7

Triglycerides

In study 1, female Harlan Sprague-Dawley® rats (HSD; HarlanTeklad, Indianapolis, Ind.) retired from breeding were fed a high-fat diet (40% of calories from fat; Diet #TD95217, HarlanTeklad) for 9 weeks prior to the initiation of the study, continuing on this diet throughout the experimental period. One group of rats were fed ad libitum throughout the study to examine the metabolic effects of Compound 1, a representative compound of the invention, treatment (n=10) relative to control, untreated rats (n=10). To determine the metabolic effects of Compound 1 in the setting of food restriction ("dieting"), a second group of rats was given 75% of their pre-study baseline food intake each day for 10 days prior to initiation of Compound 1 (n=10) or vehicle (n=10) treatment (~5% body weight loss vs. pre-restriction body weight). At that time, all rats received Alzet® osmotic pumps (Durect, Cupertino, Calif.) surgically implanted in the intrascapular region subcutaneously under isoflurane anesthesia. The pumps were prepared to deliver either Compound 1 (101 µg/kg/day) or vehicle (50% dimethoxysulfoxide [DMSO] in water) continuously for 21 days. Food-restricted rats continued to be given 75% of their baseline food intake each day. After 21 days of treatment, blood samples were obtained into heparinized syringes via cardiac puncture from isoflurane-anesthetized postabsorptive rats (~2-4 hr fasted in the a.m.) and plasma obtained for analyte analysis. Plasma triglycerides were determined using standard automated analysis for clinical chemistry (LabCorp, Inc., San Diego, Calif.).

In study 2, male rats from the obesity-prone Levin strain of HSD rats (Charles River, Wilmington, Mass.) were fed a high-fat diet (32% of calories from fat; Diet #12266B, Research Diets, Inc., New Brunswick, N.J.) for 6 wk prior to initiation of the study, and continued on this diet throughout the experiment. Initiation of treatment commenced with placement of subcutaneous osmotic pumps containing Compound 1 or DMSO vehicle as per Study 1, and continued for 3 weeks (21 days). Metabolic parameters were compared between Compound 1-treated rats (303 µg/kg/day; n=10), vehicle-treated controls (n=10), and a pair-fed group (n=10) which received daily the amount of food eaten by Compound 1-treated rats. Blood collection and analysis of plasma triglyceride concentration were performed as in Study 1, but using tail vein collection at the 1 week and 2 week points.

Study 3 was conducted as per Study 2 except animals were treated for 8 weeks (56 days) and at different doses of Compound 1. At 28 days of treatment, fresh osmotic pumps replaced used pumps. The pumps were prepared to deliver Compound 1 at doses of 1, 3, 10, or 100 µg/kg/day (n=10/group) or DMSO vehicle (controls, n=10). An additional pair-fed group (n=10) received vehicle and were fed daily the amount of food eaten by the 100 µg/kg/day Compound 1 group. Blood collection and analysis of plasma triglyceride concentration for baseline, 2, 4, and 6 week points were obtained from conscious fed rats via tail vein collection into heparinized tubes; blood collection and analysis of plasma triglyceride concentration for 8 week point was obtained from isoflurane-anesthetized fed rats into heparinized syringes via cardiac puncture, employing a standard triglyceride assay (Cobas Mira Plus, Roche Diagnostics).

Differences between mean plasma triglyceride levels across treatments for a given timepoint of the study were evaluated one-way analysis of variance (ANOVA), followed by a Dunnett's Multiple Comparison Test (Prism v. 4.01, GraphPad Software, San Diego, Calif.). Differences were considered statistically significant at p<0.05.

Figure 5:
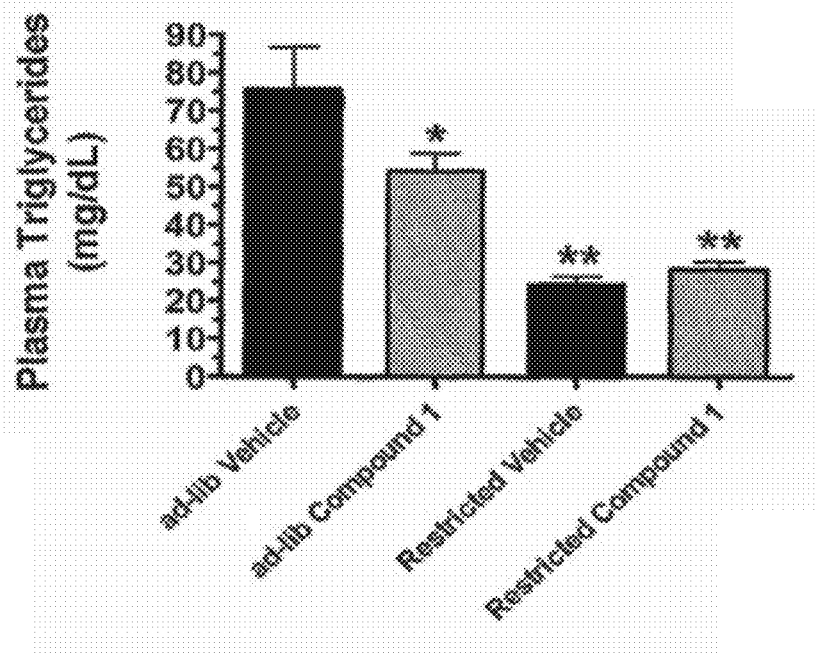
FIG. 5 depicts effects on triglycerides by an exemplary compound of the invention.

As indicated in FIGS. 5 to 7E, studies 1, 2, and 3, respectively, treatment with Compound 1 over 1-8 weeks resulted in significantly lower triglyceride concentrations. FIG. 5 shows plasma triglyceride concentration in Female Retired Breeder rats following a 21 day treatment with Compound 1 via continuous subcutaneous (s.c.) infusion. Rats administered Compound 1 displayed significantly lower triglyceride levels compared to ad lib fed controls: this effect was observed regardless of whether Compound 1 was given under ad lib fed conditions or under food-restricted conditions. *p<0.05, **p<0.01 compared to ad lib, vehicle-treated controls.

FIGS. 6A-6C depict plasma triglyceride concentration in Diet-induced Obese (DIO) Male Levin rats during a 3 week treatment with Compound 1 via continuous s.c. infusion. Graphs represent values derived from blood samples collected at (A) 1 week, (B) 2 weeks, and (C) 3 weeks of treatment. *p<0.05, **p<0.01 compared to vehicle-treated controls.

FIGS. 7A-7E show a dose response study of Compound 1, where doses as low as 1 µg/kg/day resulted in a reduction in plasma triglyceride concentrations when compared to vehicle controls at the 2, 4, 6 and 8 week points (FIGS. 7B, C, D, and E, respectively). *p<0.05, **p<0.01 compared to vehicle-treated controls. Treatment groups are indicated in the legend.

Example 8

Ghrelin Assay

This example provides an exemplary assay for detecting the effect of the compounds of the invention on ghrelin.

Male Harlan Sprague Dawley® (HSD) rats were housed at 22.8+/−0.8° C. in a 12:12 hour light:dark cycle. All experiments were performed in the light cycle. Animals were fasted for approximately 20 hours before experimentation. All animals were given free access to water until the start of the experiment. The animals' tails were anesthetized with 20% benzocaine (Hurricaine, Beutlich Pharmaceutical, Waukegan, Ill.), and blood samples were collected from the tail vein. Total and active ghrelin concentrations were measured using Linco RIA kits GHRA-89HK and GHRA-88HK, respectively.

Figure 8A:
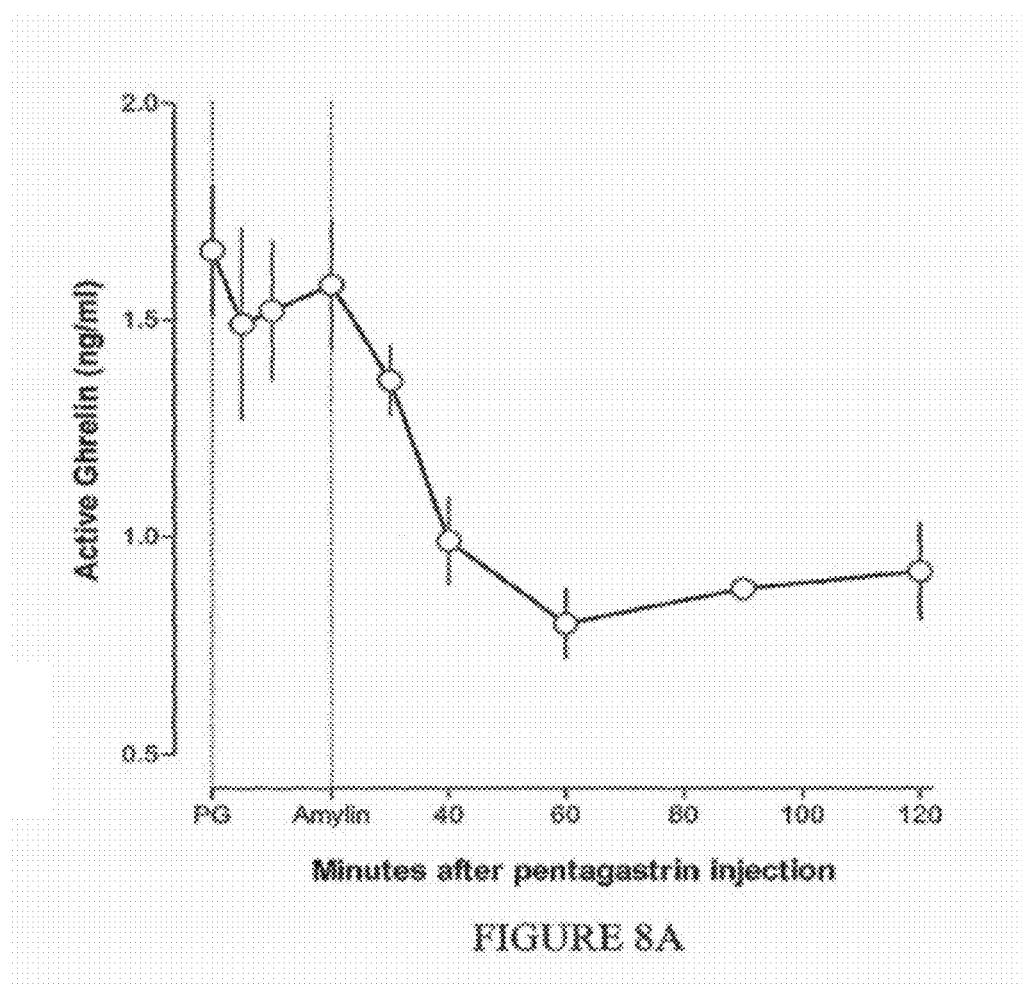
FIG. 8A depicts the effect on ghrelin by amylin following the administration of a pentagastrin injection.

In study 1, HSD rats were subjected to periodic blood sampling from the topically anesthetized tail and ghrelin levels were assayed. At t=0, rats (n=6) were injected s.c. with 125 µg/kg pentagastrin (Sigma) to stimulate gastric acid secretion (PG=0 min in FIG. 1), and 20 min later were injected subcutaneously (s.c.) with 10 µg rat amylin. The blood samples were analyzed for total and active (acylated) ghrelin (Linco). As shown in FIG. 8A, amylin reduced active ghrelin by ~50% within 1 hour.

Figure 8B:
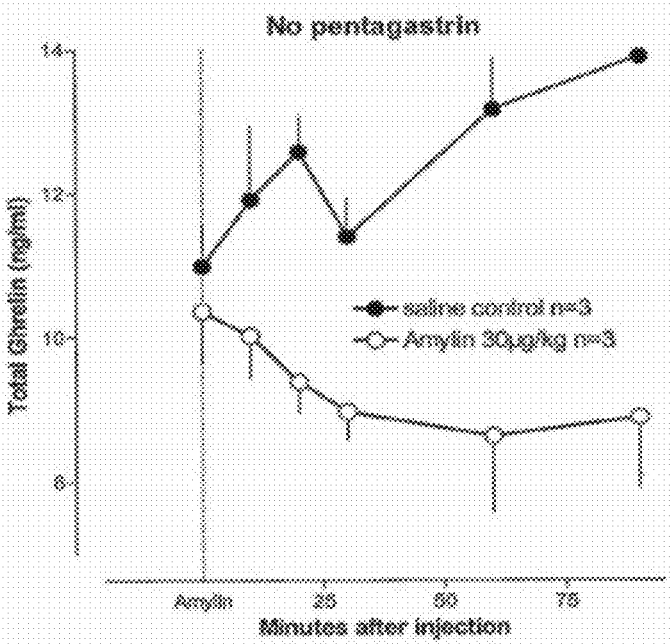
FIGS. 8B-8C depict the comparative effect on ghrelin by saline and 30 µg/kg of amylin without a pentagastrin injection (FIG. 8B) and following a pentagastrin injection (FIG. 8C).
Figure 8C:
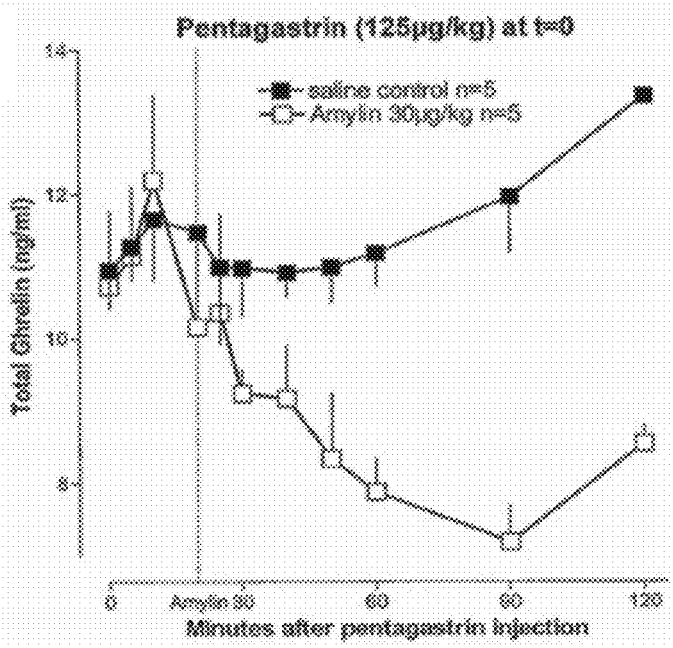

Study 2 was conducted to examine whether exogenous amylin inhibits ghrelin secretion independent of pentagastrin stimulation. Fasted rats were given either a subcutaneous injection of saline or of 30 µg/kg rat amylin or a subcutaneous injection of either saline or 125 µg/kg pentagastrin (Sigma, Lot#050K1525) at time=0 min. Rat amylin (AC0128, lot #AR2081-42A, Amylin Pharmaceuticals), at a dose of 30 µg/kg in 100 µl of saline, or saline vehicle alone (n=5.5 respectively), was given by subcutaneous injection at time 20 min. Blood plasma samples were collected at least at times 0, 10, 20, 30, 60, and 90 min. Both FIGS. 8B and 8C show a reduction in total plasma ghrelin with the administration of amylin compared to the saline control, and FIG. 8B confirms that plasma ghrelin was reduced compared to the control in the presence of amylin alone, i.e., without pentagastrin. Pentagastrin appears to enhance the ghrelin lowering effect of amylin.

Example 9

Pancreatic Function

Femoral artery and vein cannulations are performed in fasted, anesthetized HSD rats (weight 320-350 g) and they are allowed to stabilize for 90 minutes. At t=−30, an infusion of saline (1 ml/hr) or Compound 1 was started (1 ml/hr). At t=0, rats receive an imp injection of caerulein, 10 µg/kg. Samples for plasma amylase, lipase were collected at various time points from t=−30 to t=240

As shown in FIGS. 9A and 9B, treatment with Compound 1 attenuated increases in pancreatic enzyme activities in the blood in rat model of acute pancreatitis suggesting that agonists of amylin may be perspective drug candidates for the prevention and treatment of pancreatitis.

Example 10

Gastric Acid Secretion of Amylin

Male Harlan Sprague Dawley® rats were housed at 22.8±0.8° C. in a 12:12 hour light: dark cycle. The experiments were performed during the light cycle. The rats, fed rat chow (Teklad L M 485, Madison, Wis.), were fasted for approximately 20 hours before experimentation. They were given water ad libitum until the start of the experiment.

The rats (age 9-14 weeks, body mass 264-395 g) were surgically fitted with double gastric fistulae by the supplier (Zivic Miller, Catalog number SCAO3.00). During laparotomy under halothane anesthesia, a grommet-shaped double lumen plug was sutured into the stomach wall. Two silastic 2.3 mm internal diameter (entry and exit) cannulae connected to the plug and communicating with the gastric lumen were tracked through the abdominal wall, subcutaneously to the interscapular region where they were separately exteriorized. The laparotomy wound was closed with clips, the rat was placed in a heated recovery cage for one day with free access to water. Thereafter, the rats were housed singly with free access to water and rat chow until they were subjected to overnight fasting for experiments which were performed on conscious rats, about 10-15 days after surgery.

Gastric catheters were uncapped and attached to flexible PE240 tubing for injection and sampling. To ensure patency of the catheters, 2-3 mL of saline solution at room temperature was injected and immediately withdrawn from the stomach. This was repeated until flow was easy and the effluent was clean. Gastric acid secretion was measured at 10 min intervals by injecting 5 mL saline and 2 mL air via one catheter, then immediately withdrawing the same via the other catheter. In this way errors due to incomplete aspiration of the small, secreted volume could be minimized. Three mL of each gastric aspirate were titrated to pH 7.0 with 0.01 N sodium hydroxide using a pH meter (Beckman model number PHI34 Fullerton, Calif.). The amount of base required for each titration, corrected for the total volume aspirated, was used to calculate the moles of acid in each sample.

After a baseline sample was collected and the recovered volume recorded, the animals were given a subcutaneous injection of 125 µg/kg pentagastrin (Peninsula Laboratories lot number 019945 and 034686), and the 10 min gastric sampling continued for another 2 hours. At forty min after pentagastrin injection, by which time a stable plateau of gastric acid secretion was observed, the rats were injected subcutaneously with saline (n=6) or with rat amylin (batch number AR905-80, Amylin Pharmaceuticals Inc., San Diego, Calif.) at doses of 0.01, 0.1, 1.0, 10.0 or 100 µg (n=3, 3, 4, 5, 5 respectively).

As shown in FIG. 10A, pentagastrin stimulated gastric acid secretion 4.6-fold from a basal rate of about 13.8±2.2 µmol/10 min to about 63.4±3.3 µmol/10 min, 40 minutes after pentagastrin injection (grand means; $P<0.0001$). Amylin injected 40 min after pentagastrin dose-dependently inhibited gastric acid production with half lives for the onset of action of 8.6, 10.4, 5.8 and 6.3 min for doses of 0.1, 1, 10 and 100 µg, respectively. With the highest (100 µg) dose of amylin, pentagastrin-stimulated secretion of acid was reduced by 93.4±2.6% one hour after amylin injection ($P<0.001$ for doses 0.1-100 µg). This rate of secretion was only 32% of the basal rate that preceded pentagastrin injection ($P<0.01$, t-test, Welch correction). The dose response for amylin inhibition of pentagastrin-stimulated acid secretion is shown in FIG. 10B. The $ED_{50}$ for the acid-suppressive effect of amylin was 0.05 µg/rat±0.15 log units (41 pmol/kg).

Example 11

Gastroprotective Effects of Amylin

Figure 11A:
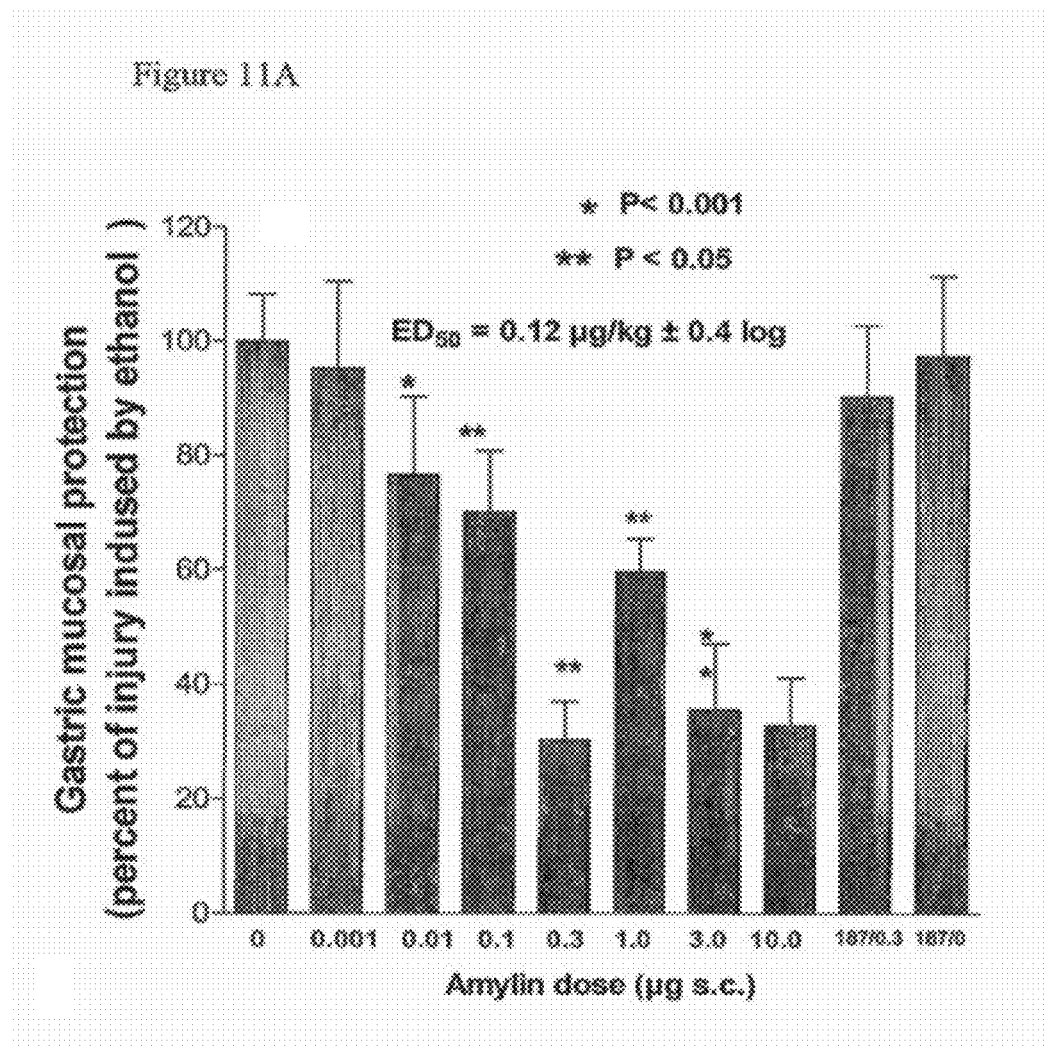
FIG. 11A depicts the gastric mucosal protection of amylin.

Fasted male rats, body weight 163-196 g, were injected subcutaneously with 0.1 mL saline (n=12) or with the same volume containing rat amylin at doses of 0.001, 0.01, 0.1, 0.3, 1, 3 or 10 µg (n=5, 5, 5, 9, 9, 5, 6 respectively) 20 min before gavage with 1 mL absolute ethanol (ethyl alcohol-200 proof dehydrated alcohol, USP, Spectrum Quality Products, Inc. Gardena, Calif.). Thirty min after gavage, each rat was anesthetized with 5% halothane, the stomach excised, opened along the lesser curvature and everted to expose the mucosa. The everted stomachs were gently rinsed with saline and immediately graded for mucosal damage by each of 10 observers blinded to the experimental treatment. The grading scale was constrained between zero (no observable damage) and 5 (100% of mucosal surface covered by hyperemia, ulceration, or sloughing), comparable to the 0-5 scoring system used by others, e.g., Guidobono F. et al. Br J Pharmacol 120:581-586 (1997). FIG. 11A shows the results of the injury score as a percent of the injury induced by ethanol.

To determine whether a gastroprotective effect of amylin was attributable to an amylin-specific mechanism, 4 rats were injected intravenously with 3.0 mg of the selective amylin antagonist, AC187 (Amylin Pharmaceuticals, Inc. San Diego, Calif.), 25 min before ethanol gavage, followed 5 min later (at t=−20 min from gavage) by 0.3 µg rat amylin injected subcutaneously. Stomachs were excised and graded for injury 30 min after ethanol gavage, as described above. The result is provided in the next to the last bar of FIG. 11A. The last bar shows the results of injection of 3.0 mg of AC187 with no rat amylin injection. A more selective look at the results are shown in FIG. 11B.

FIG. 11C shows that amylin, given as a subcutaneous injection 5 min before gavage with ethanol, dose-dependently protected the stomach from mucosal injury ($P<0.05$ with doses of 0.1 µg and higher). Amylin reduced the injury score by 67% with doses of 0.3 µg and higher. The $ED_{50}$ for the gastroprotective effect of amylin in this experimental system was 0.036 µg (31 pmol/kg)±0.40 log units.

To further explore whether a gastroprotective effect of amylin could occur in response to glucose-stimulated secretion of endogenous amylin, the effect on ethanol-induced gastritis of prior intraperitoneal glucose administration (250 mg/0.5 mL D-glucose; t=−30 min from gavage; n=9) was compared to the injury observed in vehicle-treated rats (n=23). Stomachs were excised and graded for injury 30 min after ethanol gavage, as described above, and blood was taken for plasma glucose measurement. The injury response was also measured in glucose-treated rats coadministered a 3 mg intravenous bolus of AC187 (n=9).

Prior administration of D-glucose, which increased plasma glucose at t=+30 min later to 123 mg/dL (vs 76 mg/dL in controls), and which had previously been shown to increase endogenous plasma amylin concentrations in fasted Sprague Dawley rats to 4.8±0.6 pM, significantly decreased gastric injury score by 18.5±4.6% ($P<0.0005$). However, pre-injection of AC187 had no effect on injury scores in glucose-treated rats.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A method of treating eating disorders, insulin-resistance, obesity, abnormal postprandial hyperglycemia, diabetes of any kind, including Type I, Type II, and gestational diabetes, Metabolic Syndrome, Dumping Syndrome, hypertension, dyslipidemia, cardiovascular disease, hyperlipidemia, sleep apnea, pulmonary hypertension, cholecystitis, or osteoarthritis comprising administering to a subject in need thereof an effective amount of a peptide having at least 92% sequence identity to the amino acid sequence of SEQ ID NO:137.

2. The method of claim 1, wherein the peptide having at least 92% sequence identity comprises the amino acid sequence of SEQ ID NO:55, 67, 70, 73, 82, 83, 84, 89, 94, 100, 103, 106, 107, 111, 112, 125, 133, or 137.

3. The method of claim 1, wherein the peptide having at least 92% sequence identity comprises the amino acid sequence of SEQ ID NO:137.

4. The method of claim 1, wherein the peptide is linked to a polyethylene glycol polymer, a polyamino acid, or a fatty acid.

5. A method of treating eating disorders, insulin-resistance, obesity, abnormal postprandial hyperglycemia, diabetes of any kind, including Type I, Type II, and gestational diabetes, Metabolic Syndrome, Dumping Syndrome, hypertension, dyslipidemia, cardiovascular disease, hyperlipidemia, sleep apnea, pulmonary hypertension, cholecystitis, or osteoarthritis comprising administering to a subject in need thereof an effective amount of a peptide having at least 95% sequence identity to the amino acid sequence of SEQ ID NO:137.

6. The method of claim 5, wherein the peptide having at least 95% sequence identity comprises the amino acid sequence of SEQ ID NO:40, 42, 43, 46, 47, 48, 54, 64, 65, 68, 69, 74, 78, 79, 80, 81, 85, 90, 91, 92, 93, 95, 96, 97, 98, 99, 101, 102, 109, 118, 119, 121, 130, or 137.

7. The method of claim 5, wherein the peptide having at least 95% sequence identity comprises the amino acid sequence of SEQ ID NO:137.

8. The method of claim 5, wherein the peptide is linked to a polyethylene glycol polymer, a polyamino acid, or a fatty acid.

\* \* \* \* \*

SEQUENCE LISTING

```
<160> NUMBER OF SEQ ID NOS: 138

<210> SEQ ID NO 1
<211> LENGTH: 37
<212> TYPE: PRT
<213> ORGANISM: Homo sapiens

<400> SEQUENCE: 1

Lys Cys Asn Thr Ala Thr Cys Ala Thr Gln Arg Leu Ala Asn Phe Leu
 1               5                  10                  15

Val His Ser Ser Asn Asn Phe Gly Ala Ile Leu Ser Ser Thr Asn Val
            20                  25                  30

Gly Ser Asn Thr Tyr
        35

<210> SEQ ID NO 2
<211> LENGTH: 37
<212> TYPE: PRT
<213> ORGANISM: Rattus sp.

<400> SEQUENCE: 2

Lys Cys Asn Thr Ala Thr Cys Ala Thr Gln Arg Leu Ala Asn Phe Leu
 1               5                  10                  15

Val Arg Ser Ser Asn Asn Leu Gly Pro Val Leu Pro Pro Thr Asn Val
            20                  25                  30

Gly Ser Asn Thr Tyr
        35

<210> SEQ ID NO 3
<211> LENGTH: 32
<212> TYPE: PRT
<213> ORGANISM: Oncorhynchus sp.

<400> SEQUENCE: 3

Cys Ser Asn Leu Ser Thr Cys Val Leu Gly Lys Leu Ser Gln Glu Leu
 1               5                  10                  15

His Lys Leu Gln Thr Tyr Pro Arg Thr Asn Thr Gly Ser Gly Thr Pro
            20                  25                  30
```

```
<210> SEQ ID NO 4
<211> LENGTH: 32
<212> TYPE: PRT
<213> ORGANISM: Homo sapiens

<400> SEQUENCE: 4

Cys Gly Asn Leu Ser Thr Cys Met Leu Gly Thr Tyr Thr Gln Asp Phe
 1               5                  10                  15

Asn Lys Phe His Thr Phe Pro Gln Thr Ala Ile Gly Val Gly Ala Pro
            20                  25                  30

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide motif
<220> FEATURE:
<221> NAME/KEY: MOD_RES
<222> LOCATION: (1)
<223> OTHER INFORMATION: Any amino acid or not present; see
      specification as filed for detailed
      description of substitutions and preferred
      embodiments
<220> FEATURE:
<221> NAME/KEY: MOD_RES
<222> LOCATION: (2)
<223> OTHER INFORMATION: Any amino acid or not present; see
      specification as filed for detailed
      description of substitutions and preferred
      embodiments
<220> FEATURE:
<221> NAME/KEY: MOD_RES
<222> LOCATION: (3)
<223> OTHER INFORMATION: Any amino acid or not present; see
      specification as filed for detailed
      description of substitutions and preferred
      embodiments
<220> FEATURE:
<221> NAME/KEY: MOD_RES
<222> LOCATION: (4)
<223> OTHER INFORMATION: Any amino acid, see specification as filed for
      detailed description of substitutions and
      preferred embodiments
<220> FEATURE:
<221> NAME/KEY: MOD_RES
<222> LOCATION: (5)
<223> OTHER INFORMATION: Any amino acid, see specification as filed for
      detailed description of substitutions and
      preferred embodiments
<220> FEATURE:
<221> NAME/KEY: MOD_RES
<222> LOCATION: (6)
<223> OTHER INFORMATION: Any amino acid, see specification as filed for
      detailed description of substitutions and
      preferred embodiments

<400> SEQUENCE: 5

Xaa Xaa Xaa Xaa Xaa Xaa
 1               5

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Cys Asn Thr Ala Thr Cys
 1               5
```

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Cys Ala Thr Ala Thr Cys
 1               5

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Cys Asp Thr Ala Thr Cys
 1               5

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Cys Gly Thr Ala Thr Cys
 1               5

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Cys Asn Ala Ala Thr Cys
 1               5

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Cys Asn Thr Ser Thr Cys
 1               5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES

```
<222> LOCATION: (5)
<223> OTHER INFORMATION: D-Thr

<400> SEQUENCE: 12

Cys Asn Thr Ala Thr Cys
  1               5

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: Thr(OPO3H2)

<400> SEQUENCE: 13

Cys Asn Thr Ala Thr Cys
  1               5

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Cys Asn Thr Ala Ser Cys
  1               5

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Cys Asn Thr Ala Ala Cys
  1               5

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Cys Asn Thr Ala Val Cys
  1               5

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: Hse
```

```
<400> SEQUENCE: 17

Cys Asn Thr Ala Xaa Cys
 1               5

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: Ahb

<400> SEQUENCE: 18

Cys Asn Thr Ala Xaa Cys
 1               5

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: Ahp

<400> SEQUENCE: 19

Cys Asn Thr Ala Xaa Cys
 1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Cys Ser Asn Leu Ser Thr Cys
 1               5

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Cys Gly Asn Leu Ser Thr Cys
 1               5

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22
```

```
Cys Ala Asn Leu Ser Thr Cys
  1               5

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Cys Ser Ala Leu Ser Thr Cys
  1               5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Cys Ser Asn Ala Ser Thr Cys
  1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Cys Ser Asn Leu Ala Thr Cys
  1               5

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Cys Ser Asn Leu Ser Ala Cys
  1               5

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Lys Cys Asn Thr Ala Thr Cys
  1               5

<210> SEQ ID NO 28
<211> LENGTH: 15
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 28

Leu Leu Gln Gln Leu Gln Lys Leu Leu Gln Lys Leu Lys Gln Tyr
 1               5                  10                  15

<210> SEQ ID NO 29
<211> LENGTH: 28
<212> TYPE: PRT
<213> ORGANISM: Artificial Sequence
<220> FEATURE:
<223> OTHER INFORMATION: Description of Artificial Sequence: Synthetic
      amino acid sequence
<220> FEATURE:
<221> NAME/KEY: MOD_RES
<222> LOCATION: (1)..(4)
<223> OTHER INFORMATION: This region may encompass 1-4 Any amino acids
<220> FEATURE:
<221> NAME/KEY: MOD_RES
<222> LOCATION: (7)
<223> OTHER INFORMATION: Gly or Aib
<220> FEATURE:
<221> NAME/KEY: MOD_RES
<222> LOCATION: (8)
<223> OTHER INFORMATION: Lys, Arg, Orn, hArg, Cit, hLys, or Lys(for)
<220> FEATURE:
<221> NAME/KEY: MOD_RES
<222> LOCATION: (12)
<223> OTHER INFORMATION: Glu or Phe
<220> FEATURE:
<221> NAME/KEY: MOD_RES
<222> LOCATION: (14)
<223> OTHER INFORMATION: His or Aib
<220> FEATURE:
<221> NAME/KEY: MOD_RES
<222> LOCATION: (15)
<223> OTHER INFORMATION: Lys, Arg, Orn, hArg, Cit, hLys, Lys(for),
      or Lys(PEG5000)
<220> FEATURE:
<221> NAME/KEY: MOD_RES
<222> LOCATION: (19)
<223> OTHER INFORMATION: Tyr or Leu
<220> FEATURE:
<221> NAME/KEY: MOD_RES
<222> LOCATION: (21)
<223> OTHER INFORMATION: Arg or Pro
<220> FEATURE:
<221> NAME/KEY: MOD_RES
<222> LOCATION: (25)..(28)
<223> OTHER INFORMATION: This region may encompass 1-4 Any amino acids

<400> SEQUENCE: 29

Xaa Xaa Xaa Xaa Val Leu Xaa Xaa Leu Ser Gln Xaa Leu Xaa Xaa Leu
 1               5                  10                  15

Gln Thr Xaa Pro Xaa Thr Asn Thr Xaa Xaa Xaa Xaa
                20                  25

<210> SEQ ID NO 30
<211> LENGTH: 28
<212> TYPE: PRT
<213> ORGANISM: Artificial Sequence
<220> FEATURE:
<223> OTHER INFORMATION: Description of Artificial Sequence: Synthetic
      amino acid sequence
<220> FEATURE:
<221> NAME/KEY: MOD_RES
<222> LOCATION: (1)..(4)
<223> OTHER INFORMATION: This region may encompass 1-4 Any amino acid
      residues
<220> FEATURE:
<221> NAME/KEY: MOD_RES
<222> LOCATION: (5)
<223> OTHER INFORMATION: Ala or Val
<220> FEATURE:
```

```
<221> NAME/KEY: MOD_RES
<222> LOCATION: (6)
<223> OTHER INFORMATION: Thr, Met, or Leu
<220> FEATURE:
<221> NAME/KEY: MOD_RES
<222> LOCATION: (7)
<223> OTHER INFORMATION: Gln, Gly, or His
<220> FEATURE:
<221> NAME/KEY: MOD_RES
<222> LOCATION: (9)
<223> OTHER INFORMATION: Leu or Thr
<220> FEATURE:
<221> NAME/KEY: MOD_RES
<222> LOCATION: (10)
<223> OTHER INFORMATION: Ala, Thr, Asn, Phe, Tyr, Ser, or Thr
<220> FEATURE:
<221> NAME/KEY: MOD_RES
<222> LOCATION: (11)
<223> OTHER INFORMATION: Asn, Arg, Ala, Asp, Glu, Gln, Thr, or Gly
<220> FEATURE:
<221> NAME/KEY: MOD_RES
<222> LOCATION: (12)
<223> OTHER INFORMATION: Phe, Leu, Ser, Glu, Ala, Asp, or Tyr
<220> FEATURE:
<221> NAME/KEY: MOD_RES
<222> LOCATION: (13)
<223> OTHER INFORMATION: Leu or Asp
<220> FEATURE:
<221> NAME/KEY: MOD_RES
<222> LOCATION: (14)
<223> OTHER INFORMATION: Val, His, Ser, Phe, or Aib
<220> FEATURE:
<221> NAME/KEY: MOD_RES
<222> LOCATION: (15)
<223> OTHER INFORMATION: His, Arg, Lys, Orn, hArg, Cit, hLys, Lys(for),
      or Lys(PEG5000)
<220> FEATURE:
<221> NAME/KEY: MOD_RES
<222> LOCATION: (16)
<223> OTHER INFORMATION: Leu, Ser, or Phe
<220> FEATURE:
<221> NAME/KEY: MOD_RES
<222> LOCATION: (17)
<223> OTHER INFORMATION: Gln or His
<220> FEATURE:
<221> NAME/KEY: MOD_RES
<222> LOCATION: (18)
<223> OTHER INFORMATION: Thr or Asn
<220> FEATURE:
<221> NAME/KEY: MOD_RES
<222> LOCATION: (19)
<223> OTHER INFORMATION: Tyr, Val, Phe, Leu, or Met
<220> FEATURE:
<221> NAME/KEY: MOD_RES
<222> LOCATION: (21)
<223> OTHER INFORMATION: Arg or Pro
<220> FEATURE:
<221> NAME/KEY: MOD_RES
<222> LOCATION: (25)..(28)
<223> OTHER INFORMATION: This region may encompass 1-4 Any amino acid
      residues

<400> SEQUENCE: 30

Xaa Xaa Xaa Xaa Xaa Xaa Xaa Arg Xaa Xaa Xaa Xaa Xaa Xaa Xaa Xaa
 1               5                  10                  15

Xaa Xaa Xaa Pro Xaa Thr Asn Thr Xaa Xaa Xaa Xaa
            20                  25

<210> SEQ ID NO 31
<211> LENGTH: 11
<212> TYPE: PRT
<213> ORGANISM: Artificial Sequence
<220> FEATURE:
<223> OTHER INFORMATION: Description of Artificial Sequence: Synthetic
      C-terminal amino acid sequence
<220> FEATURE:
<221> NAME/KEY: MOD_RES
```

```
<222> LOCATION: (1)
<223> OTHER INFORMATION: Lys, Tyr, or not present
<220> FEATURE:
<221> NAME/KEY: MOD_RES
<222> LOCATION: (2)
<223> OTHER INFORMATION: Ser, Pro, or not present
<220> FEATURE:
<221> NAME/KEY: MOD_RES
<222> LOCATION: (3)
<223> OTHER INFORMATION: Ser, Pro, Arg, or not present
<220> FEATURE:
<221> NAME/KEY: MOD_RES
<222> LOCATION: (4)
<223> OTHER INFORMATION: Thr or not present
<220> FEATURE:
<221> NAME/KEY: MOD_RES
<222> LOCATION: (5)
<223> OTHER INFORMATION: Asn or not present
<220> FEATURE:
<221> NAME/KEY: MOD_RES
<222> LOCATION: (6)
<223> OTHER INFORMATION: Val, Thr, or not present
<220> FEATURE:
<221> NAME/KEY: MOD_RES
<222> LOCATION: (8)
<223> OTHER INFORMATION: Ser or Glu
<220> FEATURE:
<221> NAME/KEY: MOD_RES
<222> LOCATION: (9)
<223> OTHER INFORMATION: Asn, Lys, or Gly
<220> FEATURE:
<221> NAME/KEY: MOD_RES
<222> LOCATION: (10)
<223> OTHER INFORMATION: Thr, Phe, or Ala
<220> FEATURE:
<221> NAME/KEY: MOD_RES
<222> LOCATION: (11)
<223> OTHER INFORMATION: Tyr, Phe, Pro, or not present

<400> SEQUENCE: 31

Xaa Xaa Xaa Xaa Xaa Xaa Gly Xaa Xaa Xaa Xaa
  1               5                  10

<210> SEQ ID NO 32
<211> LENGTH: 8
<212> TYPE: PRT
<213> ORGANISM: Artificial Sequence
<220> FEATURE:
<223> OTHER INFORMATION: Description of Artificial Sequence: Synthetic
      C-terminal amino acid sequence

<400> SEQUENCE: 32

Lys Ser Asn Phe Val Pro Thr Asn
  1               5

<210> SEQ ID NO 33
<211> LENGTH: 8
<212> TYPE: PRT
<213> ORGANISM: Artificial Sequence
<220> FEATURE:
<223> OTHER INFORMATION: Description of Artificial Sequence: Synthetic
      C-terminal amino acid sequence

<400> SEQUENCE: 33

Ser Asn Phe Val Pro Thr Asn Val
  1               5

<210> SEQ ID NO 34
<211> LENGTH: 32
<212> TYPE: PRT
<213> ORGANISM: Artificial Sequence
<220> FEATURE:
<223> OTHER INFORMATION: Description of Artificial Sequence: Synthetic
      amino acid sequence
```

-continued

```
<220> FEATURE:
<221> NAME/KEY: MOD_RES
<222> LOCATION: (1)
<223> OTHER INFORMATION: Any amino acid, hCys, hLys, hArg, Hse, Hyp,
      or not present
<220> FEATURE:
<221> NAME/KEY: MOD_RES
<222> LOCATION: (2)
<223> OTHER INFORMATION: Any amino acid; see
      specification as filed for detailed description
      of substitutions and preferred embodiments
<220> FEATURE:
<221> NAME/KEY: MOD_RES
<222> LOCATION: (3)
<223> OTHER INFORMATION: Ala, Asp, Glu, Asn, Gln, Gly, Val, Arg, Lys,
      hLys, hArg, His, Ile, Leu, Met, or not present
<220> FEATURE:
<221> NAME/KEY: MOD_RES
<222> LOCATION: (4)
<223> OTHER INFORMATION: Ala, Ile, Leu, Ser, Hse, Thr, Val, Met, or not
      present
<220> FEATURE:
<221> NAME/KEY: MOD_RES
<222> LOCATION: (5)
<223> OTHER INFORMATION: Ala, Ser, Thr, Hse, Tyr, Val, Ile, Leu, or Met
<220> FEATURE:
<221> NAME/KEY: MOD_RES
<222> LOCATION: (6)
<223> OTHER INFORMATION: Thr, Ala, Ser, Hse, Tyr, Val, Ile, Leu, or Met
<220> FEATURE:
<221> NAME/KEY: MOD_RES
<222> LOCATION: (7)
<223> OTHER INFORMATION: Any amino acid; see
      specification as filed for detailed description
      of substitutions and preferred embodiments
<220> FEATURE:
<221> NAME/KEY: MOD_RES
<222> LOCATION: (8)
<223> OTHER INFORMATION: Ala, Val, Ile, Leu, Phe, or Met
<220> FEATURE:
<221> NAME/KEY: MOD_RES
<222> LOCATION: (9)
<223> OTHER INFORMATION: Leu, Thr, Ser, Hse, Val, Ile, or Met
<220> FEATURE:
<221> NAME/KEY: MOD_RES
<222> LOCATION: (10)
<223> OTHER INFORMATION: Gly, His, Gln, Lys, Arg, Asn, hLys, or hArg
<220> FEATURE:
<221> NAME/KEY: MOD_RES
<222> LOCATION: (11)
<223> OTHER INFORMATION: Lys, Arg, Gln, Asn, hLys, hArg, or His
<220> FEATURE:
<221> NAME/KEY: MOD_RES
<222> LOCATION: (12)
<223> OTHER INFORMATION: Leu, Ile, Val, Phe, Met, Trp, or Tyr
<220> FEATURE:
<221> NAME/KEY: MOD_RES
<222> LOCATION: (13)
<223> OTHER INFORMATION: Ala, Phe, Tyr, Asn, Gln, Ser, Hse, or Thr
<220> FEATURE:
<221> NAME/KEY: MOD_RES
<222> LOCATION: (14)
<223> OTHER INFORMATION: Ala, Asp, Glu, Gly, Asn, Lys, Gln, Arg, His,
      hArg, or hLys
<220> FEATURE:
<221> NAME/KEY: MOD_RES
<222> LOCATION: (15)
<223> OTHER INFORMATION: Ala, Asp, Glu, Phe, Leu, Ser, Tyr, Ile, Val, or
      Met
<220> FEATURE:
<221> NAME/KEY: MOD_RES
<222> LOCATION: (16)
<223> OTHER INFORMATION: Leu, Phe, Met, Val, Tyr, or Ile
<220> FEATURE:
<221> NAME/KEY: MOD_RES
<222> LOCATION: (17)
<223> OTHER INFORMATION: His, Gln, Asn, Ser, Hse, Thr, or Val
<220> FEATURE:
<221> NAME/KEY: MOD_RES
<222> LOCATION: (18)
```

```
<223> OTHER INFORMATION: Lys, hLys, Arg, hArg, His, Cit, or Orn
<220> FEATURE:
<221> NAME/KEY: MOD_RES
<222> LOCATION: (19)
<223> OTHER INFORMATION: Phe, Leu, Ser, Hse, Val, Ile, Thr, or not
      present
<220> FEATURE:
<221> NAME/KEY: MOD_RES
<222> LOCATION: (20)
<223> OTHER INFORMATION: His, Arg, Lys, hArg, hLys, Asn, Gln, or not
      present
<220> FEATURE:
<221> NAME/KEY: MOD_RES
<222> LOCATION: (21)
<223> OTHER INFORMATION: Thr, Ser, Hse, Val, Ile, Leu, Gln, Asn, or not
      present
<220> FEATURE:
<221> NAME/KEY: MOD_RES
<222> LOCATION: (22)
<223> OTHER INFORMATION: Phe, Leu, Met, Val, Tyr, or Ile
<220> FEATURE:
<221> NAME/KEY: MOD_RES
<222> LOCATION: (23)
<223> OTHER INFORMATION: Pro or Hyp
<220> FEATURE:
<221> NAME/KEY: MOD_RES
<222> LOCATION: (24)
<223> OTHER INFORMATION: Pro, Hyp, Arg, Lys, hArg, hLys, or His
<220> FEATURE:
<221> NAME/KEY: MOD_RES
<222> LOCATION: (25)
<223> OTHER INFORMATION: Thr, Ser, Hse, Val, Ile, Leu, Phe, or Tyr
<220> FEATURE:
<221> NAME/KEY: MOD_RES
<222> LOCATION: (26)
<223> OTHER INFORMATION: Asn, Gln, Asp, or Glu
<220> FEATURE:
<221> NAME/KEY: MOD_RES
<222> LOCATION: (27)
<223> OTHER INFORMATION: Thr, Val, Ser, Phe, Ile, or Leu
<220> FEATURE:
<221> NAME/KEY: MOD_RES
<222> LOCATION: (28)
<223> OTHER INFORMATION: Gly or Ala
<220> FEATURE:
<221> NAME/KEY: MOD_RES
<222> LOCATION: (29)
<223> OTHER INFORMATION: Ser, Hse, Thr, Val, Ile, Leu, or Tyr
<220> FEATURE:
<221> NAME/KEY: MOD_RES
<222> LOCATION: (30)
<223> OTHER INFORMATION: Glu, Gly, Lys, Asn, Asp, Arg, hArg, hLys, His,
      or Gln
<220> FEATURE:
<221> NAME/KEY: MOD_RES
<222> LOCATION: (31)
<223> OTHER INFORMATION: Ala, Thr, Ser, Hse, Val, Ile Leu, Phe, or Tyr
<220> FEATURE:
<221> NAME/KEY: MOD_RES
<222> LOCATION: (32)
<223> OTHER INFORMATION: Phe, Pro, Tyr, Hse, Ser, Thr, or Hyp

<400> SEQUENCE: 34

Xaa Xaa Xaa Xaa Xaa Xaa Xaa Xaa Xaa Xaa Xaa Xaa Xaa Xaa Xaa Xaa
 1               5                   10                  15

Xaa Xaa Xaa Xaa Xaa Xaa Xaa Xaa Xaa Xaa Xaa Xaa Xaa Xaa Xaa Xaa
            20                  25                  30

<210> SEQ ID NO 35
<211> LENGTH: 32
<212> TYPE: PRT
<213> ORGANISM: Artificial Sequence
<220> FEATURE:
<223> OTHER INFORMATION: Description of Artificial Sequence: Synthetic
      amino acid sequence
<220> FEATURE:
<221> NAME/KEY: MOD_RES
```

```
<222> LOCATION: (1)
<223> OTHER INFORMATION: Ala, Cys, Asp, Phe, Ile, Lys, Ser, Thr, or not
      present
<220> FEATURE:
<221> NAME/KEY: MOD_RES
<222> LOCATION: (2)
<223> OTHER INFORMATION: Cys, Asp, Ser, or not present
<220> FEATURE:
<221> NAME/KEY: MOD_RES
<222> LOCATION: (3)
<223> OTHER INFORMATION: Ala, Asp, Asn, or not present
<220> FEATURE:
<221> NAME/KEY: MOD_RES
<222> LOCATION: (4)
<223> OTHER INFORMATION: Ala, Leu Thr, or not present
<220> FEATURE:
<221> NAME/KEY: MOD_RES
<222> LOCATION: (5)
<223> OTHER INFORMATION: Ala or Ser
<220> FEATURE:
<221> NAME/KEY: MOD_RES
<222> LOCATION: (6)
<223> OTHER INFORMATION: Thr, Ala, Ser, or Val
<220> FEATURE:
<221> NAME/KEY: MOD_RES
<222> LOCATION: (7)
<223> OTHER INFORMATION: Cys, Lys, or Ala
<220> FEATURE:
<221> NAME/KEY: MOD_RES
<222> LOCATION: (8)
<223> OTHER INFORMATION: Ala, Val, Leu, or Met
<220> FEATURE:
<221> NAME/KEY: MOD_RES
<222> LOCATION: (9)
<223> OTHER INFORMATION: Leu or Thr
<220> FEATURE:
<221> NAME/KEY: MOD_RES
<222> LOCATION: (10)
<223> OTHER INFORMATION: Gly, His, or Gln
<220> FEATURE:
<221> NAME/KEY: MOD_RES
<222> LOCATION: (11)
<223> OTHER INFORMATION: Lys, Arg, Gln, or hArg
<220> FEATURE:
<221> NAME/KEY: MOD_RES
<222> LOCATION: (12)
<223> OTHER INFORMATION: Leu, Trp, or Tyr
<220> FEATURE:
<221> NAME/KEY: MOD_RES
<222> LOCATION: (13)
<223> OTHER INFORMATION: Ala, Phe, Asn, Gln, Ser, or Thr
<220> FEATURE:
<221> NAME/KEY: MOD_RES
<222> LOCATION: (14)
<223> OTHER INFORMATION: Ala, Asp, Glu, Gly, Asn, Lys, Gln, or Arg
<220> FEATURE:
<221> NAME/KEY: MOD_RES
<222> LOCATION: (15)
<223> OTHER INFORMATION: Ala, Asp, Glu, Phe, Leu, Ser, or Tyr
<220> FEATURE:
<221> NAME/KEY: MOD_RES
<222> LOCATION: (16)
<223> OTHER INFORMATION: Leu or Phe
<220> FEATURE:
<221> NAME/KEY: MOD_RES
<222> LOCATION: (17)
<223> OTHER INFORMATION: His, Gln, Ser, or Val
<220> FEATURE:
<221> NAME/KEY: MOD_RES
<222> LOCATION: (18)
<223> OTHER INFORMATION: Lys, Arg, hArg, Cit, or Orn
<220> FEATURE:
<221> NAME/KEY: MOD_RES
<222> LOCATION: (19)
<223> OTHER INFORMATION: Phe, Leu, Ser, or not present
<220> FEATURE:
<221> NAME/KEY: MOD_RES
<222> LOCATION: (20)
<223> OTHER INFORMATION: His, Gln, or not present
<220> FEATURE:
```

-continued

```
<221> NAME/KEY: MOD_RES
<222> LOCATION: (21)
<223> OTHER INFORMATION: Thr, Asn, or not present
<220> FEATURE:
<221> NAME/KEY: MOD_RES
<222> LOCATION: (22)
<223> OTHER INFORMATION: Phe, Leu, Met, Val, or Tyr
<220> FEATURE:
<221> NAME/KEY: MOD_RES
<222> LOCATION: (24)
<223> OTHER INFORMATION: Pro or Arg
<220> FEATURE:
<221> NAME/KEY: MOD_RES
<222> LOCATION: (27)
<223> OTHER INFORMATION: Thr or Val
<220> FEATURE:
<221> NAME/KEY: MOD_RES
<222> LOCATION: (30)
<223> OTHER INFORMATION: Glu, Gly, Lys, or Asn
<220> FEATURE:
<221> NAME/KEY: MOD_RES
<222> LOCATION: (31)
<223> OTHER INFORMATION: Ala or Thr
<220> FEATURE:
<221> NAME/KEY: MOD_RES
<222> LOCATION: (32)
<223> OTHER INFORMATION: Phe, Pro, or Tyr

<400> SEQUENCE: 35

Xaa Xaa Xaa Xaa Xaa Xaa Xaa Xaa Xaa Xaa Xaa Xaa Xaa Xaa Xaa Xaa
 1               5                   10                  15

Xaa Xaa Xaa Xaa Xaa Xaa Pro Xaa Thr Asn Xaa Gly Ser Xaa Xaa Xaa
            20                  25                  30

<210> SEQ ID NO 36
<211> LENGTH: 32
<212> TYPE: PRT
<213> ORGANISM: Artificial Sequence
<220> FEATURE:
<223> OTHER INFORMATION: Description of Artificial Sequence: Synthetic
      amino acid sequence
<220> FEATURE:
<221> NAME/KEY: MOD_RES
<222> LOCATION: (1)
<223> OTHER INFORMATION: Ala, Cys, Phe, Ile, Lys, Ser, or not
      present
<220> FEATURE:
<221> NAME/KEY: MOD_RES
<222> LOCATION: (2)
<223> OTHER INFORMATION: Cys, Asp, or Ser
<220> FEATURE:
<221> NAME/KEY: MOD_RES
<222> LOCATION: (3)
<223> OTHER INFORMATION: Ala, Asp, or Asn
<220> FEATURE:
<221> NAME/KEY: MOD_RES
<222> LOCATION: (4)
<223> OTHER INFORMATION: Ala, Leu, or Thr
<220> FEATURE:
<221> NAME/KEY: MOD_RES
<222> LOCATION: (5)
<223> OTHER INFORMATION: Ala or Ser
<220> FEATURE:
<221> NAME/KEY: MOD_RES
<222> LOCATION: (7)
<223> OTHER INFORMATION: Cys or Lys
<220> FEATURE:
<221> NAME/KEY: MOD_RES
<222> LOCATION: (8)
<223> OTHER INFORMATION: Ala or Val
<220> FEATURE:
<221> NAME/KEY: MOD_RES
<222> LOCATION: (9)
<223> OTHER INFORMATION: Leu or Thr
<220> FEATURE:
<221> NAME/KEY: MOD_RES
<222> LOCATION: (10)
```

```
<223> OTHER INFORMATION: Gly, His, or Gln
<220> FEATURE:
<221> NAME/KEY: MOD_RES
<222> LOCATION: (11)
<223> OTHER INFORMATION: Lys, Arg, or hArg
<220> FEATURE:
<221> NAME/KEY: MOD_RES
<222> LOCATION: (13)
<223> OTHER INFORMATION: Ala, Phe, Asn, Ser, or Thr
<220> FEATURE:
<221> NAME/KEY: MOD_RES
<222> LOCATION: (14)
<223> OTHER INFORMATION: Ala, Asp, Glu, Gly, Asn, Gln, or Arg
<220> FEATURE:
<221> NAME/KEY: MOD_RES
<222> LOCATION: (15)
<223> OTHER INFORMATION: Ala, Glu, Phe, Leu, Ser, or Tyr
<220> FEATURE:
<221> NAME/KEY: MOD_RES
<222> LOCATION: (17)
<223> OTHER INFORMATION: His, Ser, or Val
<220> FEATURE:
<221> NAME/KEY: MOD_RES
<222> LOCATION: (18)
<223> OTHER INFORMATION: Lys, Arg, hArg, Cit, or Orn
<220> FEATURE:
<221> NAME/KEY: MOD_RES
<222> LOCATION: (19)
<223> OTHER INFORMATION: Phe, Leu, or Ser
<220> FEATURE:
<221> NAME/KEY: MOD_RES
<222> LOCATION: (20)
<223> OTHER INFORMATION: His or Gln
<220> FEATURE:
<221> NAME/KEY: MOD_RES
<222> LOCATION: (21)
<223> OTHER INFORMATION: Thr or Asn
<220> FEATURE:
<221> NAME/KEY: MOD_RES
<222> LOCATION: (22)
<223> OTHER INFORMATION: Phe, Leu, Met, Val, or Tyr
<220> FEATURE:
<221> NAME/KEY: MOD_RES
<222> LOCATION: (24)
<223> OTHER INFORMATION: Pro or Arg
<220> FEATURE:
<221> NAME/KEY: MOD_RES
<222> LOCATION: (27)
<223> OTHER INFORMATION: Thr or Val
<220> FEATURE:
<221> NAME/KEY: MOD_RES
<222> LOCATION: (30)
<223> OTHER INFORMATION: Glu, Gly, Lys, or Asn
<220> FEATURE:
<221> NAME/KEY: MOD_RES
<222> LOCATION: (31)
<223> OTHER INFORMATION: Ala or Thr
<220> FEATURE:
<221> NAME/KEY: MOD_RES
<222> LOCATION: (32)
<223> OTHER INFORMATION: Phe, Pro, or Tyr

<400> SEQUENCE: 36

Xaa Xaa Xaa Xaa Xaa Thr Xaa Xaa Xaa Xaa Xaa Leu Xaa Xaa Xaa Leu
 1               5                  10                  15

Xaa Xaa Xaa Xaa Xaa Xaa Pro Xaa Thr Asn Xaa Gly Ser Xaa Xaa Xaa
            20                  25                  30

<210> SEQ ID NO 37
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37
```

```
Gln Thr Tyr
  1

<210> SEQ ID NO 38
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Leu Gln Thr Tyr
  1

<210> SEQ ID NO 39
<211> LENGTH: 32
<212> TYPE: PRT
<213> ORGANISM: Artificial Sequence
<220> FEATURE:
<223> OTHER INFORMATION: Description of Artificial Sequence: Synthetic
      amino acid sequence
<220> FEATURE:
<221> NAME/KEY: MOD_RES
<222> LOCATION: (1)
<223> OTHER INFORMATION: Ala, Cys, Asp, Phe, Lys, Thr, or not
      present
<220> FEATURE:
<221> NAME/KEY: MOD_RES
<222> LOCATION: (2)
<223> OTHER INFORMATION: Ala, Cys, Asp, Ser, or not present
<220> FEATURE:
<221> NAME/KEY: MOD_RES
<222> LOCATION: (3)
<223> OTHER INFORMATION: Ala, Asp, Asn, or not present
<220> FEATURE:
<221> NAME/KEY: MOD_RES
<222> LOCATION: (4)
<223> OTHER INFORMATION: Ala, Leu Thr, or not present
<220> FEATURE:
<221> NAME/KEY: MOD_RES
<222> LOCATION: (5)
<223> OTHER INFORMATION: Ala or Ser
<220> FEATURE:
<221> NAME/KEY: MOD_RES
<222> LOCATION: (6)
<223> OTHER INFORMATION: Ala, Ser, Thr, or Val
<220> FEATURE:
<221> NAME/KEY: MOD_RES
<222> LOCATION: (7)
<223> OTHER INFORMATION: Ala, Cys, or Lys
<220> FEATURE:
<221> NAME/KEY: MOD_RES
<222> LOCATION: (8)
<223> OTHER INFORMATION: Ala, Leu, Met, or Val
<220> FEATURE:
<221> NAME/KEY: MOD_RES
<222> LOCATION: (9)
<223> OTHER INFORMATION: Leu or Thr
<220> FEATURE:
<221> NAME/KEY: MOD_RES
<222> LOCATION: (10)
<223> OTHER INFORMATION: Gly, His, or Gln
<220> FEATURE:
<221> NAME/KEY: MOD_RES
<222> LOCATION: (11)
<223> OTHER INFORMATION: Lys, Gln, or Arg
<220> FEATURE:
<221> NAME/KEY: MOD_RES
<222> LOCATION: (12)
<223> OTHER INFORMATION: Leu, Trp, or Tyr
<220> FEATURE:
<221> NAME/KEY: MOD_RES
<222> LOCATION: (13)
<223> OTHER INFORMATION: Ala, Asn, Gln, Ser, or Thr
<220> FEATURE:
```

```
<221> NAME/KEY: MOD_RES
<222> LOCATION: (14)
<223> OTHER INFORMATION: Ala, Asp, Glu, Gly, Lys, Asn, Gln, or Arg
<220> FEATURE:
<221> NAME/KEY: MOD_RES
<222> LOCATION: (15)
<223> OTHER INFORMATION: Ala, Asp, Glu, Phe, Leu, Ser, or Tyr
<220> FEATURE:
<221> NAME/KEY: MOD_RES
<222> LOCATION: (16)
<223> OTHER INFORMATION: Phe or Leu
<220> FEATURE:
<221> NAME/KEY: MOD_RES
<222> LOCATION: (17)
<223> OTHER INFORMATION: His, Gln, Ser, or Val
<220> FEATURE:
<221> NAME/KEY: MOD_RES
<222> LOCATION: (18)
<223> OTHER INFORMATION: Lys or Arg
<220> FEATURE:
<221> NAME/KEY: MOD_RES
<222> LOCATION: (19)
<223> OTHER INFORMATION: Phe, Leu, Ser, or not present
<220> FEATURE:
<221> NAME/KEY: MOD_RES
<222> LOCATION: (20)
<223> OTHER INFORMATION: His, Lys, Gln, or not present
<220> FEATURE:
<221> NAME/KEY: MOD_RES
<222> LOCATION: (21)
<223> OTHER INFORMATION: Gln, Thr, or not present
<220> FEATURE:
<221> NAME/KEY: MOD_RES
<222> LOCATION: (22)
<223> OTHER INFORMATION: Phe, Leu, or Tyr
<220> FEATURE:
<221> NAME/KEY: MOD_RES
<222> LOCATION: (24)
<223> OTHER INFORMATION: Pro or Arg
<220> FEATURE:
<221> NAME/KEY: MOD_RES
<222> LOCATION: (27)
<223> OTHER INFORMATION: Thr or Val
<220> FEATURE:
<221> NAME/KEY: MOD_RES
<222> LOCATION: (30)
<223> OTHER INFORMATION: Glu, Lys, or Asn
<220> FEATURE:
<221> NAME/KEY: MOD_RES
<222> LOCATION: (31)
<223> OTHER INFORMATION: Ala or Thr
<220> FEATURE:
<221> NAME/KEY: MOD_RES
<222> LOCATION: (32)
<223> OTHER INFORMATION: Phe, Tyr, or not present

<400> SEQUENCE: 39

Xaa Xaa Xaa Xaa Xaa Xaa Xaa Xaa Xaa Xaa Xaa Xaa Xaa Xaa Xaa Xaa
 1               5                   10                  15

Xaa Xaa Xaa Xaa Xaa Xaa Pro Xaa Thr Asn Xaa Gly Ser Xaa Xaa Xaa
                20                  25                  30

<210> SEQ ID NO 40
<211> LENGTH: 32
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 40

Lys Cys Asn Thr Ala Thr Cys Val Leu Gly Lys Leu Ser Gln Glu Leu
 1               5                   10                  15

His Arg Leu Gln Thr Tyr Pro Arg Thr Asn Thr Gly Ser Asn Thr Tyr
                20                  25                  30
```

<210> SEQ ID NO 41
<211> LENGTH: 32
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 41

Lys Cys Asn Thr Ala Thr Cys Val Leu Gly Arg Leu Ser Gln Glu Leu
 1               5                  10                  15

His Arg Leu Gln Thr Leu Pro Arg Thr Asn Thr Gly Ser Asn Thr Tyr
            20                  25                  30

<210> SEQ ID NO 42
<211> LENGTH: 32
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 42

Lys Cys Asn Thr Ala Thr Cys Val Leu Gly Arg Leu Ser Gln Glu Leu
 1               5                  10                  15

His Arg Leu Gln Thr Tyr Pro Pro Thr Asn Thr Gly Ser Asn Thr Tyr
            20                  25                  30

<210> SEQ ID NO 43
<211> LENGTH: 32
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 43

Lys Cys Asn Thr Ala Thr Cys Val Leu Gly Arg Leu Ser Gln Glu Leu
 1               5                  10                  15

His Arg Leu Gln Thr Tyr Pro Arg Thr Asn Val Gly Ser Asn Thr Tyr
            20                  25                  30

<210> SEQ ID NO 44
<211> LENGTH: 32
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 44

Lys Cys Asn Thr Ala Thr Cys Val Leu Gly Arg Leu Ser Gln Glu Leu
 1               5                  10                  15

His Arg Leu Gln Thr Leu Pro Pro Thr Asn Val Gly Ser Asn Thr Tyr
            20                  25                  30

<210> SEQ ID NO 45
<211> LENGTH: 32
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 45

Lys Cys Asn Thr Ala Thr Cys Val Leu Gly Arg Leu Ala Asn Phe Leu
1               5                   10                  15

His Arg Leu Gln Thr Tyr Pro Arg Thr Asn Thr Gly Ser Asn Thr Tyr
            20                  25                  30

<210> SEQ ID NO 46
<211> LENGTH: 32
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 46

Ala Cys Asn Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 47
<211> LENGTH: 32
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 47

Lys Cys Asn Ala Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 48
<211> LENGTH: 32
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 48

Lys Cys Asn Thr Ala Ala Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 49
<211> LENGTH: 32
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 49

Cys Ala Asn Leu Ser Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 50
<211> LENGTH: 28
<212> TYPE: PRT
<213> ORGANISM: Artificial Sequence
<220> FEATURE:

-continued

```
<223> OTHER INFORMATION: Description of Artificial Sequence: Synthetic
      amino acid sequence
<220> FEATURE:
<221> NAME/KEY: MOD_RES
<222> LOCATION: (1)..(1)
<223> OTHER INFORMATION: Isocaproyl-Ser

<400> SEQUENCE: 50

Ser Thr Ala Val Leu Gly Arg Leu Ser Gln Glu Leu His Arg Leu Gln
1               5                   10                  15

Thr Tyr Pro Arg Thr Asn Thr Gly Ser Asn Thr Tyr
            20                  25

<210> SEQ ID NO 51
<211> LENGTH: 32
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 51

Cys Ser Asn Ala Ser Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 52
<211> LENGTH: 32
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 52

Cys Ser Asn Leu Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 53
<211> LENGTH: 32
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 53

Cys Ser Asn Leu Ser Ala Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 54
<211> LENGTH: 32
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 54

Lys Cys Asn Thr Ala Thr Cys Val Leu Gly Arg Leu Ser Gln Glu Leu
1               5                   10                  15
```

```
His Lys Leu Gln Thr Tyr Pro Arg Thr Asn Thr Gly Ser Asn Thr Tyr
            20                  25                  30

<210> SEQ ID NO 55
<211> LENGTH: 32
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 55

Lys Cys Asn Thr Ala Thr Cys Val Leu Gly Arg Leu Ser Gln Glu Leu
  1               5                  10                  15

His Arg Leu Gln Thr Tyr Pro Arg Thr Asn Thr Gly Ser Gly Thr Pro
            20                  25                  30

<210> SEQ ID NO 56
<211> LENGTH: 32
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 56

Cys Ser Ala Leu Ser Thr Cys Val Leu Gly Arg Leu Ser Gln Glu Leu
  1               5                  10                  15

His Arg Leu Gln Thr Tyr Pro Arg Thr Asn Thr Gly Ser Asn Thr Tyr
            20                  25                  30

<210> SEQ ID NO 57
<211> LENGTH: 32
<212> TYPE: PRT
<213> ORGANISM: Artificial Sequence
<220> FEATURE:
<223> OTHER INFORMATION: Description of Artificial Sequence: Synthetic
      amino acid sequence
<220> FEATURE:
<221> NAME/KEY: MOD_RES
<222> LOCATION: (1)
<223> OTHER INFORMATION: Ac-Agy
<220> FEATURE:
<221> NAME/KEY: MOD_RES
<222> LOCATION: (7)
<223> OTHER INFORMATION: Agy

<400> SEQUENCE: 57

Xaa Ser Asn Leu Ser Thr Xaa Val Leu Gly Arg Leu Ser Gln Glu Leu
  1               5                  10                  15

His Arg Leu Gln Thr Tyr Pro Arg Thr Asn Thr Gly Ser Asn Thr Tyr
            20                  25                  30

<210> SEQ ID NO 58
<211> LENGTH: 32
<212> TYPE: PRT
<213> ORGANISM: Artificial Sequence
<220> FEATURE:
<223> OTHER INFORMATION: Description of Artificial Sequence: Synthetic
      amino acid sequence
<220> FEATURE:
<221> NAME/KEY: MOD_RES
<222> LOCATION: (1)
<223> OTHER INFORMATION: Ac-Lys
<220> FEATURE:
<221> NAME/KEY: MOD_RES
<222> LOCATION: (2)
<223> OTHER INFORMATION: Agy
<220> FEATURE:
<221> NAME/KEY: MOD_RES
```

```
<222> LOCATION: (7)
<223> OTHER INFORMATION: Agy

<400> SEQUENCE: 58

Lys Xaa Asn Thr Ala Thr Xaa Val Leu Gly Arg Leu Ser Gln Glu Leu
 1               5                  10                  15

His Arg Leu Gln Thr Tyr Pro Arg Thr Asn Thr Gly Ser Asn Thr Tyr
             20                  25                  30

<210> SEQ ID NO 59
<211> LENGTH: 27
<212> TYPE: PRT
<213> ORGANISM: Artificial Sequence
<220> FEATURE:
<223> OTHER INFORMATION: Description of Artificial Sequence: Synthetic
      amino acid sequence
<220> FEATURE:
<221> NAME/KEY: MOD_RES
<222> LOCATION: (1)
<223> OTHER INFORMATION: Isocaproyl-Ser
<220> FEATURE:
<221> NAME/KEY: MOD_RES
<222> LOCATION: (6)
<223> OTHER INFORMATION: Aib

<400> SEQUENCE: 59

Ser Thr Ala Val Leu Xaa Arg Leu Ser Gln Glu Leu Arg Leu Gln Thr
 1               5                  10                  15

Tyr Pro Arg Thr Asn Thr Gly Ser Gly Thr Pro
             20                  25

<210> SEQ ID NO 60
<211> LENGTH: 28
<212> TYPE: PRT
<213> ORGANISM: Artificial Sequence
<220> FEATURE:
<223> OTHER INFORMATION: Description of Artificial Sequence: Synthetic
      amino acid sequence
<220> FEATURE:
<221> NAME/KEY: MOD_RES
<222> LOCATION: (1)
<223> OTHER INFORMATION: Isocaproyl-Ser
<220> FEATURE:
<221> NAME/KEY: MOD_RES
<222> LOCATION: (7)
<223> OTHER INFORMATION: Lys(For)
<220> FEATURE:
<221> NAME/KEY: MOD_RES
<222> LOCATION: (14)
<223> OTHER INFORMATION: Lys(For)

<400> SEQUENCE: 60

Ser Thr Ala Val Leu Gly Lys Leu Ser Gln Glu Leu His Lys Leu Gln
 1               5                  10                  15

Thr Tyr Pro Arg Thr Asn Thr Gly Ser Gly Thr Pro
             20                  25

<210> SEQ ID NO 61
<211> LENGTH: 28
<212> TYPE: PRT
<213> ORGANISM: Artificial Sequence
<220> FEATURE:
<223> OTHER INFORMATION: Description of Artificial Sequence: Synthetic
      amino acid sequence
<220> FEATURE:
<221> NAME/KEY: MOD_RES
<222> LOCATION: (1)
<223> OTHER INFORMATION: Isocaproyl-Ser
<220> FEATURE:
<221> NAME/KEY: MOD_RES
<222> LOCATION: (6)
```

```
<223> OTHER INFORMATION: Aib
<220> FEATURE:
<221> NAME/KEY: MOD_RES
<222> LOCATION: (7)
<223> OTHER INFORMATION: Lys(For)
<220> FEATURE:
<221> NAME/KEY: MOD_RES
<222> LOCATION: (13)
<223> OTHER INFORMATION: Aib
<220> FEATURE:
<221> NAME/KEY: MOD_RES
<222> LOCATION: (14)
<223> OTHER INFORMATION: Lys(For)

<400> SEQUENCE: 61

Ser Thr Ala Val Leu Xaa Lys Leu Ser Gln Glu Leu Xaa Lys Leu Gln
 1               5                  10                  15

Thr Tyr Pro Arg Thr Asn Thr Gly Ser Asn Thr Tyr
            20                  25

<210> SEQ ID NO 62
<211> LENGTH: 28
<212> TYPE: PRT
<213> ORGANISM: Artificial Sequence
<220> FEATURE:
<223> OTHER INFORMATION: Description of Artificial Sequence: Synthetic
      amino acid sequence
<220> FEATURE:
<221> NAME/KEY: MOD_RES
<222> LOCATION: (1)
<223> OTHER INFORMATION: Isocaproyl-Ser
<220> FEATURE:
<221> NAME/KEY: MOD_RES
<222> LOCATION: (6)
<223> OTHER INFORMATION: Aib
<220> FEATURE:
<221> NAME/KEY: MOD_RES
<222> LOCATION: (7)
<223> OTHER INFORMATION: Lys(For)
<220> FEATURE:
<221> NAME/KEY: MOD_RES
<222> LOCATION: (13)
<223> OTHER INFORMATION: Aib
<220> FEATURE:
<221> NAME/KEY: MOD_RES
<222> LOCATION: (14)
<223> OTHER INFORMATION: Lys(For)

<400> SEQUENCE: 62

Ser Thr Ala Val Leu Xaa Lys Leu Ser Gln Glu Leu Xaa Lys Leu Gln
 1               5                  10                  15

Thr Tyr Pro Arg Thr Asn Val Gly Ser Asn Thr Tyr
            20                  25

<210> SEQ ID NO 63
<211> LENGTH: 32
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 63

Lys Cys Asn Thr Ala Thr Cys Leu Leu Gln Gln Leu Gln Lys Leu Leu
 1               5                  10                  15

Gln Lys Leu Lys Gln Tyr Pro Arg Thr Asn Thr Gly Ser Asn Thr Tyr
            20                  25                  30

<210> SEQ ID NO 64
<211> LENGTH: 32
<212> TYPE: PRT
```

```
<213> ORGANISM: Artificial Sequence
<220> FEATURE:
<223> OTHER INFORMATION: Description of Artificial Sequence: Synthetic
      amino acid sequence

<400> SEQUENCE: 64

Lys Cys Asn Thr Ala Ser Cys Val Leu Gly Arg Leu Ser Gln Glu Leu
 1               5                  10                  15

His Arg Leu Gln Thr Tyr Pro Arg Thr Asn Thr Gly Ser Asn Thr Tyr
            20                  25                  30

<210> SEQ ID NO 65
<211> LENGTH: 32
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 65

Lys Cys Asn Thr Ala Val Cys Val Leu Gly Arg Leu Ser Gln Glu Leu
 1               5                  10                  15

His Arg Leu Gln Thr Tyr Pro Arg Thr Asn Thr Gly Ser Asn Thr Tyr
            20                  25                  30

<210> SEQ ID NO 66
<211> LENGTH: 29
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 66

Lys Cys Asn Thr Ala Thr Cys Val Leu Gly Arg Leu Ser Gln Glu Leu
 1               5                  10                  15

His Arg Tyr Pro Arg Thr Asn Thr Gly Ser Asn Thr Tyr
            20                  25

<210> SEQ ID NO 67
<211> LENGTH: 32
<212> TYPE: PRT
<213> ORGANISM: Artificial Sequence
<220> FEATURE:
<223> OTHER INFORMATION: Description of Artificial Sequence: Synthetic
      amino acid sequence
<220> FEATURE:
<221> NAME/KEY: MOD_RES
<222> LOCATION: (11)
<223> OTHER INFORMATION: Lys(For)
<220> FEATURE:
<221> NAME/KEY: MOD_RES
<222> LOCATION: (18)
<223> OTHER INFORMATION: Lys(For)

<400> SEQUENCE: 67

Lys Cys Asn Thr Ala Thr Cys Val Leu Gly Lys Leu Ser Gln Glu Leu
 1               5                  10                  15

His Lys Leu Gln Thr Tyr Pro Arg Thr Asn Thr Gly Ser Asn Thr Tyr
            20                  25                  30

<210> SEQ ID NO 68
<211> LENGTH: 32
<212> TYPE: PRT
<213> ORGANISM: Artificial Sequence
<220> FEATURE:
<223> OTHER INFORMATION: Description of Artificial Sequence: Synthetic
      amino acid sequence
```

```
<220> FEATURE:
<221> NAME/KEY: MOD_RES
<222> LOCATION: (6)
<223> OTHER INFORMATION: D-Thr

<400> SEQUENCE: 68

Lys Cys Asn Thr Ala Thr Cys Val Leu Gly Arg Leu Ser Gln Glu Leu
  1               5                  10                  15

His Arg Leu Gln Thr Tyr Pro Arg Thr Asn Thr Gly Ser Asn Thr Tyr
             20                  25                  30

<210> SEQ ID NO 69
<211> LENGTH: 32
<212> TYPE: PRT
<213> ORGANISM: Artificial Sequence
<220> FEATURE:
<223> OTHER INFORMATION: Description of Artificial Sequence: Synthetic
      amino acid sequence
<220> FEATURE:
<221> NAME/KEY: MOD_RES
<222> LOCATION: (6)
<223> OTHER INFORMATION: dAh

<400> SEQUENCE: 69

Lys Cys Asn Thr Ala Xaa Cys Val Leu Gly Arg Leu Ser Gln Glu Leu
  1               5                  10                  15

His Arg Leu Gln Thr Tyr Pro Arg Thr Asn Thr Gly Ser Asn Thr Tyr
             20                  25                  30

<210> SEQ ID NO 70
<211> LENGTH: 32
<212> TYPE: PRT
<213> ORGANISM: Artificial Sequence
<220> FEATURE:
<223> OTHER INFORMATION: Description of Artificial Sequence: Synthetic
      amino acid sequence
<220> FEATURE:
<221> NAME/KEY: MOD_RES
<222> LOCATION: (1)
<223> OTHER INFORMATION: Ac-Ala
<220> FEATURE:
<221> NAME/KEY: MOD_RES
<222> LOCATION: (18)
<223> OTHER INFORMATION: Lys(PEG5000)

<400> SEQUENCE: 70

Ala Cys Asn Thr Ala Thr Cys Val Leu Gly Arg Leu Ser Gln Glu Leu
  1               5                  10                  15

His Lys Leu Gln Thr Tyr Pro Arg Thr Asn Thr Gly Ser Asn Thr Tyr
             20                  25                  30

<210> SEQ ID NO 71
<211> LENGTH: 35
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 71

Lys Cys Asn Thr Ala Thr Cys Val Leu Gly Arg Leu Ser Gln Glu Leu
  1               5                  10                  15

His Arg Leu Gln Thr Leu Gln Thr Tyr Pro Arg Thr Asn Thr Gly Ser
             20                  25                  30

Asn Thr Tyr
         35
```

-continued

```
<210> SEQ ID NO 72
<211> LENGTH: 36
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 72

Lys Cys Asn Thr Ala Thr Cys Val Leu Gly Arg Leu Ser Gln Glu Leu
1               5                   10                  15

His Arg Leu Gln Thr Leu Leu Gln Thr Tyr Pro Arg Thr Asn Thr Gly
            20                  25                  30

Ser Asn Thr Tyr
        35

<210> SEQ ID NO 73
<211> LENGTH: 32
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 73

Lys Cys Asn Thr Ala Thr Cys Val Leu Gly Lys Leu Ser Gln Glu Leu
1               5                   10                  15

His Lys Leu Gln Thr Tyr Pro Arg Thr Asn Thr Gly Ser Asn Thr Tyr
            20                  25                  30

<210> SEQ ID NO 74
<211> LENGTH: 32
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 74

Lys Cys Asn Thr Ser Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 75
<211> LENGTH: 32
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 75

Lys Cys Asn Thr Ala Thr Cys Ala Thr Gln Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 76
<211> LENGTH: 32
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 76
```

```
Lys Cys Asn Thr Ala Thr Cys Ala Thr Gln Arg Leu Ser Gln Glu Leu
 1               5                  10                  15

His Arg Leu Gln Thr Tyr Pro Arg Thr Asn Val Gly Ser Asn Thr Tyr
                 20                  25                  30

<210> SEQ ID NO 77
<211> LENGTH: 32
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 77

Lys Cys Asn Thr Ser Thr Cys Ala Thr Gln Arg Leu Ala Asn Glu Leu
 1               5                  10                  15

Val Arg Leu Gln Thr Tyr Pro Arg Thr Asn Val Gly Ser Asn Thr Tyr
                 20                  25                  30

<210> SEQ ID NO 78
<211> LENGTH: 32
<212> TYPE: PRT
<213> ORGANISM: Artificial Sequence
<220> FEATURE:
<223> OTHER INFORMATION: Description of Artificial Sequence: Synthetic
      amino acid sequence
<220> FEATURE:
<221> NAME/KEY: MOD_RES
<222> LOCATION: (6)
<223> OTHER INFORMATION: Hse

<400> SEQUENCE: 78

Lys Cys Asn Thr Ala Xaa Cys Val Leu Gly Arg Leu Ser Gln Glu Leu
 1               5                  10                  15

His Arg Leu Gln Thr Tyr Pro Arg Thr Asn Thr Gly Ser Asn Thr Tyr
                 20                  25                  30

<210> SEQ ID NO 79
<211> LENGTH: 32
<212> TYPE: PRT
<213> ORGANISM: Artificial Sequence
<220> FEATURE:
<223> OTHER INFORMATION: Description of Artificial Sequence: Synthetic
      amino acid sequence
<220> FEATURE:
<221> NAME/KEY: MOD_RES
<222> LOCATION: (6)
<223> OTHER INFORMATION: Ahb

<400> SEQUENCE: 79

Lys Cys Asn Thr Ala Xaa Cys Val Leu Gly Arg Leu Ser Gln Glu Leu
 1               5                  10                  15

His Arg Leu Gln Thr Tyr Pro Arg Thr Asn Thr Gly Ser Asn Thr Tyr
                 20                  25                  30

<210> SEQ ID NO 80
<211> LENGTH: 32
<212> TYPE: PRT
<213> ORGANISM: Artificial Sequence
<220> FEATURE:
<223> OTHER INFORMATION: Description of Artificial Sequence: Synthetic
      amino acid sequence
<220> FEATURE:
<221> NAME/KEY: MOD_RES
<222> LOCATION: (6)
<223> OTHER INFORMATION: Ahp

<400> SEQUENCE: 80
```

```
Lys Cys Asn Thr Ala Xaa Cys Val Leu Gly Arg Leu Ser Gln Glu Leu
 1               5                  10                  15

His Arg Leu Gln Thr Tyr Pro Arg Thr Asn Thr Gly Ser Asn Thr Tyr
            20                  25                  30

<210> SEQ ID NO 81
<211> LENGTH: 32
<212> TYPE: PRT
<213> ORGANISM: Artificial Sequence
<220> FEATURE:
<223> OTHER INFORMATION: Description of Artificial Sequence: Synthetic
      amino acid sequence
<220> FEATURE:
<221> NAME/KEY: MOD_RES
<222> LOCATION: (6)
<223> OTHER INFORMATION: Thr(OPO3H2)

<400> SEQUENCE: 81

Lys Cys Asn Thr Ala Thr Cys Val Leu Gly Arg Leu Ser Gln Glu Leu
 1               5                  10                  15

His Arg Leu Gln Thr Tyr Pro Arg Thr Asn Thr Gly Ser Asn Thr Tyr
            20                  25                  30

<210> SEQ ID NO 82
<211> LENGTH: 32
<212> TYPE: PRT
<213> ORGANISM: Artificial Sequence
<220> FEATURE:
<223> OTHER INFORMATION: Description of Artificial Sequence: Synthetic
      amino acid sequence
<220> FEATURE:
<221> NAME/KEY: MOD_RES
<222> LOCATION: (11)
<223> OTHER INFORMATION: Orn
<220> FEATURE:
<221> NAME/KEY: MOD_RES
<222> LOCATION: (18)
<223> OTHER INFORMATION: Orn

<400> SEQUENCE: 82

Lys Cys Asn Thr Ala Thr Cys Val Leu Gly Xaa Leu Ser Gln Glu Leu
 1               5                  10                  15

His Xaa Leu Gln Thr Tyr Pro Arg Thr Asn Thr Gly Ser Asn Thr Tyr
            20                  25                  30

<210> SEQ ID NO 83
<211> LENGTH: 32
<212> TYPE: PRT
<213> ORGANISM: Artificial Sequence
<220> FEATURE:
<223> OTHER INFORMATION: Description of Artificial Sequence: Synthetic
      amino acid sequence
<220> FEATURE:
<221> NAME/KEY: MOD_RES
<222> LOCATION: (11)
<223> OTHER INFORMATION: Cit
<220> FEATURE:
<221> NAME/KEY: MOD_RES
<222> LOCATION: (18)
<223> OTHER INFORMATION: Cit

<400> SEQUENCE: 83

Lys Cys Asn Thr Ala Thr Cys Val Leu Gly Xaa Leu Ser Gln Glu Leu
 1               5                  10                  15

His Xaa Leu Gln Thr Tyr Pro Arg Thr Asn Thr Gly Ser Asn Thr Tyr
            20                  25                  30

<210> SEQ ID NO 84
```

```
<211> LENGTH: 32
<212> TYPE: PRT
<213> ORGANISM: Artificial Sequence
<220> FEATURE:
<223> OTHER INFORMATION: Description of Artificial Sequence: Synthetic
      amino acid sequence
<220> FEATURE:
<221> NAME/KEY: MOD_RES
<222> LOCATION: (11)
<223> OTHER INFORMATION: homoK
<220> FEATURE:
<221> NAME/KEY: MOD_RES
<222> LOCATION: (18)
<223> OTHER INFORMATION: homoK

<400> SEQUENCE: 84

Lys Cys Asn Thr Ala Thr Cys Val Leu Gly Lys Leu Ser Gln Glu Leu
 1               5                  10                  15

His Lys Leu Gln Thr Tyr Pro Arg Thr Asn Thr Gly Ser Asn Thr Tyr
            20                  25                  30

<210> SEQ ID NO 85
<211> LENGTH: 33
<212> TYPE: PRT
<213> ORGANISM: Artificial Sequence
<220> FEATURE:
<223> OTHER INFORMATION: Description of Artificial Sequence: Synthetic
      amino acid sequence
<220> FEATURE:
<221> NAME/KEY: MOD_RES
<222> LOCATION: (1)
<223> OTHER INFORMATION: L-Octylglycine

<400> SEQUENCE: 85

Xaa Lys Cys Asn Thr Ala Thr Cys Val Leu Gly Arg Leu Ser Gln Glu
 1               5                  10                  15

Leu His Arg Leu Gln Thr Tyr Pro Arg Thr Asn Thr Gly Ser Asn Thr
            20                  25                  30

Tyr

<210> SEQ ID NO 86
<211> LENGTH: 31
<212> TYPE: PRT
<213> ORGANISM: Artificial Sequence
<220> FEATURE:
<223> OTHER INFORMATION: Description of Artificial Sequence: Synthetic
      amino acid sequence
<220> FEATURE:
<221> NAME/KEY: MOD_RES
<222> LOCATION: (1)
<223> OTHER INFORMATION: N-3,6-dioxaoctanoyl-Cys

<400> SEQUENCE: 86

Cys Asn Thr Ala Thr Cys Val Leu Gly Arg Leu Ser Gln Glu Leu His
 1               5                  10                  15

Arg Leu Gln Thr Val Pro Arg Thr Asn Thr Gly Ser Asn Thr Tyr
            20                  25                  30

<210> SEQ ID NO 87
<211> LENGTH: 32
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 87

Lys Cys Asn Thr Ala Thr Cys Met Leu Gly Arg Tyr Thr Gln Asp Phe
 1               5                  10                  15
```

His Arg Leu Gln Thr Tyr Pro Arg Thr Asn Thr Gly Ser Asn Thr Tyr
            20                  25                  30

<210> SEQ ID NO 88
<211> LENGTH: 32
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 88

Asp Ser Asn Leu Ser Thr Lys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 89
<211> LENGTH: 32
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 89

Lys Asp Asn Thr Ala Thr Lys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 90
<211> LENGTH: 31
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 90

Cys Asn Thr Ala Thr Cys Val Leu Gly Arg Leu Ser Gln Glu Leu His
1               5                   10                  15

Arg Leu Gln Thr Tyr Pro Arg Thr Asn Thr Gly Ser Asn Thr Tyr
            20                  25                  30

<210> SEQ ID NO 91
<211> LENGTH: 33
<212> TYPE: PRT
<213> ORGANISM: Artificial Sequence
<220> FEATURE:
<223> OTHER INFORMATION: Description of Artificial Sequence: Synthetic
      amino acid sequence
<220> FEATURE:
<221> NAME/KEY: MOD_RES
<222> LOCATION: (33)
<223> OTHER INFORMATION: 9Anc

<400> SEQUENCE: 91

Lys Cys Asn Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

Xaa

<210> SEQ ID NO 92

```
<211> LENGTH: 33
<212> TYPE: PRT
<213> ORGANISM: Artificial Sequence
<220> FEATURE:
<223> OTHER INFORMATION: Description of Artificial Sequence: Synthetic
      amino acid sequence
<220> FEATURE:
<221> NAME/KEY: MOD_RES
<222> LOCATION: (33)
<223> OTHER INFORMATION: L-octylglycine

<400> SEQUENCE: 92

Lys Cys Asn Thr Ala Thr Cys Val Leu Gly Arg Leu Ser Gln Glu Leu
 1               5                  10                  15

His Arg Leu Gln Thr Tyr Pro Arg Thr Asn Thr Gly Ser Asn Thr Tyr
                20                  25                  30

Xaa

<210> SEQ ID NO 93
<211> LENGTH: 32
<212> TYPE: PRT
<213> ORGANISM: Artificial Sequence
<220> FEATURE:
<223> OTHER INFORMATION: Description of Artificial Sequence: Synthetic
      amino acid sequence
<220> FEATURE:
<221> NAME/KEY: MOD_RES
<222> LOCATION: (1)
<223> OTHER INFORMATION: N-isocaproyl-Lys

<400> SEQUENCE: 93

Lys Cys Asn Thr Ala Thr Cys Val Leu Gly Arg Leu Ser Gln Glu Leu
 1               5                  10                  15

His Arg Leu Gln Thr Tyr Pro Arg Thr Asn Thr Gly Ser Asn Thr Tyr
                20                  25                  30

<210> SEQ ID NO 94
<211> LENGTH: 32
<212> TYPE: PRT
<213> ORGANISM: Artificial Sequence
<220> FEATURE:
<223> OTHER INFORMATION: Description of Artificial Sequence: Synthetic
      amino acid sequence
<220> FEATURE:
<221> NAME/KEY: MOD_RES
<222> LOCATION: (11)
<223> OTHER INFORMATION: homoR
<220> FEATURE:
<221> NAME/KEY: MOD_RES
<222> LOCATION: (18)
<223> OTHER INFORMATION: homoR

<400> SEQUENCE: 94

Lys Cys Asn Thr Ala Thr Cys Val Leu Gly Arg Leu Ser Gln Glu Leu
 1               5                  10                  15

His Arg Leu Gln Thr Tyr Pro Arg Thr Asn Thr Gly Ser Asn Thr Tyr
                20                  25                  30

<210> SEQ ID NO 95
<211> LENGTH: 32
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 95

Phe Cys Asn Thr Ala Thr Cys Val Leu Gly Arg Leu Ser Gln Glu Leu
 1               5                  10                  15
```

```
His Arg Leu Gln Thr Tyr Pro Arg Thr Asn Thr Gly Ser Asn Thr Tyr
            20                  25                  30

<210> SEQ ID NO 96
<211> LENGTH: 32
<212> TYPE: PRT
<213> ORGANISM: Artificial Sequence
<220> FEATURE:
<223> OTHER INFORMATION: Description of Artificial Sequence: Synthetic
      amino acid sequence
<220> FEATURE:
<221> NAME/KEY: MOD_RES
<222> LOCATION: (18)
<223> OTHER INFORMATION: Cit

<400> SEQUENCE: 96

Lys Cys Asn Thr Ala Thr Cys Val Leu Gly Arg Leu Ser Gln Glu Leu
 1               5                  10                  15

His Xaa Leu Gln Thr Tyr Pro Arg Thr Asn Thr Gly Ser Asn Thr Tyr
            20                  25                  30

<210> SEQ ID NO 97
<211> LENGTH: 32
<212> TYPE: PRT
<213> ORGANISM: Artificial Sequence
<220> FEATURE:
<223> OTHER INFORMATION: Description of Artificial Sequence: Synthetic
      amino acid sequence
<220> FEATURE:
<221> NAME/KEY: MOD_RES
<222> LOCATION: (18)
<223> OTHER INFORMATION: Orn

<400> SEQUENCE: 97

Lys Cys Asn Thr Ala Thr Cys Val Leu Gly Arg Leu Ser Gln Glu Leu
 1               5                  10                  15

His Xaa Leu Gln Thr Tyr Pro Arg Thr Asn Thr Gly Ser Asn Thr Tyr
            20                  25                  30

<210> SEQ ID NO 98
<211> LENGTH: 32
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 98

Ile Cys Asn Thr Ala Thr Cys Val Leu Gly Arg Leu Ser Gln Glu Leu
 1               5                  10                  15

His Arg Leu Gln Thr Tyr Pro Arg Thr Asn Thr Gly Ser Asn Thr Tyr
            20                  25                  30

<210> SEQ ID NO 99
<211> LENGTH: 32
<212> TYPE: PRT
<213> ORGANISM: Artificial Sequence
<220> FEATURE:
<223> OTHER INFORMATION: Description of Artificial Sequence: Synthetic
      amino acid sequence
<220> FEATURE:
<221> NAME/KEY: MOD_RES
<222> LOCATION: (1)
<223> OTHER INFORMATION: 1-Octylglycine

<400> SEQUENCE: 99

Xaa Cys Asn Thr Ala Thr Cys Val Leu Gly Arg Leu Ser Gln Glu Leu
 1               5                  10                  15
```

-continued

His Arg Leu Gln Thr Tyr Pro Arg Thr Asn Thr Gly Ser Asn Thr Tyr
            20                  25                  30

<210> SEQ ID NO 100
<211> LENGTH: 31
<212> TYPE: PRT
<213> ORGANISM: Artificial Sequence
<220> FEATURE:
<223> OTHER INFORMATION: Description of Artificial Sequence: Synthetic
      amino acid sequence
<220> FEATURE:
<221> NAME/KEY: MOD_RES
<222> LOCATION: (1)
<223> OTHER INFORMATION: Isocaproyl-Cys

<400> SEQUENCE: 100

Cys Asn Thr Ala Thr Cys Val Leu Gly Arg Leu Ser Gln Glu Leu His
1               5                   10                  15

Arg Leu Gln Thr Tyr Pro Arg Thr Asn Thr Gly Ser Asn Thr Tyr
            20                  25                  30

<210> SEQ ID NO 101
<211> LENGTH: 32
<212> TYPE: PRT
<213> ORGANISM: Artificial Sequence
<220> FEATURE:
<223> OTHER INFORMATION: Description of Artificial Sequence: Synthetic
      amino acid sequence
<220> FEATURE:
<221> NAME/KEY: MOD_RES
<222> LOCATION: (11)
<223> OTHER INFORMATION: Cit

<400> SEQUENCE: 101

Lys Cys Asn Thr Ala Thr Cys Val Leu Gly Xaa Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 102
<211> LENGTH: 33
<212> TYPE: PRT
<213> ORGANISM: Artificial Sequence
<220> FEATURE:
<223> OTHER INFORMATION: Description of Artificial Sequence: Synthetic
      amino acid sequence
<220> FEATURE:
<221> NAME/KEY: MOD_RES
<222> LOCATION: (33)
<223> OTHER INFORMATION: 4ABU

<400> SEQUENCE: 102

Lys Cys Asn Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

Xaa

<210> SEQ ID NO 103
<211> LENGTH: 33
<212> TYPE: PRT
<213> ORGANISM: Artificial Sequence
<220> FEATURE:
<223> OTHER INFORMATION: Description of Artificial Sequence: Synthetic
      amino acid sequence
<220> FEATURE:
<221> NAME/KEY: MOD_RES
<222> LOCATION: (1)

```
<223> OTHER INFORMATION: Isocaproyl-Lys
<220> FEATURE:
<221> NAME/KEY: MOD_RES
<222> LOCATION: (33)
<223> OTHER INFORMATION: 4ABU

<400> SEQUENCE: 103

Lys Cys Asn Thr Ala Thr Cys Val Leu Gly Arg Leu Ser Gln Glu Leu
 1               5                  10                  15

His Arg Leu Gln Thr Tyr Pro Arg Thr Asn Thr Gly Ser Asn Thr Tyr
             20                  25                  30

Xaa

<210> SEQ ID NO 104
<211> LENGTH: 32
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 104

Lys Cys Asn Thr Ser Thr Cys Ala Thr Gln Arg Leu Ala Asn Glu Leu
 1               5                  10                  15

Val Arg Leu Gln Thr Tyr Pro Arg Thr Asn Val Gly Ser Glu Ala Phe
             20                  25                  30

<210> SEQ ID NO 105
<211> LENGTH: 31
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 105

Lys Cys Asn Thr Ala Thr Cys Val Leu Gly Arg Leu Ser Gln Glu Leu
 1               5                  10                  15

His Arg Leu Gln Thr Tyr Pro Thr Asn Val Gly Ser Glu Ala Phe
             20                  25                  30

<210> SEQ ID NO 106
<211> LENGTH: 32
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 106

Lys Cys Asn Thr Ala Thr Cys Val Leu Gly Arg Leu Ser Arg Ser Leu
 1               5                  10                  15

His Arg Leu Gln Thr Tyr Pro Arg Thr Asn Thr Gly Ser Asn Thr Tyr
             20                  25                  30

<210> SEQ ID NO 107
<211> LENGTH: 32
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 107

Lys Cys Asn Thr Ala Thr Cys Val Thr His Arg Leu Ser Gln Glu Leu
 1               5                  10                  15
```

```
His Arg Leu Gln Thr Tyr Pro Arg Thr Asn Thr Gly Ser Asn Thr Tyr
            20                  25                  30
```

<210> SEQ ID NO 108
<211> LENGTH: 32
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 108

```
Lys Cys Asn Thr Ala Thr Cys Val Leu Gly Arg Leu Ala Asp Phe Leu
 1               5                  10                  15

His Arg Leu Gln Thr Tyr Pro Arg Thr Asn Thr Gly Ser Asn Thr Tyr
            20                  25                  30
```

<210> SEQ ID NO 109
<211> LENGTH: 30
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 109

```
Cys Asn Thr Ala Thr Cys Val Leu Gly Arg Leu Ser Gln Glu Leu His
 1               5                  10                  15

Arg Leu Gln Thr Tyr Pro Arg Thr Asn Thr Gly Ser Asn Thr
            20                  25                  30
```

<210> SEQ ID NO 110
<211> LENGTH: 33
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 110

```
Lys Cys Asn Thr Ala Thr Cys Val Leu Gly Arg Leu Ser Gln Glu Leu
 1               5                  10                  15

His Arg Leu Gln Asn Phe Val Pro Arg Thr Asn Thr Gly Ser Asn Thr
            20                  25                  30

Tyr
```

<210> SEQ ID NO 111
<211> LENGTH: 32
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 111

```
Lys Cys Asn Thr Ala Thr Cys Val Leu Gly Arg Leu Ser Gln Glu Leu
 1               5                  10                  15

His Arg Leu Gln Thr Tyr Pro Arg Thr Asn Thr Gly Ser Glu Thr Phe
            20                  25                  30
```

<210> SEQ ID NO 112
<211> LENGTH: 32
<212> TYPE: PRT
<213> ORGANISM: Artificial Sequence
<220> FEATURE:

<223> OTHER INFORMATION: Description of Artificial Sequence: Synthetic
      amino acid sequence

<400> SEQUENCE: 112

Ala Cys Asp Thr Ala Thr Cys Val Leu Gly Arg Leu Ser Gln Glu Leu
 1               5                  10                  15

His Arg Leu Gln Thr Tyr Pro Arg Thr Asn Thr Gly Ser Asn Thr Tyr
            20                  25                  30

<210> SEQ ID NO 113
<211> LENGTH: 32
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 113

Lys Cys Asn Thr Ala Thr Cys Val Leu Gly Arg Leu Ser Gln Glu Leu
 1               5                  10                  15

His Arg Leu Gln Thr Tyr Pro Arg Thr Asn Thr Gly Ser Lys Ala Phe
            20                  25                  30

<210> SEQ ID NO 114
<211> LENGTH: 32
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 114

Lys Cys Asp Thr Ala Thr Cys Val Thr His Arg Leu Ala Gly Leu Leu
 1               5                  10                  15

Ser Arg Ser Gln Thr Tyr Pro Arg Thr Asn Thr Gly Ser Asn Thr Tyr
            20                  25                  30

<210> SEQ ID NO 115
<211> LENGTH: 32
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 115

Lys Cys Asn Thr Ala Thr Cys Val Leu Gly Arg Leu Ala Asp Ala Leu
 1               5                  10                  15

His Arg Leu Gln Thr Tyr Pro Arg Thr Asn Thr Gly Ser Asn Thr Tyr
            20                  25                  30

<210> SEQ ID NO 116
<211> LENGTH: 32
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 116

Lys Cys Asn Thr Ala Thr Cys Val Leu Gly Arg Leu Ala Ala Phe Leu
 1               5                  10                  15

His Arg Leu Gln Thr Tyr Pro Arg Thr Asn Thr Gly Ser Asn Thr Tyr
            20                  25                  30

```
<210> SEQ ID NO 117
<211> LENGTH: 32
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 117

Ser Cys Asn Thr Ala Thr Cys Val Leu Gly Arg Leu Ala Asp Phe Leu
 1               5                  10                  15

His Arg Leu Gln Thr Tyr Pro Arg Thr Asn Thr Gly Ser Asn Thr Tyr
            20                  25                  30

<210> SEQ ID NO 118
<211> LENGTH: 32
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 118

Lys Cys Asn Thr Ala Thr Cys Val Leu Gly Arg Leu Ser Gln Glu Leu
 1               5                  10                  15

His Arg Leu Gln Thr Met Pro Arg Thr Asn Thr Gly Ser Asn Thr Tyr
            20                  25                  30

<210> SEQ ID NO 119
<211> LENGTH: 32
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 119

Lys Cys Asn Thr Ala Thr Cys Val Leu Gly Arg Leu Ser Gln Glu Leu
 1               5                  10                  15

His Arg Leu Gln Thr Val Pro Arg Thr Asn Thr Gly Ser Asn Thr Tyr
            20                  25                  30

<210> SEQ ID NO 120
<211> LENGTH: 32
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 120

Lys Cys Asn Thr Ala Thr Cys Val Leu Gly Arg Leu Asn Glu Tyr Leu
 1               5                  10                  15

His Arg Leu Gln Thr Tyr Pro Arg Thr Asn Thr Gly Ser Asn Thr Tyr
            20                  25                  30

<210> SEQ ID NO 121
<211> LENGTH: 32
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 121

Ser Cys Asn Thr Ala Thr Cys Val Leu Gly Arg Leu Ser Gln Glu Leu
 1               5                  10                  15
```

His Arg Leu Gln Thr Tyr Pro Arg Thr Asn Thr Gly Ser Asn Thr Tyr
            20                  25                  30

<210> SEQ ID NO 122
<211> LENGTH: 32
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 122

Lys Cys Asn Thr Ala Thr Cys Val Leu Gly Arg Leu Thr Glu Phe Leu
 1               5                  10                  15

His Arg Leu Gln Thr Tyr Pro Arg Thr Asn Thr Gly Ser Asn Thr Tyr
            20                  25                  30

<210> SEQ ID NO 123
<211> LENGTH: 32
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 123

Lys Cys Asn Thr Ala Thr Cys Val Leu Gly Arg Leu Ala Glu Phe Leu
 1               5                  10                  15

His Arg Leu Gln Thr Tyr Pro Arg Thr Asn Thr Gly Ser Asn Thr Tyr
            20                  25                  30

<210> SEQ ID NO 124
<211> LENGTH: 32
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 124

Lys Cys Asn Thr Ala Thr Cys Val Leu Gly Arg Leu Thr Asp Tyr Leu
 1               5                  10                  15

His Arg Leu Gln Thr Tyr Pro Arg Thr Asn Thr Gly Ser Asn Thr Tyr
            20                  25                  30

<210> SEQ ID NO 125
<211> LENGTH: 32
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 125

Lys Cys Asn Thr Ala Thr Cys Val Leu Gly Arg Leu Ala Gln Phe Leu
 1               5                  10                  15

His Arg Leu Gln Thr Tyr Pro Arg Thr Asn Thr Gly Ser Asn Thr Tyr
            20                  25                  30

<210> SEQ ID NO 126
<211> LENGTH: 32
<212> TYPE: PRT
<213> ORGANISM: Artificial Sequence
<220> FEATURE:
<223> OTHER INFORMATION: Description of Artificial Sequence: Synthetic
      amino acid sequence

```
<400> SEQUENCE: 126

Lys Cys Asn Thr Ala Thr Cys Val Leu Gly Arg Leu Ala Asp Phe Leu
 1               5                  10                  15

His Arg Phe Gln Thr Phe Pro Arg Thr Asn Thr Gly Ser Asn Thr Tyr
             20                  25                  30

<210> SEQ ID NO 127
<211> LENGTH: 32
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 127

Lys Cys Asn Thr Ala Thr Cys Val Leu Gly Arg Leu Ala Asp Phe Leu
 1               5                  10                  15

His Arg Phe His Thr Phe Pro Arg Thr Asn Thr Gly Ser Asn Thr Tyr
             20                  25                  30

<210> SEQ ID NO 128
<211> LENGTH: 32
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 128

Lys Cys Asn Thr Ala Thr Cys Val Leu Gly Arg Leu Ala Asp Phe Leu
 1               5                  10                  15

His Arg Phe Gln Thr Phe Pro Arg Thr Asn Thr Gly Ser Gly Thr Pro
             20                  25                  30

<210> SEQ ID NO 129
<211> LENGTH: 31
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 129

Cys Asn Thr Ala Thr Cys Val Leu Gly Arg Leu Ala Asp Phe Leu His
 1               5                  10                  15

Arg Leu Gln Thr Tyr Pro Arg Thr Asn Thr Gly Ser Asn Thr Tyr
             20                  25                  30

<210> SEQ ID NO 130
<211> LENGTH: 32
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 130

Lys Cys Asp Thr Ala Thr Cys Val Leu Gly Arg Leu Ser Gln Glu Leu
 1               5                  10                  15

His Arg Leu Gln Thr Tyr Pro Arg Thr Asn Thr Gly Ser Asn Thr Tyr
             20                  25                  30

<210> SEQ ID NO 131
<211> LENGTH: 32
```

```
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 131

Lys Cys Asn Thr Ala Thr Cys Val Leu Gly Arg Leu Phe Asp Phe Leu
 1               5                  10                  15

His Arg Leu Gln Thr Tyr Pro Arg Thr Asn Thr Gly Ser Asn Thr Tyr
            20                  25                  30

<210> SEQ ID NO 132
<211> LENGTH: 32
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 132

Lys Cys Asn Thr Ala Thr Cys Val Leu Gly Arg Leu Ala Ala Ala Leu
 1               5                  10                  15

His Arg Leu Gln Thr Tyr Pro Arg Thr Asn Thr Gly Ser Asn Thr Tyr
            20                  25                  30

<210> SEQ ID NO 133
<211> LENGTH: 32
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 133

Thr Cys Asp Thr Ala Thr Cys Val Leu Gly Arg Leu Ser Gln Glu Leu
 1               5                  10                  15

His Arg Leu Gln Thr Tyr Pro Arg Thr Asn Thr Gly Ser Asn Thr Tyr
            20                  25                  30

<210> SEQ ID NO 134
<211> LENGTH: 32
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 134

Cys Ser Asn Leu Ser Thr Cys Ala Thr Gln Arg Leu Ala Asn Glu Leu
 1               5                  10                  15

Val Arg Leu Gln Thr Tyr Pro Arg Thr Asn Val Gly Ser Asn Thr Tyr
            20                  25                  30

<210> SEQ ID NO 135
<211> LENGTH: 32
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 135

Lys Cys Asn Thr Ala Thr Cys Ala Thr Gln Arg Leu Ala Asn Glu Leu
 1               5                  10                  15

Val Arg Leu Gln Thr Tyr Pro Arg Thr Asn Val Gly Ser Asn Thr Tyr
```

```
                20                  25                  30

<210> SEQ ID NO 136
<211> LENGTH: 32
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 136

Cys Ser Asn Leu Ser Thr Cys Val Leu Gly Arg Leu Ser Gln Glu Leu
 1               5                  10                  15

His Arg Leu Gln Thr Tyr Pro Arg Thr Asn Thr Gly Ser Asn Thr Tyr
                20                  25                  30

<210> SEQ ID NO 137
<211> LENGTH: 32
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 137

Lys Cys Asn Thr Ala Thr Cys Val Leu Gly Arg Leu Ser Gln Glu Leu
 1               5                  10                  15

His Arg Leu Gln Thr Tyr Pro Arg Thr Asn Thr Gly Ser Asn Thr Tyr
                20                  25                  30

<210> SEQ ID NO 138
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Any amino acid; see specification as filed
      for detailed description of substitutions and
      preferred embodiments
<220> FEATURE:
<221> NAME/KEY: MOD_RES
<222> LOCATION: (2)
<223> OTHER INFORMATION: Any amino acid or not present
<220> FEATURE:
<221> NAME/KEY: MOD_RES
<222> LOCATION: (3)
<223> OTHER INFORMATION: Ala, Gly, Ser, Asp, or not present
<220> FEATURE:
<221> NAME/KEY: MOD_RES
<222> LOCATION: (4)
<223> OTHER INFORMATION: Asn, Ala, Asp, Gly, or not present
<220> FEATURE:
<221> NAME/KEY: MOD_RES
<222> LOCATION: (5)
<223> OTHER INFORMATION: Ala, Leu, Thr, or Ser
<220> FEATURE:
<221> NAME/KEY: MOD_RES
<222> LOCATION: (6)
<223> OTHER INFORMATION: Ala, Ser, or Thr
<220> FEATURE:
<221> NAME/KEY: MOD_RES
<222> LOCATION: (7)
<223> OTHER INFORMATION: Ala, Ser, Val, Hse, Ahb, Ahp, D-thr, Thr, or a
      derivative thereof
<220> FEATURE:
<221> NAME/KEY: MOD_RES
<222> LOCATION: (8)
<223> OTHER INFORMATION: Any amino acid; see specification as filed
      for detailed description of substitutions and
```

-continued

```
preferred embodiments

<400> SEQUENCE: 138

Xaa Xaa Xaa Xaa Xaa Xaa Xaa Xaa
 1               5
```